US008524475B1

(12) United States Patent
Templeton

(10) Patent No.: US 8,524,475 B1
(45) Date of Patent: Sep. 3, 2013

(54) POLYPEPTIDES HAVING COLANIC ACID-DEGRADING ACTIVITY

(71) Applicant: Gradalis, Inc., Carrollton, TX (US)

(72) Inventor: Nancy Smyth Templeton, Houston, TX (US)

(73) Assignee: Gradalis, Inc., Carrollton, TX (US)

( * ) Notice: Subject to any disclaimer, the term of this patent is extended or adjusted under 35 U.S.C. 154(b) by 0 days.

(21) Appl. No.: 13/858,697

(22) Filed: Apr. 8, 2013

Related U.S. Application Data

(63) Continuation of application No. 12/433,691, filed on Apr. 30, 2009.

(60) Provisional application No. 61/125,916, filed on Apr. 30, 2008, provisional application No. 61/125,923, filed on Apr. 30, 2008.

(51) Int. Cl.
C12N 9/00 (2006.01)
C12N 1/20 (2006.01)
C12N 15/00 (2006.01)
C07H 21/04 (2006.01)

(52) U.S. Cl.
USPC ............. 435/183; 435/252.3; 435/252.33; 435/254.1; 435/325; 435/410; 435/320.1; 536/23.2

(58) Field of Classification Search
None
See application file for complete search history.

(56) References Cited

U.S. PATENT DOCUMENTS

| | | | |
|---|---|---|---|
| 4,634,677 | A | 1/1987 | Goeddel et al. |
| 5,747,663 | A | 5/1998 | Colpan et al. |
| 5,808,041 | A | 9/1998 | Padhye et al. |
| 5,898,071 | A | 4/1999 | Hawkins |
| 5,969,129 | A | 10/1999 | Caddy et al. |
| 6,069,230 | A | 5/2000 | Knuth et al. |
| 6,194,562 | B1 | 2/2001 | Smith et al. |
| 6,297,371 | B1 | 10/2001 | Colpan et al. |
| 6,503,738 | B1 | 1/2003 | Thatcher et al. |
| 6,504,021 | B2 | 1/2003 | Kristyanne et al. |
| 6,617,108 | B1 | 9/2003 | Willson, III et al. |
| 7,041,814 | B1 | 5/2006 | Weinstock et al. |
| 2002/0010145 | A1 | 1/2002 | Willson, III et al. |
| 2002/0197637 | A1 | 12/2002 | Willson, III et al. |
| 2003/0064951 | A1 | 4/2003 | Bussey et al. |
| 2007/0213289 | A1 | 9/2007 | Blanche et al. |
| 2009/0068707 | A1 | 3/2009 | Blattner et al. |

FOREIGN PATENT DOCUMENTS

| | | |
|---|---|---|
| WO | 9520594 A1 | 8/1995 |
| WO | 9631610 A2 | 10/1996 |
| WO | 2005100542 A1 | 10/2005 |
| WO | 2009042382 | 4/2009 |

OTHER PUBLICATIONS

Allen, P, et al., "Isolatioln from *Klebsiella* and Characterization of Two rcs Genes That Activate Colanic Acid Capsular Biosynthesis in *Escherichia coli*", Journal of General Microbiology, 1987, 133, 331-340.

Berg, KA, et al., "A Conservative, Single-Amino Acid Substitution in the Second Cytoplasmic Domain of the Human Serotonin2c Receptor Alters Both Ligand-Dependent and -Independent Receptor Signaling", The Journal of Pharmacology and Experimental Therapeutic, 2008, 324 No. 5, 1084-1092.

Bruschi, CV, et al., "Introduction of nonselectible 2u Plasmid into [cir] Cells of the Yeast *S. cerevisiae* by DNA Transformation and in Vivo Site-Specific Resolution", Current Genetics, 1989, 15:83-90.

Dierksen, KP, et al., "Identification of a Second RcsA Protein, a Positive Regulator of Colanic Acid Ca[psular Polysaccharide Genes, in *Escherichia coli*", Journal of Bacteriology, Aug. 1996, 5053-5056.

Diogo, M.M., et al., "Chromatography of Plasmid DNA", 2005, Journal of Chromatography, 3-22.

EESR, Jul. 12, 2011, Application No. 09739850.7.

Ferreira, G.N.M., et al., "A Comparison of Gel Filtration Chromatographic Supports for Plasmid Purification", Biotechnology Techniques, Jun. 1997, 11:417-420.

Firozi, P., et al., "Identification and Removal of Colanic Acid from Plasmid DNA Preparations: Implications for Gene Therapy", XP-002645090, Gene Therapy, 2010, 17:1484-1499.

Gencic, S., et al., "Conservative Amino Acid Substitution in the Myelin Proteolipid Protein of Jimpy-msd Mice", The Journal of Neuroscience, Jan. 1990, 10(1): 117-124.

Gromova, E.S., et al., "Prokaryotic DNA Methyltransferases: The Structure and the Mechanism of Interaction with DNA", 2003, Molecular Biology, 37(2), 260-272.

Keenleyside, W.J., et al., "Coexpression of Colanic Acid and Serotype-Specific Capsular Polysaccharides in *Escherichia coli* Strains with Group II K Antigens", Journal of Bacteriology, Oct. 1993, 175(20): 6725.

Liu, Shi V., "An Improved Colorimetric Assay for Vicinal Diol Determination by TI(III) and its Utilization for Reporting Microbial O-Demethylation", Journal of Microbiological Methods, 1997, 29:85-95.

Nixon, A. E., et al., "Hybrid Enzymes: Manipulating Enzyme Design", Tibtech, Jun. 1998, vol. 16: 258-264.

Sampaio, Maria-Manuel, et al., Synthesis of GDP-Mannose and Mannosylglycerate from Labeled Mannose by Genetically Engineered *Escherichia coli* Without Loss of Specific Isotopic Enrichment, Applied and Environmental Microbiology, Jan. 2003, 69(1):233-240.

Stadler, J., et al., Plasmid DNA Purification, The Journal of Gene Medicine, Feb. 2004, 6(/S1): S54-S66.

Wang, L., et al., "Phosphorothioation of DNA in Bacteria by dnd Genes", Nature Chemical Biology, Nov. 2007, 3(11):709-711.

Wang, L., et al., "DNA Phosphorothioation is Widespread and Quantized in Bacterial Genomes", PNAS, Feb. 15, 2011, 108(7):2963-2968.

(Continued)

Primary Examiner — Nashaat Nashed
(74) Attorney, Agent, or Firm — Edwin S. Flores; Chalker Flores, LLP

(57) ABSTRACT

The present disclosure generally relates to polypeptides having colanic acid-degrading activity and methods of using the same. Polynucleotides encoding such polypeptides are also described. The polypeptides may be used, for example, in processes for degrading colanic acid, processes for the removal of endotoxins from biological samples, and processes for purifying plasmid DNA.

24 Claims, 17 Drawing Sheets

(56) References Cited

OTHER PUBLICATIONS

Wicken, A. J., "Bacterial Cell Walls and Surfaces, in Bacterial adhesion", 1985, D. M. Pletcher, ed. Penum Press: New York, pp. 45-70.
Zhang, Duo, et al., "Removal of Endotoxin from Plasmid Solutions by Triton X-114 Phase Separation", Letters in Biotechnology, Nov. 2007, 18(6): 971-973.
Sutherland, I.W., "Enzymic Hydrolysis of Colanic Acid", Eur. J. Biochem, 1971, 23:582-587.
Adams, R., "A Simple Technique for Removing Plant Polysaccharide Contaminants from DNA", BioFeedback, 1991, 10(2):164-166.
Verhoef, R., et al., "Characterisation of a 1,4-beta-fucoside hydrolase degrading colanic acid", Carbohydrate Research, 2005, 340:1780-1788.
Zhao, Y, et al., "Chiral Separation of Systhetic Vicinal Diol Compounds by Capillary Zone El;ectrophoresis with Borate Buffer and B-Cyclodextrin as Buffer Additive", Analytical Sciences, May 2006, 22, 747-751.
Templeton, et al., "Improved DNA: Liposome Complexes for Increased Systemic Delivery and Gene Expression", Nature Publishing Group, Jul. 1997, 15, 647-652.
Ingalls, R.R., et al., "CD11/CD18 and Cd14 Share a Common Lipid a Signaling Pathway", J. Immunol. 1998, vol. 161, 5413-5420.
Hughes, K.A., et al., "Bacteriophage and Associated Polysaccharide Depolymerases—Novel Tools for Study of Bacterial Biofilms", Journal of AppliedMicrobiology, 1998, 85:583-590.
Aoki, Y., et al., "Inhibitory Effects of Acid Polysaccharides from Sea Urchin Embryos on RNA Polymerase Activity", Biochimica et Biophysica Acta, 1972, 33-43.
Barry, M., et al., "Observation of 13 C Rearrangement in [13C2] Biphenylene Formed from Benzyne on Pyrolysis of [1,6-13C2] Phthalic Anhydride and [2a,3-13C2] Benzocyclobutenedione", Aust. J. chem., 1984, 37:1643-57.
Birnboim, H.C., et al., "A Rapid Alkaline Extraction procedure for Screening Recombinant Plasmid DNA", 1979, 7 (6):1513-1523.
Edelman, M., "Purification of DNA by Affinity Chromatography: Removal of Polysaccharide Contaminants", Analytical Biochemistry, 1975, 65:293-297.
Fields, P.A., et al., "Role of Vector in Activation of T Cell Subsets in Immune Responses Against the Secreted Transgene Product Factor IX", Molecular Therapy, Mar. 2000, 1(3): 225-235.
Gable, K. P., "Condensation of Vicinal Diols with the Oxo Complex {Cp*Re(O)} 2 (u-O)2 Giving the Corresponding Diolate Complexes" Organometallics, 1994, 13, 2486-2488.
Horowicz, D., et al., "Rapid and Efficient Cosmid Cloning" Nucleic Acids Research, 1981, 9(13):2289-2998.

Jann, B., et al., "Structure and Biosynthesis of the Capsular antigens of *Escherichia coli*" Current Topics in Microbiology and Immunology, 1990, 150:19-42.
Jerkovic, B., et al., "Purification of Thymine Glycol DNA and Nucleosides by Use of Boronate Chromatography", Analytical Biochemistry, 1998, 255:90-94.
Kinrade, S. D., et al., "Complexes of Pentaoxo and Hexaoxo Silicon with Furanoidic Vicinal Cis-Diols in Aqueous Solution", Dalton Trans., 2003, 3713-3716.
Liu, X-C., et al., "Boronate Affinity Chromatography", Chapter, Handbook of Affinity Chrmatography, pp. 215-230, David S. Hage (ed) CRC Press (2006).
Meeuwsen, P., J.A., et al., "A Universal Assay for Screening Expression Libraries for Carbohydrases", Jurnal of Bioscience and Bioengineering, 2000, 89(1):107-109.
Morris, J. B., "Enzymatic Assay for Subnanomole Amounts of L-Fucose", Analytical Biochemistry, 1982, 121:129-134.
Neudecker, F., et al., "Short Technical Reports", May 1999.
Passonneau, J.V. et al., "Methods of Enzymatic Analysis", Nicotinamide-Adenine, 1974, 4:2059-2072.
Prazeres, Duarte, M.F., et al. "Preparative Purification of Supercoiled Plasmid DNA Using Anion-exchange Chromatography", Journal of Chromatography, 1998, 806:31-45.
Pruess-Schwartz, D., et al., "Analysis of Benzo(a)Pyrene: DNA Adducts Formed in Cells in Culture by Immobilized Boronate Chromatograph", Cancer Research, Sep. 1984, 44:4104-4110.
Qiagen Plasmid Purification Handbook, Jul. 1999.
Schott, H., et al., "A Dihydroxyboryl-Substituted Methacrylic Polymer for the Column Chromatographic Separation of Mononucleotides, Oligonucleotides, and Transfer Ribonucleic Acid", Biochemistry, 1973, 12, nc. 5:932-938.
Shioda, M., et al., "Selective Inhibition of DNA Polymerase & by a Polysaccharide Purified Frm Slime of *Physarum polycephalum*", Biochemical and Biophysical Research Communications, Jul. 15, 1987, 146(1):61-66.
Singh, N., et al., "Boronate Affinity Adsorption of RNA: Possible Role of Conformational Changes", Journal of Chromatography A, 1999, 840:205-213.
Sutherland, I.W., Phage-Induced Fucosidases Hydrolysing the Exopolysaccharide of *Klebsiella* Aerogenes Type 54 [A3(S1)], Biochem. J. 1967, 104:278-285.
Sutherland, I.W., "Structural Studies on Colanic Acid, the Common Exopolysaccharide Found in the Enterobacteriaceae, by Partial Acid Hydrolysis", Biochem. J., 1969 115:935-945.
Weber, M.K., et al., "Effects of Lipopolysaccharide on Transfection Efficiency in Eukaryotic Cells", Short Technical Reports, 1995, 19(6).

```
Frame 1  Met Ala Asn Ser Tyr Asn Ala Tyr Val Ala Asn Gly Ser Gln Thr Ala Phe
         ATG GCG AAC AGC TAT AAT GCT TAC GTG GCG AAC GGT TCA CAG ACC GCA TTC
                     9          18          27          36          45

Leu Val Thr Phe Glu Gln Arg Val Phe Thr Glu Ile Gln Val Tyr Leu Asn Ser Glu
         CTC GTC ACG TTC GAG CAG CGC GTG TTC ACT GAG ATT CAG GTG TAC CTC AAC TCC GAA
                     60          69          78          87          96          105

Leu Gln Thr Glu Gly Tyr Thr Tyr Asn Ser Val Thr Lys Gln Ile Ile Phe Asp Thr
         CTC CAG ACG GAA GGG TAC ACC TAC AAC TCT GTG ACC AAA CAG ATT ATC TTC GAC ACC
                     117         126         135         144         153         162

Ala Pro Leu Ala Gly Val Ile Val Arg Leu Gln Arg Tyr Thr Ser Glu Val Leu Leu
         GCC CCG CTC GCC GGG GTG ATT GTC CGA CTC CAA CGC TAC ACC TCT GAG GTT CTG CTG
                     174         183         192         201         210         219

Asn Lys Phe Gly Gln Asp Ala Ala Phe Thr Gly Gln Asn Leu Asp Glu Asn Phe Glu
         AAC AAG TTT GGC CAA GAC GCT GCC TTC ACC GGG CAG AAC CTT GAC GAG AAC TTT GAG
                     231         240         249         258         267         276

Gln Ile Leu Phe Lys Ala Glu Glu Thr Gln Glu Ala Trp Leu Ala Pro Leu Asp Arg
         CAG ATT CTG TTC AAG GCT GAG GAA ACT CAG GAA GCA TGG CTC GCG CCA CTT GAC CGC
                     288         297         306         315         324         333

Ala Val Arg Val Pro Asn Ser Glu Val Ser Ile Asn Ala Leu Pro Asn Val Ala Gly
         GCC GTC CGT GTT CCG AAC TCC GAA GTC TCC ATC AAC GCA TTA CCG AAC GTC GCT GGC
                     345         354         363         372         381         390

Arg Arg Asn Lys Ala Leu Gly Phe Asp Ser Asn Gly Gln Pro Phe Met Ile Pro Leu
         CGC CGC AAC AAG GCA CTG GGC TTT GAC AGC AAT GGT CAG CCG TTC ATG ATT CCT CTG
                     402         411         420         429         438         447

Val Asp Ile Pro Asp Ser Ala Leu Ala Ile Ala Leu Ala Met Ala Asp Gly Gly Lys
         GTC GAT ATC CCG GAC TCC GCG CTG GCG ATT GCT CTG GCA ATG GCT GAC GGC GGT AAG
                     459         468         477         486         495         504

Trp Ile Gly Thr Leu Gly Gly Gly Thr Phe Leu Asp Arg Gln Asp Thr Val Cys Leu
         TGG ATT GGT ACT CTC GGC GGG GGC ACG TTC CTC GAC CGT CAG GAT ACC GTC TGC CTG
                     516         525         534         543         552         561
```

*FIG. 1A*

```
Ser Glu Phe Thr Asn Asn Thr Gly Tyr Ala Ser Val Ala Ala Ala Val Gln Ala Cys
TCC GAG TTC ACC AAC AAC ACT GGG TAC GCC TCT GTC GCC GCT GCG GTG CAG GCT TGC
        573         582         591         600         609         618

Phe Asp Tyr Ala Lys Ala Asn Gly Lys Val Val Asp Ala Arg Gly Trp Glu Gly Thr
TTC GAC TAT GCG AAA GCC AAC GGC AAG GTC GTT GAC GCT CGC GGC TGG GAA GGT ACG
        630         639         648         657         666         675

Val Asp Ser Thr Val Leu Met Asp Gly Ile Glu Val Val Gly Gly Thr Trp His Gly
GTG GAT TCC ACT GTG CTG ATG GAC GGT ATT GAG GTC GTC GGC GGT ACG TGG CAC GGC
        687         696         705         714         723         732

Lys Ala Asp Ile Arg Leu Leu Asn ser Thr Phe Arg Asn Phe Val Ala Ser Thr Val
AAG GCT GAC ATT CGC CTG CTG AAC TCC ACC TTC CGC AAC TTC GTG GCC TCT ACT GTC
        744         753         762         771         780         789

Arg Val Ala Tyr Trp Gly Gly Glu Val Arg Ile Ala Asp Tyr Glu Phe Thr Ser Ala
CGT GTC GCC TAC TGG GGC GGC GAG GTG CGT ATT GCT GAC TAT GAG TTC ACC AGC GCA
        801         810         819         828         837         846

Pro Ser Asn Ser Lys Val Thr Ser Ile Leu Phe Gln Gly Asn Ile Ala Gly Gly Ser
CCG AGC AAC TCC AAG GTT ACG TCT ATC CTG TTC CAA GGC AAC ATC GCC GGG GGC AGC
        858         867         876         885         894         903

Tyr Val Ile Glu Asn Gly Ile His Arg Asn Gly Lys Phe Gly Ile Leu Gln Gln Gly
TAC GTC ATT GAG AAC GGT ATC CAC CGC AAT GGT AAG TTC GGT ATT CTC CAA CAG GGT
        915         924         933         942         951         960

Thr Gly Glu Ala Ile Thr Asn Gly Val Ile Arg Gly Ile Thr Met Met Asp Met Gln
ACT GGC GAG GCT ATC ACC AAC GGC GTT ATC CGT GGC ATC ACC ATG ATG GAT ATG CAG
        972         981         990         999        1008        1017

Gly Asp Gly Ile Glu Met Asn Val Ile Asn Lys His Tyr Asp Gly Gly Leu Leu Ile
GGT GAC GGT ATC GAG ATG AAC GTA ATC AAC AAG CAC TAT GAT GGT GGC CTG CTG ATT
       1029        1038        1047        1056        1065        1074

Glu Asn Ile Phe Leu Glu Asn Ile Asp Gly Thr Asn Ala Pro Ile Pro Leu Ser Asn
GAG AAC ATC TTC CTT GAG AAC ATC GAC GGC ACC AAC GCG CCT ATC CCA CTG TCC AAC
       1086        1095        1104        1113        1122        1131

Trp Gly Ile Gly Ile Gly Ile Ala Gly Gln Gly Pro Phe Gly Trp Asp Ala Ala Glu
TGG GGC ATT GGT ATC GGT ATC GCT GGT CAA GGC CCG TTC GGT TGG GAT GCT GCT GAG
       1143        1152        1161        1170        1179        1188
```

*FIG. 1B*

```
Thr Gln Tyr Ala Lys Asn Val Thr Val Arg Asn Val His Ala Pro Arg Gly Val Arg
ACG CAG TAT GCG AAG AAC GTC ACT GTC CGT AAC GTC CAT GCT CCG CGT GGT GTG CGT
        1200        1209        1218        1227        1236        1245

Gln Val Val His Phe Glu Val Thr Arg Asp Ser Thr Cys Glu Asn Val Val Ala Asn
CAG GTC GTC CAC TTC GAG GTT ACG CGT GAC AGC ACC TGC GAG AAC GTA GTG GCC AAC
        1257        1266        1275        1284        1293        1302

Pro Asp Leu Ser Val Ser Ile Gly Thr Gly Leu Thr Ala Ala Gly Val Ile Thr Tyr
CCT GAC CTG TCC GTC TCC ATT GGT ACT GGC CTG ACT GCC GCT GGT GTA ATC ACG TAC
        1314        1323        1332        1341        1350        1359

Gly Cys Lys Arg Met Thr Ile Asp Gly Val Val Gly Glu Pro Met Asn Thr Gly Ala
GGC TGC AAG CGC ATG ACC ATT GAC GGT GTA GTC GGT GAG CCT ATG AAC ACC GGA GCA
        1371        1380        1389        1398        1407        1416

Thr Ser Pro Asn Asp Ile Arg Ile Val Met Leu Glu Trp Gly Ala Asn Gln Ala Gly
ACC TCT CCG AAC GAT ATT CGT ATC GTG ATG TTG GAG TGG GGT GCG AAC CAA GCA GGT
        1428        1437        1446        1455        1464        1473

Ala Gly Gly Thr Pro Gly Ala Ala Cys Pro Ser Phe Asp Met Thr Val Arg Asn Val
GCT GGC GGT ACG CCG GGT GCA GCT TGC CCA TCG TTC GAC ATG ACC GTG CGT AAC GTG
        1485        1494        1503        1512        1521        1530

Gln Thr Arg Thr Gly Arg Phe Tyr Ala Gly Val Gly Ser Asp Asp Asp Asn Thr Asn
CAG ACC CGT ACC GGG CGC TTC TAT GCT GGT GTC GGC TCC GAC GAT GAC AAC ACC AAC
         1542        1551        1560        1569        1578        1587

Thr Tyr His Leu Glu Asn Ile His Cys Tyr Lys Met Thr Leu Phe Gly Val Ala Thr
ACA TAT CAC CTT GAA AAC ATT CAC TGT TAC AAG ATG ACG CTG TTT GGT GTG GCA ACT
        1599        1608        1617        1626        1635        1644

Leu Leu Asn Met Thr Asn Val Thr Gly Val Val Phe Asp Ala Val Gly Asp Asp Ser
CTG CTG AAC ATG ACC AAC GTG ACT GGT GTG GTG TTC GAC GCT GTA GGC GAT GAC TCC
        1656        1665        1674        1683        1692        1701

Ser Gly Gly Thr Ser Ser Asn Gly Leu Tyr Pro Arg Lys Lys Thr Val Leu Asn Met
AGC GGC GGT ACG TCC TCC AAC GGT CTG TAC CCG CGT AAG AAG ACT GTT CTC AAC ATG
        1713        1722        1731        1740        1749        1758

Val Asn Val Asn Phe Tyr Gly Pro Gly Met Thr Glu Gly Ala Leu Tyr Ser Lys Ala
GTG AAC GTG AAC TTC TAC GGG CCG GGC ATG ACC GAG GGT GCG CTG TAC AGT AAG GCT
        1770        1779        1788        1797        1806        1815
```

FIG. 1C

```
Arg Tyr Ser Asp Ile Ser Thr Leu Asn Ser Asn Val Arg Ala Ile Pro Tyr Thr Asn
CGC TAC TCG GAT ATC AGC ACG CTG AAC TCC AAC GTG CGT GCT ATC CCG TAC ACC AAC
        1827        1836        1845        1854        1863        1872

Ile Gln Gly Asn Val Gly Val Ile Leu Ser Pro Val Asn Arg Met Tyr Thr Leu Pro
ATC CAA GGT AAC GTG GGT GTC ATC CTG TCT CCG GTC AAC CGC ATG TAC ACG CTG CCG
        1884        1893        1902        1911        1920        1929

Asn Ala Leu Ala Thr Leu Asp Gly Asn Glu Phe Pro Thr Gly Lys Glu Phe Cys Glu
AAC GCC CTC GCT ACC CTT GAC GGT AAT GAG TTC CCC ACC GGG AAA GAG TTC TGC GAA
        1941        1950        1959        1968        1977        1986

Gly Thr Val Leu Phe Lys Thr Asp Gly Ser Gly Gly Asn Phe Ile Val Thr Arg Phe
GGT ACT GTG CTG TTC AAG ACC GAT GGC TCC GGT GGC AAC TTC ATC GTG ACC CGG TTC
        1998        2007        2016        2025        2034        2043

Gly Ala Tyr Ile Pro Asp Asp Gly Asn Asn Phe Lys Val Arg Ala Ala Ala Ala Gly
GGT GCG TAC ATC CCG GAT GAC GGT AAC AAC TTC AAG GTG CGT GCT GCT GCC GCT GGC
        2055        2064        2073        2082        2091        2100

Gln Thr Tyr Leu Glu Gln Asn Leu Thr Pro Ala Gly Thr Gln Ala Ser Thr Ser Trp
CAG ACG TAT CTG GAG CAG AAC CTG ACT CCG GCT GGT ACT CAG GCT TCC ACC TCG TGG
        2112        2121        2130        2139        2148        2157

Leu Tyr His Lys Pro Ile Ser Ala Gly Thr Arg Leu Asn Val Pro Gly Ala Gly Pro
CTG TAC CAT AAG CCA ATC TCT GCT GGT ACT CGA CTC AAT GTT CCG GGT GCC GGG CCG
        2169        2178        2187        2196        2205        2214

Ser Gly Gly Thr Leu Thr Val Thr Val Val Arg Ala Pro Tyr Gln Val Asp Asn Asn
AGC GGC GGT ACG CTC ACT GTG ACG GTG GTG CGT GCT CCG TAT CAG GTG GAC AAC AAC
        2226        2235        2244        2253        2262        2271

Ile Gly Asn Pro Val Arg Ile Asp Ile Thr Pro Ala Ile Val Thr Ala Ile Pro Ala
ATC GGA AAC CCG GTA CGC ATC GAC ATT ACC CCG GCC ATT GTG ACG GCA ATC CCT GCG
        2283        2292        2301        2310        2319        2328

Gly Thr Gln Leu Ala Ala Thr Tyr Pro Val Ala Try Ile TER
GGA ACG CAG CTC GCC GCT ACC TAC CCG GTG GCT TAC ATC TAA
        2340        2349        2358        2367
```

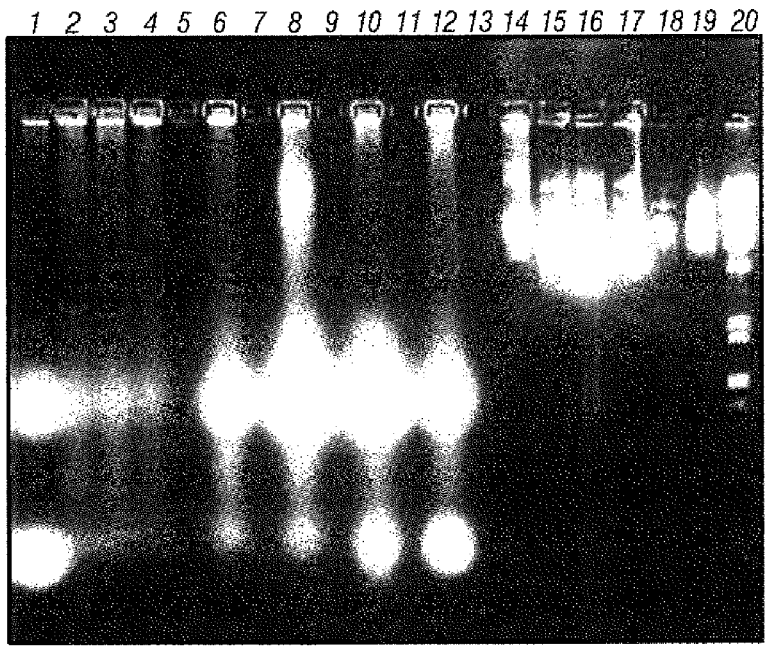

| Lane# | Sample |
|---|---|
| 1 | Laboratory Grade plasmid DNA, Prep A labeled with DTAF |
| 2 | GMP Grade DNA, Company #2 labeled with DTAF |
| 3 | GMP Grade DNA, Company #1 labeled with DTAF |
| 4 | Clinical Grade DNA, Company #1 labeled with DTAF |
| 5 | No Sample Loaded |
| 6 | Qiagen Endotoxin free DNA, Prep A Labeled with DTAF |
| 7 | No Sample Loaded |
| 8 | Detoxified LPS, Sigma, labeled with DTAF |
| 9 | No Sample Loaded |
| 10 | LPS, Sigma, labeled with DTAF |
| 11 | No Sample Loaded |
| 12 | Laboratory Grade plasmid DNA, Prep B labeled with DTAF |
| 13 | No Sample Loaded |
| 14 | Laboratory Grade plasmid DNA, Prep A labeled with EtBr |
| 15 | GMP Grade DNA, Company #2 labeled with EtBr |
| 16 | GMP Grade DNA, Company #1 labeled with EtBr |
| 17 | Clinical Grade DNA, Company #1 labeled with EtBr |
| 18 | Laboratory Grade plasmid DNA, Prep B labeled with EtBr |
| 19 | Qiagen Endotoxin free DNA, Prep A Labeled with EtBr |
| 20 | Mixture of high and low DNA molecular weight markers labeled with EtBr |

Fig. 3

SEQ ID NO: 1 - - CAE Full-length Protein Sequence

MANSYNAYVANGSQTAFLVTFEQRVFTEIQVYLNSELQTEGYTYNSVTKQIIFDTAPLAGVIVRLQRYTSEVLLNKFGQDAAFTGQNILDE
NFEQILFKAEETQEAWLAPLDRAVRVPNSEVSINALPNVAGRRNKALGFDSNGQPFMIPLVDIPDSALAIALAMADGGKWIGTLGGGTFL
DRQDTVCLSEFTNNTGYASVAAAVQACFDYAKANGKVVDARGWEGTVDSTVLMDGIEVVGGTWHGKADIRLLNSTFRNFVASTVRVA
YWGGEVRIADYEFTSAPSNSKVTSILFQGNIAGGSYVIENGIHRNGKFGILQQGTGEAITNGVIRGITMMDMQGDGIEMNVINKHYDGGL
LIENIFLENIDGTNAPIPLSNWGIGIGIAGQGPFGWDAAETQYAKNVTVRNVHAPRGVRQVVHFEVTRDSTCENVVANPDLSVSIGTGLT
AAGVITYGCKRMTIDGVVGEPMNTGATSPNDIRIVMLEWGANQAGAGGTPGAACPSFDMTVRNVQTRTGRFYAGVGSDDDNTNTYH
LENIHCYKMTLFGVATLLNMTNVTGVVFDAVGDDSSGGTSSNGLYPRKKTVLNMVNVNFYGPGMTEGALYSKARYSDISTLNSNVRAI
PYTNIQGNVGVILSPVNRMYTLPNALATLDGNEFPTGKEFCEGTVLFKTDGSGGNFIVTRFGAYIPDDGNNFKVRAAAGQTYLEQNLT
PAGTQASTSWLYHKPISAGTRLNVPGAGPSGGTLTVTVVRAPYQVDNNIGNPVRIDITPAIVTAIPAGTQLAATYPVAYI

Fig. 4

SEQ ID NO: 2 - - CAE Truncated Protein Sequence

LAPLDRAVRVPNSEVSINALPNVAGRRNKALGFDSNGQPFMIPLVDIPDSALAIALAMADGGKWIGTLGGGTFLDRQDTVCLSEFTNNT
GYASVAAAVQACFDYAKANGKVVDARGWEGTVDSTVLMDGIEVVGGTWHGKADIRLLNSTFRNFVASTVRVAYWGGEVRIADYEFTS
APSNSKVTSILFQGNIAGGSYVIENGIHRNGKFGILQQGTGEAITNGVIRGITMMDMQGDGIEMNVINKHYDGGLLIENIFLENIDGTNAPI
PLSNWGIGIGIAGQGPFGWDAAETQYAKNVTVRNVHAPRGVRQVVHFEVTRDSTCENVVANPDLSVSIGTGLTAAGVITYGCKRMTID
GVVGEPMNTGATSPNDIRIVMLEWGANQAGAGGTPGAACPSFDMTVRNVQTRTGRFYAGVGSDDDNTNTYHLENIHCYKMTLFGVA
TLLNMTNVTGVVFDAVGDDSSGGTSSNGLYPRKKTVLNMVNVNFYGPGMTEGALYSKARYSDISTLNSNVRAIPYTNIQGNVGVILSPV
NRMYTLPNALATLDGNEFPTGKEFCEGTVLFKTDGSGGNFIVTRFGAYIPDDGNNFKVRAAAAGQTYLEQNLTPAGTQASTSWLYHKP
ISAGTRLNVPGAGPSGGTLTVTVVRAPYQVDNNIGNPVRIDITPAIVTAIPAGTQLAATYPVAYI

Fig. 5

SEQ ID NO: 3 - - HIS-Tagged CAE Full-length Protein Sequence

MGHHHHHHMANSYNAYVANGSQTAFLVTFEQRVFTEIQVYLNSELQTEGYTYNSVTKQIIFDTAPLAGVIVRLQRYTSEVLLNKFGQDA
AFTGQNLDENFEQILFKAEETQEAWLAPLDRAVRVPNSEVSINALPNVAGRRNKALGFDSNGQPFMIPLVDIPDSALAIALAMADGGKWI
GTLGGGTFLDRQDTVCLSEFTNNTGYASVAAAVQACFDYAKANGKVVDARGWEGTVDSTVLMDGIEVVGGTWHGKADIRLLNSTFRN
FVASTVRVAYWGGEVRIADYEFTSAPSNSKVTSILFQGNIAGGSYVIENGIHRNGKFGILQQGTGEAITNGVIRGITMMDMQGDGIEMNV
INKHYDGGLLIENIFLENIDGTNAPIPLSNWGIGIGIAGQGPFGWDAAETQYAKNVTVRNVHAPRGVRQVHFEVTRDSTCENVANPDL
SVSIGTGLTAAGVITYGCKRMTIDGVVGEPMNTGATSPNDIRIVMLEWGANQAGAGGTPGAACPSFDMTVRNVQTRTGRFYAGVGSD
DDNTNTYHLENIHCYKMTLFGVATLLNMTNVTGVVFDAVGDDSSGGTSSNGLYPRKKTVLNMVNVNFYGPGMTEGALYSKARYSDIST
LNSNVRAIPYTNIQGNVGVILSPVNRMYTLPNALATLDGNEFPTGKEFCEGTVLFKTDGSGGNFIVTRFGAYIPDDGNNFKVRAAAAGQ
TYLEQNLTPAGTQASTSWLYHKPISAGTRLNVPGAGPSGGTLTVTVVRAPYQVDNNIGNPVRIDITPAIVTAIPAGTQLAATYPVAYI

Fig. 6

SEQ ID NO: 4 -- HIS-Tagged CAE Truncated Protein Sequence

MGHHHHHHLAPLDRAVRVPNSEVSINALPNVAGRRNKALGFDSNGQPFMIPLVDIPDSALAIALAMADGGKWIGTLGGGTFLDRQDTV
CLSEFTNNTGYASVAAAVQACFDYAKANGKVVDARGWEGTVDSTVLMDGIEVVGGTWHGKADIRLLNSTFRNFVASTVRVAYWGGE
VRIADYEFTSAPSNSKVTSILFQGNIAGGSYVIENGIHRNGKFGILQQGTGEAITNGVIRGITMMDMQGDGIEMNVINKHYDGGLLIENIFL
ENIDGTNAPIPLSNWGIGIGIAGQGPFGWDAAETQYAKNVTVRNVHAPRGVRQVVHFEVTRDSTCENVVANPDLSVSIGTGLTAAGVIT
YGCKRMTIDGVVGEPMNTGATSPNDIRIVMLEWGANQAGAGGTPGAACPSFDMTVRNVQTRTGRFYAGVGSDDDNTNTYHLENIHC
YKMTLFGVATLLNMTNVTGVVFDAVGDDSSGGTSSNGLYPRKKTVLNMVNVNFYGPGMTEGALYSKARYSDISTLNSNVRAIPYTNIQ
GNVGVILSPVNRMYTLPNALATLDGNEFPTGKEFCEGTVLFKTDGSGGNFIVTRFGAYIPDDGNNFKVRAAAGQTYLEQNLTPAGTQ
ASTSWLYHKPISAGTRLNVPGAGPSGGTLTVTVVRAPYQVDNNIGNPVRIDITPAIVTAIPAGTQLAATYPVAYI

Fig. 7

SEQ ID NO: 5 -- FLAG®-Tagged CAE Full-length Protein Sequence

MANSYNAYVANGSQTAFLVTFEQRVFTEIQVYLNSELQTEGYTYNSVTKQIIFDTAPLAGVIVRLQRYTSEVLLNKFGQDAAFTGQNLDE
NFEQILFKAEETQEAWLAPLDRAVRVPNSEVSINALPNVAGRRNKALGFDSNGQPFMIPLVDIPDSALAIALAMADGGKWIGTLGGGTFL
DRQDTVCLSEFTNNTGYASVAAAVQACFDYAKANGKVVDARGWEGTVDSTVLMDGIEVVGGTWHGKADIRLLNSTFRNFVASTVRVA
YWGGEVRIADYEFTSAPSNSKVTSILFQGNIAGSSYVIENGIHRNGKFGILQQGTGEAITNGVIRGITMMDMQGDGIEMNVINKHYDGGL
LIENIFLENIDGTNAPIPLSNWGIGIGIAGQGPFGWDAAETQYAKNVTVRNVHAPRGVRQVVHFEVTRDSTCENVVANPDLSVSIGTGLT
AAGVITYGCKRMTIDGVVGEPMNTGATSPNDIRIVMLEWGANQAGAGGTPGAACPSFDMTVRNVQTRTGRFYAGVGSDDDNTNTYH
LENIHCYKMTLFGVATLLNMTNVTGVVFDAVGDDSSGGTSSNGLYPRKKTVLNMVNVNFYGPGMTEGALYSKARYSDISTLNSNVRAI
PYTNIQGNVGVILSPVNRMYTLPNALATLDGNEFPTGKEFCEGTVLFKTDGSGGNFIVTRFGAYIPDDGNNFKVRAAAAGQTYLEQNLT
PAGTQASTSWLYHKPISAGTRLNVPGAGPSGGTLTVTVVRAPYQVDNNIGNPVRIDITPAIVTAIPAGTQLAATYPVAYIDYKDDDDK

Fig. 8

SEQ ID NO: 6 - - FLAG®-Tagged CAE Truncated Protein Sequence

LAPLDRAVRVPNSEVSINALPNVAGRRNKALGFDSNGQPFMIPLVDIPDSALAIALAMADGGKWIGTLGGGTFLDRQDTVCLSEFTNNT
GYASVAAAVQACFDYAKANGKVVDARGWEGTVDSTVLMDGIEVVGGTWHGKADIRLLNSTFRNFVASTVRVAYWGGEVRIADYEFTS
APSNSKVTSILFQGNIAGGSYVIENGIHRNGKFGILQQGTGEAITNGVIRGITMMDMQGDGIEMNVINKHYDGGLLIENIFLENIDGTNAPI
PLSNWGIGIGIAGQGPFGWDAAETQYAKNVTVRNVHAPRGVRQVVHFEVTRDSTCENVVANPDLSVSIGTGLTAAGVITYGCKRMTID
GVVGEPMNTGATSPNDIRIVMILEWGANQAGAGGTPGAACPSFDMTVRNVQTRTGRFYAGVGSDDDNTNTYHLENIHCYKMTLFGVA
TLLNMTNVTGVVFDAVGDDSSGGTSSNGLYPRKKTVLNMVNVNFYGPGMTEGALYSKARYSDISTLNSNVRAIPYTNIQGNVGVILSPV
NRMYTLPNALATLDGNEFPTGKEFCEGTVLFKTDGSGGNFIVTRFGAYIPDDGNNFKVRAAAAGQTYLEQNLTPAGTQASTSWLYHKP
ISAGTRLNVPGAGPSGGTLTVTVRAPYQVDNNIGNPVRIDITPAIVTAIPAGTQLAATYPVAYIDYKDDDDK

Fig. 9

SEQ ID NO: 7 - - CAE Full-Length DNA Coding Sequence

ATGGGCGAACA GCTATAAATGC TTACGTGGCG AACGGTTCAC AGACCGCATT CCTCGTCACG TTCGAGCAGC GCGTGTTCAC
TGAGATTCAG GTGTACCTCA ACTCCGAACT CCAGACGGAA GGGTACACCT ACAACTCTGT GACCAAACAG ATTATCTTCG
ACACCGCCCC GCTCGCCGGG GTGATTGTCC GACTCCAACG CTACACCTCT GAGGTTCTGC TGAACAAGTT GGCCAAGAC
GCTGCCTTCA CCGGGCAGAA CCTTGACGAG AACTTTGAGC AGATTCTGTT CAAGGCTGAG GAAACTCAGG AAGCATGGCT
CGCGCCCACTT GACCGCGCCG TCCGTGTTCC AGCCGTTCAT GTCTCCATCA ACGCATTACC GAACGTCGCT GCCGCCGCA
ACAAGGCACT GGGCTTTGAC AGCAATGGTC AGCCGTTCAT GATTCCTCTG GTCGATATCC CGGACTCCGC GCTGGCGATT
GCTCTGGCAA TGGCTGACGG CGGTAAGTGG ATTGGTACTC TCGGCGGGGG CACGTTCCTC GACCGTCAGG ATACCGTCTG
CCTGTCCGAG TTCACCAACA ACACTGGGTA CGCCTCTGTC GCCGCTGCGG TGCAGGCTTG CTCGACTAT GCGAAGCCA
ACGGCAAGGT CGTTGACGCT CGCGGCTGGG AAGGTACGGT GGATTCCACT GTGCTGATGG ACGTATTGA GGTCGTCGGC
GGTACGTGGC ACGGCAAGGC TGACATTCGC CTGTGAACT CCACCTTCCG CAACTTCGTG GCCTCTACTG TCCGTGTCGC
CTACTGGGGC GGCGAGGTGC GTATTGCTGA CTATGAGTTC ACCAGCGCAC CGAGCAACTC CAAGGTTACG TCTATCCTGT
TCCAAGGCAA CATCGCCGGG GGCAGCTACG TCATTGAGAA CGGTATCCAC CGCAATGGTA AGTTCGGTAT TCTCCAACAG
GGTACTGGCG AGCTATCAC CAACGGCGTT ATCCGTGGCA TCACCATGAT GGATATGCAG GGTGACGGTA TCGAGATGAA
CGTAATCAAC AAGCACTATG ATGGTGGCCT GCTGATTGAG AACATCTTCC TTGAGAACAT CGACGGCACC AACGCGCTA
TCCCACTGTC CAACTGGGGC ATTGGTATCG GTATCCGTGG TCAAGGCCCG TTCGGTTGGG ATGCTGCTGA GACGCAGTAT
GCGAAGAACG TCACTGTCCG TAACGTCCAT GCTCCGCGTG CCAACCCTGA CCTGTCCGTC TCCATTGGTA CTGGCCCTGA GGTCGTCAC TTCGAGGTTA CGCGTGACAG
CACCTGCGAG AACGTAGTGG CCAACCCTGA CCTGTCCGTC TCCATTGGTA CTGGCCCTGA CCTCTCCGAA CGATATTCGT
ACGGCTGCAA GCGCATGACC ATTGACGGTG TAGTCGGTGA GCCTATGAAC ACCGGAGCAA CCTCTCCGAA CGATATTCGT
ATCGTGATGT TGGAGTGGGG TGCGAACCAA GCAGGTGCTG GCGGTACGCC GGGTGCAGCT TGCCATCGT TGACATGAC
CGTGCGTAAC GTGCAGACCC GTACCGGGGCG CTTCTATGCT GGTGTCGGCT CCGACGATGA CAACACCAAC ACATACAC
TTGAAAAACAT TCACTGTTAC AAGATGACGC TGTTTGGTGT GGCAACTCTG CTGAACATGA CCAACGTGAC TGGTGTGGTG
TTCGACGCTG TAGGCGATGA CTCCAGCGGC GGTACGTCC CCAACGTCT GTACCCGCGT AAGAAGACTG TTCTCAACAT
GGTGAACGTG AACTTCTACG GGCCGGGCAT GACCGAGGGT GCGCTGTACA GTAAGGCTCG CTACTCGGAT ATCAGCACGC
TGAACTCCAA CGTGCGTGCT ATCCCGTACA CCAACATCCA AGTTAACGTG GGTGTCATCC TGTCTCCGGT CAACCGCATG
TACACGCTGC CGAACGCCCT CGTACCCCTT GACGTAATG AGTTCCCCAC CGGGAAAGAG TTCTGCGAAG GTACTGTGCT
GTTCAAGACC GATGGCTCCG GTGGCAACTT CATCGTGACC CGGTTCGGTG CGTACATCCC GGATGACGGT AACAACTTCA
AGGTGCGTGC TGCTGCCGCT GGCCAGACGT ATCTGGAGCA GAACCTGACT CCGGCTGGTA CTCAGGCTTC CACCTCGTGG
CTGTACCATA AGCCAATCTC TGCTGGTACT CGACTCAATG TTCCGGGTGC CGGGCCGAGC GCGGTACGC TCACTGTGAC
GGTGGTGCGT GCTCCGTATC AGTGGACAA CAACATCGGA AACCCGGTAC GCATGACAT TACCCCGGCC ATTGTGACGG
CAATCCCTGC GGGAACGCAG CTCGCCGCTA CCTACCCGGT GGCTTACATC TAA

Fig. 10

SEQ ID NO: 8 -- CAE Truncated DNA Coding Sequence

```
CTCGCGCCAC TTGACCGCGC CGTCCGTGTT CCGAACTCCG AAGTCTCCAT CAACGCATTA CCGAACGTCG CTGCCGCCCG
CAACAAGGCA CTGGGCTTTG ACAGCAATGG TCAGCCGTTC ATGATCCCTC TGGTCGATAT CCCGGACTCC GCGCTGGCGA
TTGCTCTGGC AATGCTGAC GGGGTAAGT TCAGACGTTCC TCTCGGCGGG GGCACGTTCC TGACCGTCA GGATACCGTC
TGCCTGTCCG AGTTCACCAA CAACACTGGG TACGCCCTG TCGCCGCTGC GGTGCAGGCT TGCTTCGACT ATGCGAAAGC
CAACGGCAAG GTCGTTGACG CTCGCGGCTG GGAAGGTACG GTGGATTCCA CTGTGCTGAT GGACGGTATT GAGGTCGTCG
GCGGTACGTG GCACGGCAAG GCTGACATTC GCCTGCTGAA CTCCACCTTC CGCAACTTCG TGGCCTCTAC TGTCCGTGTC
GCCTACTGGG GCGGCGAGGT GCGTATTGCT GACTATGAGT TCACCAGCGC ACCGAGCAAC TCCAAGGTA CGTCTATCCT
GTTCCAAGGC AACATCGCCG GGGCAGCTA CGTCATTGAG AACGGTATCC ACCGGAATGG TAAGTTCGGT ATTCTCCAAC
AGGGTACTGG CGAGGCTATC ACCAACGGCG TTATCCGTGG CATCACCATG AGGTATATGC AGGGTGACGG TATCGAGATG
AACGTAATCA ACAAGCACTA TGATGGTGCC CTGCTATTCG AGAACATCTT CCTTGAGAAC ATCGACGGCA CCAACGGCC
TATCCCACTG TCCAACTGGG GCATTGGTAT CGGTATCGCT GGTCAAGGCC CGTTCGGTTG GGATGCTGCT GAGACGCAGT
ATGCGAAGAA CGTCACTGTC CGTAACGTCC ATGCCCGCG GTCAAGCCT GACCGTCCG TCTCCATTGG TACTGGCCTG ACTGCCGCTG GTGTAATCAC
AGCACCTGCG AGAACGTAGT GGCCAACCCT GACCGTCCG TCTCCATTGG TACTGGCCTG ACTGCCGCTG GTGTAATCAC
GTACGGCTGC AAGCGACATGA CCATTGACGG TGTAGTCGT GAGCCTATGA ACACCGGAGC AACCTCTCCG AACGATATTC
GTATCGTGAT GTGGAGTGG GGTGCGAACC AAGCAGGTGC TGGCGGTACG CCGGGTACG CTTGCCCATC GTTCGACATG
ACCGTGCGTA AGTGCAGAC CCGTACCGGG CGCTTCTATG CTGTGTCGG CTCCGACGAT GACAACACCA ACACATCA
CCTTGAAAAC ATTCACTGTT ACAAGATGAC GCTGTTTGGT GTGGCAACTC TGCTGAACGT GACCAACGTG ACTGGTGTGG
TGTTCGACGC TGTAGGCGAT GACTCCAGCG GCGGTACGTC CTCCAACGGT CTGAACGGT GTAAGAAGAC TGTTCTCAAC
ATGGTGAACG TGAACTTCTA CGGGCCGGGC ATGACCGGGC GTGCGCTGTA CAGTAAGGCT CGCTACTCGG ATATCAGCAC
GCTGAACTCC AACGTGCGTG CTATCCGTG CACCAACATC CAAGGTAACG TGGGTGTCAT CCTGTCTCCG GTCAACCGCA
TGTACACGCT GCCGAACGCC CTCGGTGGCC TTGACGGTAA TGAGTTCCCC ACCGGGAAAG AGTTCTGCGA AGGTACTGTG
CTGTTCAAGA CCGATGCCTC CGGTGGCAAC TTCATCGTGA CCGGTTCGG TGCGTACATC CCGGATGACG GTAACAACTT
CAAGGTGCGT GCTGCTGCCG CTGGCCAGAG CTATCTGGAG CAGAACCTGA TGTTCCGGGT GCCGGGCCGA GGGCGGTAC GCTCACTGTG
GGCTGTACCA TAAGCCAATC TCTGCTGGTA CTCGACTCAA ACAACATCG GAAACCCGGT ACGCATGGAC GCTCACTGTG
ACGTGGGTGC GTGCTCCGTA TCAGGTGGAC AACAACATCG GAAACCCGGT ACGCATGGAC ATTACCCGCG
GGCAATCCCT GCGGAACGC AGCTCGCCGC TACCTACCCG GTGGCTTACA TCTAA
```

Fig. 11

SEQ ID NO: 9 - - CAE Fragment

ANSYNAYVANGSQTA

SEQ ID NO: 10 - - CAE Fragment

LLEQGTGEALTDGVLR

SEQ ID NO: 11 - - CAE Fragment

VPNSEVSLNALPNVQR

SEQ ID NO: 12 - - CAE Fragment

LADYEFTSAPSNSK

SEQ ID NO: 13 - - CAE Fragment

YSDLSTLN

SEQ ID NO: 14 - - CAE Fragment

QLLFDTAPLA

SEQ ID NO: 15 - - CAE Fragment

APYQVDDNL

SEQ ID NO: 16 - - CAE Fragment

FGAYLPDD

SEQ ID NO: 17 - - CAE Fragment

LGTLGG

Fig. 12

TOXICITY MEASUREMENTS *

| DNA Type | DNA Amount | # of Mice Injected | # of Dead Mice at 18 hours Post-Injection | # of Dead Mice at 1 Week Post-Injection |
| --- | --- | --- | --- | --- |
| Super Clean | 100 µg | 10 | 0 | 0 |
| Super Clean | 50 µg | 10 | 0 | 0 |
| Qiagen EndoFree | 100 µg | 10 | 10 | N/A |
| Qiagen EndoFree | 50 µg | 10 | 0 | 0 |

* Experiments performed in Balb/c mice using PDX-1 shRNA Super Clean DNA versus PDX-1 shRNA Qiagen EndoFree DNA

Fig. 13

TOXICITY MEASUREMENTS *

| DNA Type | DNA Amount | # of Mice Injected | # of Dead Mice at 18 hours Post-Injection | # of Dead Mice at 3 Weeks Post-Injection |
|---|---|---|---|---|
| Super Clean | 100 μg | 20 | 0 | 0 |
| Super Clean | 40 μg | 20 | 0 | 0 |
| Qiagen EndoFree | 100 μg | 5 | 5 | N/A |
| Qiagen EndoFree | 40 μg | 5 | 5 | N/A |

* Experiments performed in SCID mice using the CAE enzyme method for Super Clean DNA production

Fig. 14

TOXICITY MEASUREMENTS *

| DNA Type | DNA Amount | # of Mice Injected | # of Dead Mice at 18 hours Post-Injection | # of Dead Mice at 3 Weeks Post-Injection |
|---|---|---|---|---|
| Super Clean | 100 µg | 60 | 0 | 0 |
| Qiagen EndoFree | 100 µg | 5 | 5 | N/A |

* Experiments performed in PANC-1 tumor-bearing SCID mice using the CAE enzyme method for Super Clean DNA production

POLYPEPTIDES HAVING COLANIC ACID-DEGRADING ACTIVITY

CROSS-REFERENCE TO RELATED APPLICATIONS

The present invention claims the benefit of U.S. Provisional Application Ser. No. 61/125,916, filed on Apr. 30, 2008; Ser. No. 61/125,923, filed on Apr. 30, 2008, and is a continuation of U.S. patent application Ser. No. 12/433,691, filed Apr. 30, 2009, each of which is hereby incorporated by reference in its entirety.

FIELD OF THE INVENTION

The present disclosure generally relates to polypeptides having colanic acid-degrading activity and methods of using the same. Polynucleotides encoding such polypeptides are also described. The polypeptides may be used, for example, in processes for degrading colanic acid, processes for the removal of endotoxins from biological samples, and processes for purifying plasmid DNA.

BACKGROUND

A key step for any application in which nucleic acid is introduced into an organism is the need to produce highly purified, often pharmaceutical grade, nucleic acid. Such purified nucleic acid must meet drug quality standards of safety, potency and efficacy. In addition, it is desirable to have a scaleable process that can be used to produce multi-gram quantities of DNA. Thus, it is desirable to have a process for producing highly pure nucleic acid that does not require toxic chemicals, mutagens, organic solvents, or other reagents that would compromise the safety or efficacy of the resulting nucleic acid, or make scale-up difficult or impractical. It is also desirable to prepare nucleic acids free from contaminating endotoxins, which if administered to a patient could elicit a toxic response. Removal of contaminating endotoxins is particularly important, for example, where plasmid DNA is purified from gram negative (−) bacterial sources that have high levels of endotoxins and colanic acid as an integral component of the outer cell membrane.

Plasmids are self-replicating genetic elements that reside and multiply in host bacteria. Basically, all molecular genetic methods involving the manipulation of specific DNA fragments utilize plasmid DNA to produce large amounts of the specific DNA fragment (or protein/RNA derived from said fragment).

The choice of bacterial hosts, or sources of the plasmids, generally reflects a historical perspective. Stanley Cohen and Herb Bayer chose *Escherichia coli* (*E. coli*) strain K-12 for their groundbreaking molecular genetic experiments in the early 1970s because it was easy to grow and amenable to metabolic studies. These same properties also made *E. coli* K-12 the primary microorganism for bacterial geneticists to study. Molecular geneticists now use this same strain of *E. coli* for routine procedures because it turned out to be an extremely good host for a variety of molecular genetic applications. Moreover, during the past 25 years, *E. coli* K-12 has proved to be an innocuous biological host for the propagation of recombinant DNA molecules. The attenuated *E. coli* K-12 strain does not thrive outside of the laboratory environment and it is unable to compete against the more genetically robust *E. coli* serotypes normally found in the human intestine.

Among other techniques, currently available methods for separation and purification of plasmid DNA utilize ion exchange chromatography (Duarte et al., Journal of Chromatography A, 606 (1998), 31-45) and size exclusion chromatography (Prazeres, D. M., Biotechnology Techniques Vol. 1, No. 6, June 1997, p 417-420), coupled with the use of additives such as polyethylene glycol (PEG), detergents, and other components such as hexamine cobalt, spermidine, and polyvinylpyrollidone (PVP). Additional methods of separating DNA from contaminants rely on size-exclusion chromatography, which involves separation of the nucleic acid from endotoxins and other contaminants based on the small difference in size. These methods are generally acceptable, but may be unable to provide an efficient and cost effective separation of nucleic acids (e.g., DNA, including supercoiled and/or nicked (or relaxed)) at the desired level of purity.

Also, plasmid DNA preparations, which are produced from bacterial preparations and often contain a mixture of relaxed and supercoiled plasmid DNA, frequently require endotoxin removal, as required by the FDA, as endotoxins produced by many bacterial hosts are known to cause inflammatory reactions, such as fever or sepsis, or in some cases death, in the host receiving the plasmid DNA. These endotoxins are generally lipopolysaccharides, or fragments thereof, that are components of the outer membrane of gram negative (−) bacteria, and are present in the DNA preparation of the host cells and host cell membranes or macromolecules. Hence, removal of endotoxins can be a key step in the purification of plasmid DNA for therapeutic or prophylactic use. Endotoxin removal from plasmid DNA solutions primarily uses the negatively charged structure of the endotoxins. Plasmid DNA, however, also is negatively charged and thus separation is frequently achieved with anion exchange resins which bind both these molecules and, under certain conditions, preferentially elute plasmid DNA while binding the endotoxins. Such a separation results in only partial removal as significant amounts of endotoxins elute with the plasmid DNA and/or a very poor recovery of plasmid DNA is achieved.

Small- and large-scale isolation and purification of plasmid DNA from small or large volume microbial fermentations thus requires the development of an improved plasmid preparation process. It is also desirable for plasmid-based research and therapy, that the nucleic acids can be separated and purified keeping the same structure in a reproducible manner, and in order to avoid the adverse effect of impurities on mammalian body, the nucleic acids are required to have been separated and purified up to high purity.

Plasmid DNA used for gene therapy is typically isolated from *E. coli* K-12. Endotoxins, also known as lipopolysaccharides (LPS), are known to be prominent cell membrane components of gram-negative bacteria such as *E. coli*. In fact, some reports suggest that the lipid portion of the outer membrane of *E. coli* is completely composed of endotoxin molecules. (*Qiagen Plasmid Purification Handbook*, July 1999).

LPS contains a hydrophobic lipid A moiety, a complex array of sugar residues and negatively charged phosphate groups. The lipid A moiety of LPS has demonstrated endotoxin activity and elicits a strong, potentially life-threatening inflammatory response in mammals. This inflammatory response is characterized by fever, decreased blood pressure, local inflammation, and septic shock. Lipid A induces this response by binding to serum lipopolysaccharide-binding protein (LBP) and triggering signaling through the CD14 receptor expressed on monocytes, endothelial cells, and polymorphonuclear leukocytes (Ingalls, R. R. et al. 1998. *J. Immunol.* 161:5413-5420). Endotoxin is extremely lethal when injected into mice, causing death within an hour of injection. Endotoxin is also known to drastically reduce transfection efficiencies in cells (Weber, M., et al. 1995. *Biotechniques* 19:930-940). Thus, the importance of using endotoxin-free plasmid DNA for gene therapy applications has long been emphasized.

A number of scientists have worked to remove LPS and other endotoxins from DNA samples in an effort to reduce the toxicity of DNA samples used in gene therapy. However, recent evidence has indicated that DNA samples with negligible amounts of LPS are still toxic when administered in significant quantities. Thus, additional toxic components of DNA samples must be identified and removed to ensure the safety of DNA preparations used clinically.

The chemical structure and properties of endotoxin molecules and their tendency to form micellar structures initially led to the copurification of LPS and plasmid DNA. For example, DNA is often copurified with LPS in CsCl ultracentrifugation procedures because the LPS and the plasmid DNA have a similar density in CsCl. In addition, micellar LPS separates on size exclusion resins with large DNA molecules. Likewise, the negative charges present on LPS molecules interacts with anion-exchange resins in a manner that leads to their copurification with DNA on anion-exchange resins.

Cell wall polysaccharides have been reported to contaminate DNA isolated from a variety of sources including bacteria, yeast, plants, blue-green algae, protozoa, fungi, insects, and mammals (Edelman, M. 1975. *Anal. Biochem.* 65:293-297; Do, N. and Adams, R. P. 1991. *Biotechniques* 10:162-166; Chan, J. W. and Goodwin, P. H. 1995. *Biotechniques* 18:419-422).

Plant polysaccharides that contaminate plant genomic DNA are reported to inhibit both restriction endonuclease treatments and the polymerase chain reaction (Robbins, M. et al. 1995. *Benchmarks* 18: 419-422). Furthermore, polysaccharides purified from the slime *Physarum polycephalum* have been reported to inhibit DNA polymerase activity (Shioda, M. and K. Murakami-Murofushi. 1987. *Biochem. Biophys. Res. Commun.* 146:61-66) and the acid polysaccharides from sea urchin embryos are known to inhibit RNA polymerase activity (Aoki, Y. and H. Koshihara. 1972. *Biochim. Biophys. Acta* 272:33-43).

There are several methods for purifying plasmid DNA described in the literature, but these methods generally only remove a portion of the polysaccharides, if at all. For example, the Lipid A purification methods are based on the hydrophobic properties of Lipid A. Thus, these methods remove Lipid A and the polysaccharides that are covalently linked to Lipid A. However, since only a small fraction of the capsular polysaccharides of *E. coli* are covalently linked to Lipid A only a few of them are removed during the standard preparation and purification procedures of plasmid DNA (Jann, B. and K. Jann. 1990. *Curr. Top. Microbiol. Immunol.* 150:19-42; Wicken, A. J. 1985. In: *Bacterial Adhesion*, D. M. Pletcher (ed.), Plenum Press: New York, pp. 45-70). Some of the *E. coli* capsular polysaccharides have phosphatidic acid as a lipid moiety; however, the phosphatidic acid is typically hydrolyzed during the standard plasmid isolation procedures. Thus, these polysaccharides are not removed from DNA by the currently used methods that deplete endotoxin based on hydrophobicity (i.e., the presence of Lipid A binding).

Several methods have been developed to reduce levels of endotoxin-positive LPS in DNA isolated from *E. coli* (Neudecker, F. and S. Grimm. 2000. *Biotechniques* 28:107-110), including several commercially available kits (Qiagen, Inc., Valencia, Calif.; Sigma Chemical Co., Inc., St. Louis, Mo.). DNA purified using the Qiagen kit is generally considered to be the "gold standard" of clean plasmid DNA. Not only is the Qiagen kit designed to remove LPS, but it also includes RNase to digest the RNA in plasmid DNA preparations. In fact, most of the DNA purification methods include an RNase digestion step. However, one is limited to the amount of RNase that can be added to the plasmid DNA, since high quantities of RNase will begin to digest DNA.

It is difficult to separate polysaccharides from DNA using current standard purification procedures. Both DNA and polysaccharides are precipitated by organic solvents such as ethanol and polyethylene glycol (PEG). Since polysaccharides are anionic, the polysaccharides co-purify with DNA using anion exchange resins. Furthermore, the high molecular weight polysaccharides and plasmid DNA have a similar density in CsCl.

Affinity chromatography has been proposed for removal of polysaccharide contaminants from DNA. For example, an early paper reported purification of DNA from a variety of sources, including plants, insects, fungi, and algae using affinity chromatography where deproteinized DNA fractions are passed through a column of concanavalin A linked to Sepharose (Edelman, M. 1975. *Anal. Biochem.* 65:293-29). Unfortunately, *E. coli* polysaccharides generally do not contain the sugars that bind to concanavalin A. Similarly, lectin affinity chromatography has been reported to be useful for removing polysaccharide contaminants from DNA isolated from fungi and plants (Do, N. and R. P. Adams. 1991. *Biotechniques* 10:162-166); but the sugars recognized by lectin are not present in most polysaccharides from organisms such as *E. coli*.

A salt wash of gram-negative bacterial pellets has also been proposed as a method of purifying bacterial genomic DNA (Cahn, J. W. and P. H. Goodwin. 1995. Biotechniques 18:519-422). Salt washing was suggested as a way to improve purification of DNA because of the interference the polysaccharides present in DNA caused with restriction enzyme digestion. None of these methods, however, successfully removed all polysaccharides found in plasmid DNA.

WO 95/20594 and U.S. Pat. No. 5,969,129 describe a method for batch purification of genomic DNA, from corn and other plants. This purification process used polymer gels containing boronate groups to isolate DNA from DNA/polysaccharide mixtures.

Although, the entire emphasis of clinicians in preparing "clean" DNA for clinical use has centered on the removal of LPS, recent reports indicate that "LPS-free" DNA still exhibits toxicity in high dosages. For example, scientists have observed toxicity leading to the death of mice following intravenous injection of DNA-liposome complexes containing 50-300 mg of DNA and reduced quantities of LPS, whereas the injection of equal concentrations of liposomes has no toxic effect. It has also been observed that gene expression is reduced after transfection using DNA with reduced quantities of LPS. Recent reports further suggest that inflammation and significant immune responses are produced after the intramuscular injection of supposedly pure DNA (Fields, P. A. et al. 2000. *Molec. Therap.* 1:225-235). Therefore, even DNA that is thought to be pure, of clinical grade, and with low levels of LPS, produces toxic responses in animals.

SUMMARY OF THE INVENTION

Among the various aspects of the present invention is the provision of polypeptides having colanic acid-degrading activity. These polypeptides are useful in preparing highly pure plasmid DNA preparations, and are also useful in processes for degrading colanic acid.

Briefly, therefore, the present invention is directed to a polypeptide having at least 90% homology to SEQ ID NO: 1, and conservative amino acid substitutions thereof. In one embodiment, the polypeptide has at least 95% homology to SEQ ID NO: 1, and conservative amino acid substitutions thereof. In another embodiment, the polypeptide has the amino acid sequence of SEQ ID NO: 1.

Another aspect of the invention is directed to a polypeptide having at least 90% homology to SEQ ID NO: 2, and conservative amino acid substitutions thereof. In one embodiment, the polypeptide has at least 95% homology to SEQ ID NO: 2, and conservative amino acid substitutions thereof. In another embodiment, the polypeptide has the amino acid sequence of SEQ ID NO: 2.

Another aspect of the invention is directed to an isolated polynucleotide comprising a nucleic acid sequence that shares at least 90% sequence identity with SEQ ID NO: 7, or the complement thereof. In one embodiment, the nucleic acid sequence shares at least 95% sequence identity with SEQ ID NO: 7, or the complement thereof. In another embodiment, the polynucleotide has the nucleic acid sequence of SEQ ID NO: 7.

Another aspect of the invention is directed to an isolated polynucleotide comprising a nucleic acid sequence that shares at least 90% sequence identity with SEQ ID NO: 8, or the complement thereof. In one embodiment, the nucleic acid sequence shares at least 95% sequence identity with SEQ ID NO: 8, or the complement thereof. In another embodiment, the polynucleotide has the nucleic acid sequence of SEQ ID NO: 8.

Other aspects of the invention are directed to a vector comprising a polynucleotide, wherein the vector is selected from the group consisting of a plasmid, a virus, and a bacteriophage. In one aspect, the polynucleotide shares at least 90% sequence identity with SEQ ID NO: 7, or the complement thereof. In another aspect, the polynucleotide shares at least 90% sequence identity with SEQ ID NO: 8, or the complement thereof. In one embodiment of either aspect, the vector is a plasmid or a bacteriophage. In a preferred embodiment of either aspect, the vector is a bacteriophage.

Other aspects and features will be in part apparent and in part pointed out hereinafter.

The foregoing has outlined rather broadly several aspects of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed might be readily utilized as a basis for modifying or redesigning the composition and method for carrying out the same purposes as the invention. It should be realized by those skilled in the art that such modified or redesigned compositions and methods do not depart from the spirit and scope of the invention as set forth in the appended claims

BRIEF DESCRIPTION OF THE DRAWINGS

FIGS. 1A, 1B, 1C, and 1D shows the nucleotide and amino acid sequence of a colanic acid-degrading enzyme according to one embodiment.

FIG. 2 shows a gel where several different DNA plasmid samples were tested using this gel electrophoretic method for polysaccharide visualization and quantification.

FIGS. 3-8 show the polypeptide sequences of SEQ ID NOS: 1-6.

FIGS. 9-10 show the polynucleotide sequences of SEQ ID NO: 7 and SEQ ID NO: 8.

FIG. 11 shows the polypeptide sequences of SEQ ID NOS: 9-17.

FIGS. 12-14 show tables of results from post-iv injections of 120 mice with high doses of DNA-BIV liposomal complexes, purified according to the processes described herein.

ABBREVIATIONS AND DEFINITIONS

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

The term "analog" refers to a molecule which is structurally similar or shares similar or corresponding attributes with another molecule (e.g. a CAE-related protein). For example an analog of a CAE protein can be specifically bound by an antibody or T cell that specifically binds to CAE.

The term "antibody" is used in the broadest sense. Therefore an "antibody" can be naturally occurring or man-made such as monoclonal antibodies produced by conventional hybridoma technology. Anti-CAE antibodies comprise monoclonal and polyclonal antibodies as well as fragments containing the antigen-binding domain and/or one or more complementarity determining regions of these antibodies. An "antibody fragment" is defined as at least a portion of the variable region of the immunoglobulin molecule that binds to its target, i.e., the antigen-binding region. In one embodiment it specifically covers single anti-CAE antibodies and clones thereof (including agonist, antagonist and neutralizing antibodies) and anti-CAE antibody compositions with polyepitopic specificity.

The term "homolog" refers to a molecule which exhibits homology to another molecule, by for example, having sequences of chemical residues that are the same or similar at corresponding positions.

The terms "hybridize", "hybridizing", "hybridizes" and the like, used in the context of nucleic acids, are meant to refer to conventional hybridization conditions, preferably such as hybridization in 50% formamide/6×SSC/0.1% SDS/100 µg/ml ssDNA, in which temperatures for hybridization are above 37° C. and temperatures for washing in 0.1×SSC/0.1% SDS are above 55° C.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a nucleic acid or polynucleotide is said to be "isolated" when it is substantially separated from contaminant polynucleotides that correspond or are complementary to genes other than the target genes or that encode polypeptides other than the target gene product or fragments thereof. A skilled artisan can readily employ nucleic acid isolation procedures to obtain an isolated polynucleotide. A protein is said to be "isolated," for example, when physical, mechanical or chemical methods are employed to remove the target proteins or polypeptides from cellular constituents that are normally associated with the protein. A skilled artisan can readily employ standard purification methods to obtain an isolated protein. Alternatively, an isolated protein can be prepared by chemical means.

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The term "monoclonal antibody" refers to a collection of antibodies encoded by the same nucleic acid molecule which are optionally produced by a single hybridoma or other cell line, or by a transgenic mammal such that each monoclonal antibody will typically recognize the same epitope on the antigen. The term "monoclonal" is not limited to any particular method for making the antibody, nor is the term limited to antibodies produced in a particular species, e.g., mouse, rat, etc. The term "polyclonal antibody" refers to a heterogeneous mixture of antibodies that recognize and bind to different epitopes on the same antigen. Polyclonal antibodies may be obtained, for example, from crude serum preparations or may be purified using, for example, antigen affinity chromatography, or Protein A/Protein G affinity chromatography.

The terms "percent (%) amino acid sequence identity" with respect to the polypeptide sequences identified herein, is defined as the percentage of amino acid residues in a candidate sequence that are identical with the amino acid residues in a specific polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2, or Megalign (DNASTAR) software. Persons of ordinary skill in the art can determine appropriate parameters for measuring alignment, including any algorithms needed to achieve maximal alignment over the full length of the sequences being compared. For instance, percent amino acid sequence identity may be determined using the sequence comparison program NCBI-BLAST2 (Altschul et al., Nucleic Acids Res. 25:3389 3402 (1997)). The NCBI-BLAST2 sequence comparison program may be obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

The terms "percent (%) nucleic acid sequence identity" with respect to polypeptide-encoding nucleic acid sequences identified herein is defined as the percentage of nucleotides in a candidate sequence that are identical with the nucleotides in the polypeptide nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, ALIGN-2, or Megalign (DNASTAR) software. Persons of ordinary skill in the art can determine appropriate parameters for measuring alignment, including any algorithms needed to achieve maximal alignment over the full length of the sequences being compared. For instance, percent nucleic acid sequence identity may also be determined using the sequence comparison program NCBI-BLAST2 (Altschul et al., Nucleic Acids Res. 25:3389 3402 (1997)). The NCBI-BLAST2 sequence comparison program may be obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide." A polynucleotide can comprise a nucleotide sequence disclosed herein wherein thymidine (T) can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

A "recombinant" polynucleotide (e.g., DNA or RNA molecule) or "recombinant" polypeptide is a polynucleotide or polypeptide that has been subjected to molecular manipulation in vitro.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by, but not limited to, those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "variant" refers to a molecule that exhibits a variation from a described type or norm, such as a protein that has one or more different amino acid residues in the corresponding position(s) of a specifically described protein (e.g. the CAE-protein shown in FIG. 1 or FIG. 2). An analog is an example of a variant protein. Splice isoforms and single nucleotides polymorphisms (SNPs) are further examples of variants.

The polypeptides having colanic acid-degrading (CAE) activity of the invention include those specifically identified herein, as well as allelic variants, conservative substitution variants, analogs and homologs that can be isolated/generated and characterized without undue experimentation following the methods outlined herein or readily available in the art. Fusion proteins that combine parts of different CAE proteins or fragments thereof, as well as fusion proteins of a CAE protein and a heterologous polypeptide are also included. Such CAE proteins are collectively referred to as the CAE-related proteins, the proteins of the invention, or CAE. The term "CAE-related protein" refers to a polypeptide fragment or a CAE protein sequence of at least 10, 15, 25, 50, 100, 150, 200, 250, 300, 350, 400, 450, 500, 550, 600, 650, 700, or more than 700 amino acids.

DETAILED DESCRIPTION

The present disclosure generally relates to "superclean" plasmid DNA preparations, processes for their preparation, and enzymes useful in these processes. Polysaccharides, particularly colanic acid, have been found to contaminate purportedly "clean" preparations of plasmid DNA that induce toxic effects in humans and mammals when used, e.g., for gene therapy. The components that are believed to induce these toxic effects have not been identified in the literature. Other applications that can be adversely affected by the presence of polysaccharide contaminants in DNA preparations include clinical diagnostics, forensics, and other biotechnology methodologies, such as chips and microarrays including nucleic acids thereon, and in molecular studies (e.g., building chromosomes, analyses of transcriptional start sites, X-ray crystallography, and DNA structural studies, among others). An urgent need exists to remove such contaminant molecules from DNA preparations.

Among other things, therefore, the present invention provides isolated, purified, and recombinant polypeptides having colanic acid-degrading activity, and processes involving their use. The invention also provides isolated polynucleotides encoding such polypeptides. The polypeptides described herein have a range of uses, and enable processes for digesting colanic acid in a biological material, and processes for removing endotoxins from compositions including biological macromolecules. Significantly, the polypeptides also enable the preparation of plasmid DNA preparations, preferably gram negative bacterial plasmid DNA, comprising less than about 0.1 mg of colanic acid per mg of plasmid DNA, and more preferably less than about 0.05 mg of colanic acid per mg of plasmid DNA. In certain preferred embodiments, no detectable colanic acid can be found in the plasmid compositions prepared by the processes described herein. The plasmid compositions may also have very low levels, or undetectable levels, of other polysaccharide contaminants, such as uronic acid and fucose.

The disclosure relates, in part, to the discovery that the polypeptide compounds of the invention are capable of digesting colanic acid (also known as M-antigen), an exopolysaccharide produced by a range of enterobacteria, including the majority of *Escherichia coli* strains. Depending on the bacteria, for example, colanic acid may be comprised of fucose, glucose, galactose, and glucuronic acid, together with acetate and pyruvate, in various ratios (see, e.g., Sutherland, Biochem. J. 115, 935-945 (1969). As noted above, endotoxins and polysaccharides, and in particular colanic acid, have been found to contaminate preparations of nucleic acids, e.g., for therapeutic uses, and it is difficult to separate endotoxins and polysaccharides such as colanic acid from nucleic acids using current standard purification procedures.

Accordingly, the polypeptides described herein may be generally used in the digestion of colanic acid in a material. In general, any material including colanic acid may be treated with the polypeptides described herein; typically, the material is a biological material. The biological material may be derived from, or a part of, microbes, tissues from humans and animals, and environmental samples such as archaeological remains, compost or other decomposing matter, peat bogs, plant matter, sediment, sludge, soil, and wastewater, e.g., that are terrestrial or subterranean in origin. In certain embodiments, the biological material is a biological slime. In accordance with these embodiments, for example, the colanic acid may be present in the cellular membrane of the intact bacteria. In other embodiments, the biological material may be a crude bacterial lysate, a partially purified bacterial lysate, or an aqueous solution comprising extracted bacterial nucleic acid. In another embodiment, the biological material may be a biofilm. In another embodiment, the biological material may be pulp or pulp derivative (e.g., such as those mechanically or chemically prepared from wood or fiber sources). As noted above, in accordance with other aspects of the invention, the polypeptides described herein may be used in processes for the removal of endotoxins from aqueous compositions comprising bacterial macromolecules (e.g., plasmid DNA). In certain preferred aspects, the polypeptides are used in processes for the purification of plasmid DNA, typically gram negative bacterial plasmid DNA.

Plasmid DNA Compositions

One key aspect of the present disclosure is highly purified plasmid compositions and pharmaceutical grade plasmid DNA compositions. These compositions, for example, may generally be produced by the colanic acid enzymatic digestion processes described herein, which may or may not be combined with conventional purification techniques, such as one or more combinations of chromatography and filtration steps. Thus, the invention encompasses, or in addition comprises, a process of producing and isolating highly purified plasmid compositions that are essentially free of polysaccharides including colanic acid, fucose, and uronic acid, and other contaminants, and thus is pharmaceutical grade DNA. In addition to having very low, and preferably undetectable, levels of colanic acid and other polysaccharides, the plasmid DNA produced and isolated by the processes described herein includes very low levels of endotoxin generally, including one or more of contaminating chromosomal DNA, RNA, protein, and endotoxins, and preferably contains mostly closed circular form plasmid DNA. The plasmid DNA produced according to the processes described herein is of sufficient purity for use research and plasmid-based therapy.

The plasmid compositions of the present invention may include any types of vectors with any sizes. For instance, the size range of plasmid DNA that may be purified by the processes described herein may be from approximately 0.3 kbp (mini-circle or minimal transcription unit) to approximately 50 kbp, typically 3 kbp to 20 kbp, or larger (e.g., 5 to 100 kbp, or larger, such as phage-derived shuttle vectors, HACs, YACs, MACs, and episomes derived from EBV or other non-integrating viruses). In certain embodiments, the DNA includes a vector backbone of approximately 0.3 kbp, 0.5 kbp, 0.75 kbp, 1 kbp, 3 kbp, 5 kbp, 10 kbp, 15 kbp, or 20 kbp, a therapeutic gene, and associated regulatory sequences. This may also apply to single stranded DNA (i.e., 0.3 kb to 50 kb, etc., such as those derived from M13). Thus, for example, a vector backbone may be capable of carrying inserts of approximately 1-50 kbp, or larger (e.g., 3-20 kbp), or approximately 1-50 kb, or larger (e.g., 3-20 kb). The insert will generally depend on application in which the plasmid composition is to be used. For gene therapy or vaccine-based applications, for example, the insert may include DNA from any organism, but will typically be of mammalian origin, and may include, in addition to a gene encoding a therapeutic protein, regulatory sequences such as promoters, poly adenylation sequences, enhancers, locus control regions, etc. The gene encoding a therapeutic protein may be of genomic origin, and therefore contain exons and introns as reflected in its genomic organization, or it may be derived from complementary DNA. Such vectors may include for example vector backbone replicatable with high copy number replication, having a polylinker for insertion of a therapeutic gene, a gene encoding a selectable marker, e.g., the tetracycline or kanamycin resistance gene, and is physically small and stable. The vector backbone of the plasmid advantageously permits inserts of fragments of mammalian, other eukaryotic, prokaryotic or viral DNA, and the resulting plasmid may be purified as described herein and used in vivo or ex vivo plasmid-based therapy, or other use. The plasmid compositions can also comprise other pharmaceutically acceptable components, buffers, stabilizers, or compounds for improving gene transfer and particularly plasmid DNA transfer into a cell or organism.

In general, "superclean" plasmid DNA compositions are provided herein. Typically, the plasmid DNA composition is a gram negative bacterial plasmid DNA composition. As described herein, an efficient enzymatically-based process has been developed that allows for the removal of colanic acid contamination from a variety of bacterial materials, such as plasmid DNA samples. In various embodiments, the first step in the process may involve detection of colanic acid as a source of contamination (e.g., plasmid DNA contamination). This may be directly or indirectly accomplished, for example, by assaying for the presence of fucose in the sample (described below), since fucose is known to make up about 22% of colanic acid.

In one embodiment, the plasmid DNA composition is a gram negative bacterial plasmid DNA composition comprising gram negative bacterial plasmid DNA and less than about 0.1 mg of colanic acid per mg of gram negative bacterial plasmid DNA. More preferably in this embodiment, the composition comprises less than about 0.05 mg of colanic acid per mg of gram negative bacterial plasmid DNA. In one particularly preferred embodiment, the gram negative bacterial plasmid DNA composition comprises no detectable colanic acid.

As noted elsewhere herein, the plasmid DNA compositions of the invention also preferably include low or undetectable levels or other polysaccharide contaminants, such as uronic acid or fucose. Thus, in one embodiment, the gram negative bacterial plasmid DNA composition comprises less than 0.1 mg of uronic acid per mg of gram negative bacterial plasmid DNA. More preferably in this embodiment, the gram negative bacterial plasmid DNA composition comprises less than 0.05 mg of uronic acid per mg of gram negative bacterial plasmid DNA. Preferably, no detectable uronic acid can be found in the plasmid DNA composition.

In these and other embodiments, the gram negative bacterial plasmid DNA composition preferably comprises less than 0.1 mg of fucose per mg of gram negative bacterial plasmid DNA. More preferably in this embodiment, the gram negative bacterial plasmid DNA composition comprises less than 0.05 mg of fucose per mg of gram negative bacterial plasmid DNA. Preferably, no detectable fucose can be found in the plasmid DNA composition.

In combination, the gram negative bacterial plasmid DNA composition may comprise less than about 0.1 mg of colanic acid per mg of gram negative bacterial plasmid DNA, and less than about 0.1 mg of uronic acid per mg of gram negative bacterial plasmid DNA. For instance, the gram negative bacterial plasmid DNA composition may comprise 0.05 mg of colanic acid per mg of gram negative bacterial plasmid DNA, and less than about 0.05 mg of uronic acid per mg of gram negative bacterial plasmid DNA. Preferably, no detectable colanic acid and no detectable uronic acid is present in the gram negative bacterial plasmid DNA composition.

By way of another combination, the gram negative bacterial plasmid DNA composition may comprise less than about 0.1 mg of colanic acid per mg of gram negative bacterial plasmid DNA, and less than about 0.1 mg of fucose per mg of gram negative bacterial plasmid DNA. For instance, the gram negative bacterial plasmid DNA composition may comprise 0.05 mg of colanic acid per mg of gram negative bacterial plasmid DNA, and less than about 0.05 mg of fucose per mg of gram negative bacterial plasmid DNA. Preferably, no detectable colanic acid and no detectable fucose is present in the gram negative bacterial plasmid DNA composition.

In yet another combination, the gram negative bacterial plasmid DNA composition may comprise less than about 0.1 mg of colanic acid per mg of gram negative bacterial plasmid DNA, less than about 0.1 mg of uronic acid per mg of gram negative bacterial plasmid DNA, and less than about 0.1 mg of fucose per mg of gram negative bacterial plasmid DNA. For instance, the gram negative bacterial plasmid DNA composition may comprise 0.05 mg of colanic acid per mg of gram negative bacterial plasmid DNA, less than about 0.05 mg of uronic acid per mg of gram negative bacterial plasmid DNA, and less than 0.05 mg of fucose per mg of gram negative bacterial plasmid DNA. Preferably, no detectable colanic acid, no detectable uronic acid, and no detectable fucose is present in the gram negative bacterial plasmid DNA composition.

In addition to the reduced levels of colanic acid, uronic acid, and/or fucose discussed above, the plasmid compositions described herein may also include, for example, less than 0.01 mg chromosomal or genomic DNA, RNA, protein, and/or endotoxin contaminants per mg of gram negative bacterial plasmid DNA; more preferably, the composition includes less than 0.001 mg, less than 0.0001 mg, or less than 0.00001 mg chromosomal or genomic DNA, RNA, protein, and/or endotoxin contaminants per mg of gram negative bacterial plasmid DNA. In one embodiment, for example, the plasmid compositions may comprise less than 0.1 mg (more preferably, less than 0.05 mg; still more preferably, no detectable amount) of colanic acid per mg of gram negative bacterial plasmid DNA, and less than 0.01 mg (more preferably, less than 0.001 mg; still more preferably, 0.0001 mg) host cell chromosomal DNA or genomic DNA contaminants per mg of gram negative bacterial plasmid DNA. The plasmid composition may also comprise less than 0.1 mg (more preferably, less than 0.05 mg; still more preferably, no detectable amount) of colanic acid per mg of gram negative bacterial plasmid DNA composition, and less than 0.01 mg (more preferably, less than 0.001 mg; still more preferably, 0.0001 mg) host cell protein contaminants per mg of gram negative bacterial plasmid DNA.

Assays for detecting levels of colanic acid, uronic acid, fucose, and other polysaccharides are generally known in the art (or are described herein); methods of detecting chromosomal or genomic DNA, RNA, protein, and/or endotoxin that may be present in the plasmid compositions are also generally known in the art.

In one embodiment, for example, the plasmid composition of the present invention may include, less than 0.1 mg, preferably less than 0.05 mg of colanic acid per mg of gram negative plasmid DNA (e.g., 0.04, 0.03, 0.02, or 0.01 mg), and more preferably no detectable colanic acid, as measured by a bicinchoninic acid (BCA) assay. Suitable BCA assays are described, for example, in Meeuwsen et al., Biosci. Bioeng. 89, 107-109 (2000); and Verhoef et al., Carbohyd. Res. 340(11), 1780-1788 (2005). An exemplary BCA assay for measuring colanic acid levels is found in Example 16.

In another embodiment, the plasmid composition may include colanic acid at the levels recited in the previous paragraph, and further comprise less than about 0.1 mg, preferably less than about 0.05 mg of uronic acid per mg of gram negative plasmid DNA (e.g., 0.04, 0.03, 0.02, or 0.01 mg), and more preferably no detectable uronic acid, as measured by a uronic acid assay. In general, the uronic acid content of a plasmid DNA sample is measured using standard curves generated with heparin sulfate or glucuronic acid as standards. For instance, heparin sulfate resembles the polysaccharide contaminants from *E. coli*, because uronic acid comprises about 25% of the total weight of heparin sulfate. Heparin sulfate consists of 50% sugars by weight. Half of these sugars are glucosamine and the other half of the sugars are iduronic acid and glucuronic acid; the rest of the heparin sulfate is contributed by modifications of the sugars including sulfates and acetylamides. Alternatively, glucuronic acid can be used to create a standard curve for the direct measurement of uronic acid. The standard solution is placed is a glass test tube with a borate/sulfuric acid solution (e.g., 0.025 M sodium tetraborate 10-hydrate dissolved in sulfuric acid having a specific gravity of 1.84) and mixed. A solution of carbazole in absolute ethanol is added to the mixture and the entire mixture is vortexed and immersed in boiling water. The tubes are allowed to cool and the absorbance of the solution at 530 nm is read in a spectrophotometer. The absorbance values obtained for the standards are plotted against the concentration of the standards. The uronic acid content of plasmid DNA samples can be extrapolated from its absorbance value at 530 nm when the DNA sample has undergone the same reaction. The polysaccharide content of the plasmid DNA sample can then be extrapolated by multiplying the amount of uronic acid by a number ranging from 3.3 to 9.1 (depending on the prevalence of colanic acid, ECA and the O- and K-antigens in the sample). An exemplary uronic acid assay for measuring uronic acid levels is found in Example 16.

In another embodiment, the plasmid composition may include colanic acid and/or uronic acid at the levels recited in the previous paragraphs, and further comprise less than about 0.1 mg, preferably less than about 0.05 mg of fucose per mg of gram negative plasmid DNA (e.g., 0.04, 0.03, 0.02, or 0.01 mg), and more preferably no detectable fucose, as measured by a fucose assay. The basic procedures for assay of fucose content in samples can be found in Morris, Anal. Biochem. 121, 129-134 (1982). Detailed descriptions of the solution preparation and storage conditions for solutions and samples for this assay have also been published (Passonneau, J. V. and O. H. Lowry. 1974. In: *Methods of Enzymatic Analysis*, U. H. Bergmeyer (ed.), 2nd edition, Academic Press: New York, volume 4, pp. 2059-2072). Using this method, the fucose levels of plasmid DNA samples were determined and the concentration of colanic acid levels calculated. As described elsewhere herein, colanic acid was found to be the primary contaminant in plasmid DNA from a variety of sources, even GMP grade plasmid DNA. An exemplary fucose assay for measuring fucose levels is found in Example 16.

In these and other embodiments, the gram negative plasmid composition preferably comprises no visually detectable polysaccharides when combined with a polysaccharide-selective labeling agent. In general, polysaccharide visualization assays involve labeling polysaccharides with a fluorescent agent and detecting their presence, e.g., on a electrophoretic medium. Preferably, no polysaccharides are detectable using such agents in combination with the plasmid compositions described herein. In one embodiment, the polysaccharide-selective labeling agent is (4,6-dichlorotriazinyl)aminofluorescein (DTAF). Other polysaccharide-selective labeling agents are known or will be evident to those skilled in the art. An exemplary assay utilizing a polysaccharide-selective labeling agent is found in Example 16.

In addition, viscosity of plasmid DNA compositions are reduced as a result of the colanic acid degradation processes described herein. Accordingly, the presence of colanic acid may be detected by comparing the viscosity of a treated plasmid DNA composition with the viscosity of an untreated plasmid DNA sample. An exemplary assay utilizing viscosity levels of plasmid DNA is described in Example 16.

In general, as the levels of colanic acid (and/or the levels of uronic acid, fucose, or other polysaccharide or other contaminant) present in the plasmid composition are reduced, the $LD_{50}$ (the dose lethal to 50% of the test population) of the plasmid composition is increased. For instance, by reducing the level of colanic acid to less than 0.1 mg per mg of gram negative bacterial plasmid DNA, in one embodiment the corresponding $LD_{50}$ of the plasmid composition is increased by at least 25%; more preferably in this embodiment, by at least 50%. By further reductions in the levels of colanic acid (and other polysaccharides), and optionally similar reductions in the levels of other contaminants such as chromosomal or genomic DNA, RNA, protein, and/of endotoxin, the corresponding $LD_{50}$ of the plasmid composition may be increased by at least 50%, by at least 75%, or by at least 100%. By way of another example, by reducing the level of colanic acid to less than 0.05 mg per mg of gram negative bacterial plasmid DNA and the level of chromosomal or genomic DNA, RNA, protein, and/or endotoxin contaminants to less than 0.01 mg per mg of gram negative bacterial plasmid DNA, the corresponding $LD_{50}$ of the plasmid composition may be increased by at least 50%; more preferably in this embodiment, at least 100%.

In general, the plasmid compositions of the present invention may be utilized in a wide range of applications, including those in fields of bioterrorism (agent detection and analysis), environmental science (e.g., agriculture, horticulture, and forestry), food science, forensics, molecular biology, health and medicine (e.g., gene therapy, diagnostics, recombinant protein expression), and space science, to name a few. The highly pure plasmid compositions described herein may be employed in vivo or ex vivo, for example, in gene therapy and vaccine-based applications (i.e., the plasmid compositions may be administered to mammals, including humans). Additionally or alternatively, the plasmid compositions may be used in conventional diagnostics and forensics techniques, for example, to improve the stability, specificity, reproducibility, and/or sensitivity of such methodologies. This may include, for example, the analysis, detection, or examination of samples from the environment, e.g. from public water supplies, samples from foodstuffs, and from other biological or clinical samples, such as blood, saliva, sputum, semen, buccal smears, urine or fecal waste, cell and tissue biopsies and micro dissections, amniotic fluid, or tissue homogenates of plants, animals, or human patients, and the like. Other examples of uses for the plasmid compositions described herein include genotyping microorganisms, DNA fingerprinting of plants and animals, detecting pathogens and beneficial microorganisms in soils, water, plants and animals, forensic identification of biological samples and environmental samples contaminated with different biological entities, and molecular studies such as, for instance, building chromosomes, analyses of transcriptional information, X-ray crystallography, and DNA structural studies. The plasmid compositions may also be used in conjunction or in combination with solid substrate chip formats that detect, among other things, genes, mutations or mRNA expression levels such as nucleic acid microarrays and molecular detection chips employing, for example, fluorescence, radioactivity, optical interferometry, Raman spectrometry, semi-conductor, or other electronics (see, e.g., U.S. Pat. No. 7,098,286; U.S. Pat. No. 6,924,094; and U.S. Pat. No. 6,824,866 (each of which is hereby incorporated by reference herein)).

Processes

As described elsewhere herein, the polypeptides of the present invention can be utilized in a wide range of processes, particularly those which involve, require, or otherwise benefit from digestion or degradation of colanic acid, typically in a biological material, such as a bacterial sample, or compositions (such as aqueous compositions) comprising bacterial macromolecules. In general, biological material including undesirable colanic acid may be treated with the polypeptides described herein, including biofilms (i.e., structured communities of microorganisms encapsulated within self-developed polymeric matrices, either adherent to a living or inert surface, or on its own), bacterial lysates, plasmid DNA, and the like.

The processes described herein generally involve the digestion of colanic acid in a biological material, or otherwise in a composition comprising a biological material. In general, the processes employ the polypeptides described herein to digest or degrade colanic acid that may be present in the material. One embodiment of the processes described herein involves, for example, the digestion of colanic acid from a biological material. Alternatively, the processes may involve the digestion of colanic acid in an aqueous composition containing bacterial macromolecules. By way of another alternative, the processes may involve treating an aqueous composition containing plasmid DNA with a polypeptide to digest colanic acid.

A polypeptide is used to digest colanic acid present in the sample; thus, the polynucleotide has colanic acid-degrading activity, or is otherwise a colanic acid-degrading enzyme. In one particular embodiment, the process involves digesting in a biological material and the process comprises contacting the biological material with a polypeptide capable of digesting colanic acid. The biological material may be, for example, a crude bacterial lysate, a partially purified bacterial lysate, and an aqueous solution containing extracted bacterial nucleic acid (such as gram negative plasmid DNA). Alternatively, the biological material may be a bacterial slime. By way of another alternative, the biological material may be a biofilm comprising gram negative bacteria. In another alternative embodiment, the bacterial material may be present in a pulp (e.g., wood or fiber pulp) composition, solution, or mixture. In another embodiment, the process involves the removal of endotoxin from an aqueous composition containing bacterial macromolecules and the process comprises digesting colanic acid in the aqueous composition and thereafter combining the aqueous composition with a chromatographic material to separate endotoxin from the bacterial macromolecule. In one preferred embodiment, the process involves purification of plasmid DNA, such as gram negative bacterial plasmid DNA, and the process comprises treating an aqueous composition containing plasmid DNA with a polypeptide to digest colanic acid and separating the plasmid DNA from the treated aqueous composition using, for example, conventional chromatography techniques. The polypeptide may also be employed in a range of industrial processes described below.

In a particular aspect, a process for removal of contaminating polysaccharides from plasmid DNA samples has been developed that allows for the removal of polysaccharides, including those other than LPS, from plasmid DNA samples. In addition, RNA and LPS are also removed from the plasmid DNA samples. Therefore, the method of the present invention results in purified plasmid DNA that contains extremely low, and in many cases undetectable, levels of polysaccharides as described below. Unlike previous methods, which were unable to identify the levels of contaminating polysaccharides, the certain steps may be performed to quantify the polysaccharide levels in DNA samples, allowing the investigator to assure the removal of polysaccharides from the DNA sample.

In general, any of the polypeptides described herein may be employed. For example, the polypeptide may comprise an amino acid sequence having at least 90% homology to SEQ ID NO: 1, or the polypeptide may comprise an amino acid sequence having at least 90% homology to SEQ ID NO: 2. In one particular embodiment, the polypeptide has the amino acid sequence of SEQ ID NO: 1. In another particular embodiment, the polypeptide has the amino acid sequence of SEQ ID NO: 2.

The starting material for certain of the processes described herein is a mass of bacterial material, or an aqueous composition comprising such biological material, such as bacterial cells or other biological matter prepared by, e.g., fermentation or cell culture, isolated from the environment, or derived from tissues or other organisms (e.g., fungi, bacteria, etc.). In one embodiment, the biological material comprises bacterial cells derived from enterobacteria, such as *E. coli*. In another embodiment, the biological material is a bacterial slime; according to this embodiment, for example, colanic acid is present in the cellular membrane of the bacteria. In a preferred embodiment, the biological material is a gram negative bacterial plasmid DNA material.

A variety of cell types can be used as feed for the processes described herein, such as bacteria (e.g., gram (−), gram (+), and Archaea), yeast, and other prokaryotic and eukaryotic cells, including mammalian cells and recombinant cells. Among these and other cell types, bacterial cells, and in particular gram positive (+) and gram negative (−) bacterial cells, such as *E. coli, Salmonella*, or *Bacillus*, are preferred, with gram negative (−) bacterial cells being most preferred. In a particular embodiment, the bacteria is a gram negative (−) bacteria; more preferably in this embodiment, the bacteria is *E. coli*. A wide selection of well-established *E. coli* host strains are useful according to the processes described herein, and are available from Stratagene (La Jolla, Calif.), Qiagen (Valencia, Calif.), New England BioLabs (Ipswich, Mass.), and Promega (Madison, Wis.), among other commercial sources.

Typically, the biological material is a bacterial lysate, or a derivative thereof. Thus, bacterial starting material (e.g., bacterial cells, etc.) must be lysed or disrupted to form the lysate. In general, the bacterial lysis step involves any conventional method for breaking open bacterial cells, thus liberating nucleic acids and other cell components therefrom. The lysis procedure may involve the use of mechanical methods, lysing agents or solutions, or combinations thereof.

For biological material derived from fermentation or cell culture, the cells are disrupted by chemical or mechanical techniques as described below, forming a crude lysate. For example, where bacterial cultures are employed, the bacterial cells are lysed to form a crude bacterial lysate. In doing so, the cellular components, including DNA, RNA, proteins, colanic acid, and other polysaccharides, are released from the cells. In certain embodiments, the lysate may undergo pre-treatment steps, such as purification steps to remove cell contaminants and endotoxins, thus forming a partially purified (e.g., bacterial) lysate.

Where a lysing agent is employed, the lysing agent is used to break down cell membranes, thus releasing DNA, RNA and proteins from the cells. One preferred lysing agent comprises an alkaline solution. A variety of bases may be employed in conventional alkaline lysis procedures, including, for example, hydroxide salts, such as potassium hydroxide (KOH), lithium hydroxide (LiOH), or sodium hydroxide (NaOH). Typically, the base is sodium hydroxide. Often, detergents are employed in lysing solutions, either alone or in combination with the alkaline solution. In general, and depending on the application, the detergent may be an cationic, anionic, non-ionic, or zwitterionic detergent, or a combination thereof. One exemplary anionic detergent is sodium dodecyl sulfate (SDS). One exemplary zwitterionic or non-ionic detergent is Tween 20.

Mechanical methods for lysing bacterial cells, for use either alone or in combination with lysis solutions and agents, include agitation, sonication, centrifugation, freeze/thawing, French cell press, and the like.

Alkaline lysis and mechanical techniques for lysing bacterial cells to release and extract proteins and nucleic acids are generally well known, and are described, for example, in Sambrook et al., supra.

In some embodiments, it may be desirable to form a cleared lysate preparation, in which the chromosomal DNA, proteins, and membrane portions of the host cells have been at least partially removed, such as by chemical treatment or centrifugation of the lysate, thereby leaving a solution containing plasmid DNA. RNAse can optionally be added at various points in the procedure to create a cleared lysate that is substantially free of RNA. As noted elsewhere herein, initial removal of many cellular and nucleic acid contaminants can improve colanic acid digestion and/or further purification of the plasmid DNA using conventional chromatographic techniques. Methods of creating cleared lysates are well-known in the art. For example, a cleared lysate can be produced by treating the host cells with sodium hydroxide or its equivalent (0.2N) and sodium dodecyl sulfate (SDS) (1%), centrifuging, and discarding the supernatant. This method of creating a cleared lysate is generally described, for example, in Burnboim et al., Nucl. Acids Res., 7, 1513 (1979); and Horowicz et al., Nucl. Acids Res., 9, 2989 (1981).

For many uses, e.g., therapeutic uses such as in gene therapy or the formation of vaccines, it may be desirable to further purify the nucleic acid obtained from the bacterial or other lysate, either before or after the sample is contacted with the colanic acid-degrading polypeptide.

After forming the bacterial lysate as described above, it is generally preferably to subject the crude lysate to separation techniques to eliminate at least part of the other nucleic acid, protein, and cell contaminants that are present, before attempting to digest colanic acid with the polypeptide. Thus, in one embodiment, for example, the material or composition comprising the biological matter is combined with an ion exchange chromatographic material prior to treatment with the polypeptide. Typically, the chromatographic material is a anion exchange chromatographic resin. In a preferred embodiment, the anion exchange chromatographic resin comprises diethylaminoethyl cellulose (DEAE). In general, conventional DNA, including plasmid DNA, cleaning techniques can be employed.

The biological material may also be combined with chromatographic material following treatment with the polypeptide. This generally involves affinity chromatography and/or hydrophobic interaction chromatography. In a particular embodiment, the biological material or aqueous composition is combined with an anion exchange chromatography resin, treated with the polypeptide, combined with an affinity chromatography resin, combined with a hydrophobic interaction chromatography resin, and subjected to filtration, in that order.

Once the biological material is lysed or otherwise prepared, the material is treated with the polypeptide described herein. Typically, treatment involves contacting or mixing the polypeptide with the biological material such that the polypeptide will have access to the colanic acid substrate present in the material or composition. Preferably, the biological material and the polypeptide are incubated to allow sufficient interaction between the enzyme and the colanic acid substrate. Typically, the duration of the incubation may be from 1 to 6 hours, 6 to 12 hours, 12 to 24 hours, or longer, depending on the size of the sample to be digested, the amount of polypeptide employed, and environmental factors, such as temperature, atmosphere, etc. The incubation is generally carried out at a temperature of between 0° C. and 100° C., more preferably between 25° C. and 75° C. (e.g., between 30° C. and 50° C.). In some embodiments, it may be desirable to vary the temperature during the incubation process, for example, starting the incubation at a cooler temperature, and then raising the temperature for the remainder of the incubation cycle, or vice versa.

As noted above, it will generally be desirable to purify the biological material or aqueous composition containing biological material, either before or after treatment with the polypeptides of the invention. In general, this may involve subjecting the material or composition to one or more chromatography methods or to filtration. In one embodiment, a combination of chromatographic separations are employed. Thus, for example, at various times during the process, the biological material or composition may be combined with a chromatographic material. Suitable chromatographic materials include, for example, ion exchange chromatography resins (such as anion exchange chromatography resins and cation exchange chromatography resins), hydrophobic interaction chromatography resins, and affinity chromatography resins, among a range of others. In one embodiment, the chromatographic material is selected from the group consisting of an anion exchange chromatography resin, a cation exchange chromatography resin, a hydrophobic interaction chromatography resin, and an affinity chromatography resin.

As noted above, the biological material or composition may be combined with the chromatographic material(s) prior to, or after, treatment with the polypeptide, or both before and after treatment with the polypeptide, with single or multiple chromatographic separations being employed. For example, the sample can be combined with a chromatography material, treated with the polypeptide as described herein, and subjected to a second (or third, fourth, fifth, etc.) chromatography step. In addition, the sample can be subjected to conventional filtration techniques to further purify or remove contaminants from the sample. The filtration steps may occur relatively early in the process, e.g., prior to treatment with the enzyme, or later in the process, e.g., as final filtration steps prior to storage or use of the end product.

In another aspect, therefore, the processes of the invention comprise the use of an polypeptide capable of degrading colanic acid present in a bacterial lysate sample, which is preceded by or followed by at least one additional chromatography technique. The additional chromatography step may exist optionally or typically as one or more of the final purification steps or at least at the end or near the end of the sample or plasmid purification scheme, or prior to the colanic acid digestion step. In combination with the colanic acid degradation step, therefore, is preferably one or more of ion exchange chromatography, affinity chromatography (e.g., boronate affinity chromatography), hydrophobic interaction chromatography, and filtration. Other techniques may include gel permeation or size exclusion chromatography, hydroxyapatite (type I and II) chromatography, and reversed phase chromatography. In general, any available chromatography protocol involving nucleic acid separation can be adapted for use. In addition, any one or more of the steps or techniques can employ high performance chromatography techniques or systems. Thus, the method of the invention comprises an colanic acid digestion step with one or more step of ion exchange chromatography and further may include affinity chromatography, hydrophobic interaction chromatography or gel permeation chromatography, and/or filtration (such as tangential flow filtration (TFF) or size exclusion filtration). The step of ion exchange chromatography, for example, may be both in fluidized bed ion exchange chromatography and axial and/or radial high resolution anion exchange chromatography. In one preferred embodiment, ion exchange chromatography is performed prior to the colanic acid degradation step, in order to remove particles that may hinder the ability of the enzyme to interact with the substrate.

Processes of the invention described herein, e.g., for purifying plasmid DNA, are scalable and thus amenable to scale-up to large-scale manufacture.

In some embodiments of the invention, colanic acid degradation step may be combined with additional purification steps to result in a high purity product containing plasmid DNA. It may, for example, be combined with at least one of flocculate removal (such as lysate filtration, settling, or centrifugation), ion exchange chromatography (such as cation or anion exchange), and hydrophobic interaction chromatography. In one embodiment, the colanic acid degradation step is preceded by ion exchange chromatography. In these and other embodiments, the colanic acid degradation step is followed by hydrophobic interaction chromatography. In a preferred embodiment, bacterial lysis is followed by ion exchange chromatography, ion exchange chromatography is followed by affinity chromatography (e.g., using boronates or other vicinal- or cis-diol specific compounds), which is followed by hydrophobic interaction chromatography. After or between one or more of these steps, the sample can be subjected to filtration, such as tangential flow filtration. These steps allow for a truly scaleable plasmid manufacturing process, which can produce large quantities of plasmid DNA with high levels of purity. Host cell DNA and RNA, proteins, endotoxins, and colanic acid contaminants are preferably undetectable.

As noted above, the method of the present invention may also use further steps of size exclusion chromatography (SEC), reversed-phase chromatography, hydroxyapatite chromatography, and/or other available chromatography techniques, methods, or systems in combination with the steps described herein in accordance with the present application.

A flocculate removal step may also be employed to provide higher purity to the resulting plasmid DNA product. This step may be used to remove a large portion of precipitated material (flocculate). One mechanism of performing flocculate removal is through a lysate filtration step, such as through a 1 to 5 mm, and preferably a 3.5 mm grid filter, followed by a depth filtration as a polishing filtration step. Other methods of performing flocculate removal are through centrifugation or settling. Alternatively, the flocculate may be removed by ion exchange chromatography.

At various times in the endotoxin removal and/or plasmid DNA purification process, therefore, the sample may be subjected to one or more of ion exchange chromatography (e.g., anion or cation exchange chromatography), affinity chromatography, hydrophobic interaction chromatography, and filtration (e.g., filtered through a 0.2 µm and/or 0.45 µm filter), and, optionally, filtered or subjected to chromatography methods a second, third, or fourth time, or more.

Thus, for example, the sample can be subjected to a first chromatography material, treated with the polypeptide, subjected to a second chromatography material, and subjected to a third chromatography material. The sample may also be filtered at various times in the sequence, such as after the first chromatographic separation, or after the third chromatographic separation. It will be understood that subjecting the sample to a chromatographic material also involves eluting the desired portion of the sample (such as that portion containing purified plasmid DNA) from the chromatographic material, and discarding undesired portions of the sample. Depending on the nature of the chromatographic material, the desired portions may be retained within the chromatographic material and eluted in a separate step while the undesired materials flow through the material, or the undesired materials may be retained in the chromatographic material while the desired portions flow through the chromatographic material.

At a variety of places in the above protocol, analytical determination of nucleic acid yield and purity are advantageously performed. Typically, such assays are performed before and after each purification step, as well as to each nucleic acid-containing fraction from, e.g., preparative ion exchange chromatography or filtration. Representative means for performing these analytical determinations include HPLC analysis of purity, spectrophotometric estimation of yield, silver staining and SDS-PAGE for protein analysis, and agarose gel electrophoresis and Southern blotting for DNA analysis. In certain embodiments, the processes described herein yields a purified concentrate with a plasmid DNA concentration (including, for example, predominantly supercoiled or other plasmid DNA) of around 70%, 75%, 80%, 85%, 90%, 95%, and preferably 99%, or greater.

Additionally, it is also generally desirable to analytically determine the presence of polysaccharides such as colanic acid, uronic acid, and/or fucose in the intermediate or end products. Suitable assays for the detection of colanic acid and other polysaccharides are described elsewhere herein (e.g., in Example 16).

Particular chromatographic and filtration techniques are described in further detail below.

Ion Exchange Chromatography

As noted above, ion exchange chromatography can be employed to purify the biological sample prior to treatment with the polypeptide, or thereafter. This process generally separates nucleic acid, e.g., plasmid DNA, in the bacterial lysate or lysate derivative from contaminating endotoxin, trace proteins, and residual cellular contaminants. Cation or anion exchange may be selected depending on the properties of the contaminants and the pH of the solution. Anion exchange chromatography, for example, functions by binding negatively charged (or acidic) molecules to a support which is positively charged. The use of ion-exchange chromatography, then, allows molecules to be separated based upon their charge. Families of molecules (acidics, basics and neutrals) can be easily separated by this technique. Stepwise elution schemes may be used, with many contaminants eluting in the early fractions and the plasmid DNA eluted in the later fractions. Ion exchange chromatography is a relatively common method for removing proteins and endotoxin from plasmid DNA preparations. The ion exchange chromatography or any one or more of the other chromatography steps or techniques used can employ stationary phases, displacement chromatography methods, simulated moving bed technology, and/or continuous bed columns or systems.

The ion exchange columns that can be utilized in the processes of the present invention include both cationic and anionic ion exchange columns. In more preferred embodiments, the ion exchange chromatography material is anion exchange chromatography resin. For example, the anion exchange chromatography material resin may comprise diethylaminoethyl cellulose (DEAE), trimethylaminoethyl (TMAE), quaternary amino ethyl (QAE), or polyethyl imide (PEI) resins. In one embodiment, the anion exchange chromatography resin comprises DEAE. In another embodiment, the anion exchange chromatography resin comprises a quaternary ammonium resin. For instance, a chromatography column may be packed with one or more an anion exchange chromatography resins described herein. The optimal capacity of the column will be determined empirically based on the resin used and the size of nucleic acid to be purified. For many plasmid DNAs, preferred resins are those with no pore or with a large pore size, e.g., greater than 1000 Å, preferably around 3000 Å to 4000 Å; with a medium bead size, e.g., about 20 to 500 μm diameter; that does not leach matrix components. Ideally, the resin is also washable, e.g., with sodium hydroxide, to allow repeated use.

Relatively weak cationic and strong cationic ion exchange columns can also be used. Relatively strong cationic exchange columns typically have a surface coated with a polyhydroxylated polymer and functionalized with sulfopropyl, a dextran matrix functionalized with a sulfopropyl group, or a surface coated with a polyhydroxylated polymer functionalized with sulfoethyl. Examples of strong cationic ion exchange columns using each of these materials include, respectively, a POROS HS™, a POROS S™, and a SP-Sephadex™ column, among others. Relatively weak cationic exchange columns typically have a dextran matrix functionalized by carboxymethyl or an acrylic matrix functionalized by a carboxylic group. Examples of weak cationic exchange columns using each of these materials include, respectively, CM-Sephadex™ and Bio-Rex 70™.

Relatively weak anionic and strong anionic ion exchange columns can also be used in the methods of the present invention. Weak anionic ion exchange columns typically have a surface coated with polyethyleneimine that is capable of surface ionization up to a pH of about 9, a styrene-divinylbenzene copolymer containing sulfonic acid groups or a dextran matrix functionalized by diethylaminoethyl. Examples of weak anionic exchange columns using each of these materials include, respectively, a POROS PI™ column, a Dowex 50™ column and a DEAE-Sephadex™. Relatively strong anionic exchange columns typically have a surface coated with quaternized polyethyleneimine with a surface ionization over a pH range of about 1 to about 14. An example of a such a strong anionic ion exchange column is a POROS HQ™ column, or a SOURCE™ column. The resins for the columns listed above can be obtained from Amersham/Pharmacia (Piscataway, N.J.), PerSeptive Biosystems (Foster City, Calif.), Toso Haas (Montgomeryville, Pa.), GE Healthcare (Piscataway, N.J.), and other suppliers.

Typically, the sample is combined with an ion exchange chromatography resin that is present in a column. The column can be a 0.5 ml column, a 1.5 ml column, a 10 ml column, a 20 ml column, a 30 ml column, a 50 ml column, a 100 ml column, a 200 ml column, a 300 ml column, a 400 ml column, a 500 ml column, a 600 ml column, a 700 ml column, an 800 ml column, a 900 ml column, a 1000 ml (1 L) column a 2000 ml (2 L) a 10 L column, a 20 L column, a 30 L column, a 40 L column, a SOL column, a 60 L column, a 70 L column, an 80 L column a 90 L column, a 100 L column, or a column with a capacity greater than 100 L, as well as any other column with a capacity between the volumes listed above.

Typically, the ion exchange chromatography material is equilibrated prior to use at a pH ranging from about 6.0 to about 7.2 and at a salt concentration that can range from about 100 mM to 200 mM. Therefore, the column can be equilibrated at a pH of about 6.0, 6.1, 6.2, 6.3, 6.4, 6.5, 6.6, 6.7, 6.8, 6.9, 7.0, 7.1, 7.2 or any other pH in between these pH values and at a salt concentration of about 100 mM, 125 mM, 150 mM, 175 mM, 200 mM or any other concentration in between the salt concentration values listed above. Commonly used salts that can be utilized to equilibrate the chromatography material include NaCl, KCl or any other salt that can be adjusted to match the ionic strength of KCl.

For the ion exchange chromatography, packing material and method of preparing such material as well as process for preparing, polymerizing and functionalizing anion and cation exchange chromatography and eluting and separating plasmid DNA therethrough are well known in the art.

In addition, a chelating agent for bivalent metal ion may be used such as for example, ethylenediamine-tetraacetic acid (EDTA), for inhibiting the degradation of plasmids due to DNA-degrading enzymes in the lysate of *Escherichia coli*. The concentration of chelating agent for bivalent metal ion is preferably 0.1 to 100 mM.

When applying the protein of interest to an anion exchange matrix any suitable matrix can be employed including, but not limited to aminoethyl, diethylaminoethyl, quaternary aminomethyl, quaternary aminoethyl, diethyl-(2-hydroxypropyl)aminoethyl, triethylaminomethyl, triethylaminopropyl and polyethyleneimine exchangers, to achieve filtration of the protein of interest. Examples of commercially available anionic exchangers include the cellulose ion exchangers such as DE32 and DE52 (WHATMAN, Florham Park, N.J.), the dextran ion exchangers such as DEAE-SEPHADEX C-25, QAE-SEPHADEX C-25, DEAE-SEPHADEX C-50 and QAE-SEPHADEX C-50 (Pharmacia, Piscataway, N.J.), the agarose or cross-linked agarose such as DEAE BIO-GEL A (BIO-RAD, Hercules, Calif.), DEAE-SEPHAROSE CL-6B and Q-SEPHAROSE Fast Flow (Pharmacia), the synthetic organic polymers, such as MONO Q (Pharmacia), DEAE-5-PW and HRLC MA7P (BIO-RAD) and the coated silica matrices such as DEAE Si5500 and TEAP Si100. Desirably, the anion exchange matrix is equilibrated in very low salt concentrations and employed at an alkaline pH (e.g., pH 8.0 to 11.5) to facilitate binding of acid and mildly basic contaminants.

When applying the protein of interest to a cation exchange matrix, it is contemplated that any matrix functionalized with carboxymethyl, sulfonate, sulfoethyl or sulfopropyl groups can be employed. Desirably, the cation exchange matrix is equilibrated and employed at an acidic pH (e.g., pH 3.0 to 6.5) to facilitate binding of basic and mildly acidic contaminants. Examples of commercially available cationic exchangers are the cellulose-based CM 23, CM 32 and CM 52 (WHATMAN); the dextran based CM-SEPHADEX C-25, SP-SEPHADEX C-25, CM-SEPHADEX C-50 and SP-SEPHADEX C-50 (Pharmacia); the agarose or cross-linked agarose-based CM BIO-GEL A (BIO-RAD), CM-SEPHAROSE Fast Flow and S-SEPHAROSE Fast Flow (Pharmacia); the synthetic organic polymer-based MONO S (Pharmacia), SP-5-PW and HRLC MA7C (BIO-RAD) and the coated silica matrices such as CM Si300 and SP Si100.

The sample (e.g., the lysate or derivative thereof, including the nucleic acid) is typically loaded onto the column in a loading buffer comprising a salt concentration below the concentration at which the nucleic acid would elute from the column. Generally, the salt concentration will be in certain embodiments from about 10 to 50 mS, depending on the resin used. In general, for weaker anion-exchange resins, a lower conductivity solution will be used, whereas for stronger anion-exchange resins, a higher conductivity solution will be used. The column will then be washed with several column volumes of buffer to remove those substances that bind weakly to the resin. Fractions are then eluted from the column using a shallow continuous saline gradient according to conventional methods, for example, using up to 1.5M NaCl in a Tris-HCl buffer. Sample fractions are collected from the column. For intermediate scale preparations (e.g., from about 100 mg to about 3 grams nucleic acid), fractions will typically be at least 50 ml to 2 liters where the nucleic acid peak is expected, with increases in volume in the fractions past the expected peak. Analytical determinations of nucleic acid yield and purity are performed on single or multiple fractions. In addition, Limulus ameobocyte lysate (LAL) assays (e.g., to detect the Lipid A portion of endotoxin) may be performed on each fraction to determine residual endotoxin and/or other assays described herein may be performed on each fraction to determine residual polysaccharide contaminant levels, such as colanic acid or related polysaccharides (as described below), in each fraction. Fractions containing high levels of nucleic acid and low endotoxin or low colanic acid may be pooled, or maintained as separate fractions. The resulting nucleic acid samples may again be filtered (e.g., through a 0.2 µm filter) or subjected to further chromatography techniques depending on the endotoxin and polysaccharide levels and the desired purity, as described below.

The support matrices for the ion exchange chromatographic materials disclosed herein are not critical, however, support matrices based on dextran, cellulose, cross-linked agarose, synthetic organic polymers, coated silica or agarose are conventional in the art and suitable for use herein.

Affinity Chromatography

As noted above, affinity chromatography can additionally or alternatively be employed to purify the biological sample. A particular aspect of the invention involves the colanic acid degradation process using the polypeptides described herein, and combining the digested material with an affinity chromatography material to selectively remove digested polysaccharides such as colanic acid. Particularly preferred affinity chromatography materials have an affinity for vicinal or cis-diols. In one particular embodiment, the affinity chromatography material is a boronate chromatography resin, such as a boronic acid- or boronate-based resin.

In basic respects, the affinity chromatography involves preparation of a selective adsorbent by covalent immobilization of a molecule, containing a recognizable region, for which the target sample to be separated is specific, to a suitable insoluble support. The immobilized compound is generally referred to as a ligand and it is recognized that coupling of the ligand to the support must be accomplished in a manner which does not interfere with its ability to be recognized by the target. Affinity between ligand and the target molecule to be purified can be accomplished by passing the sample containing a sample containing the target molecule through a column containing the selective adsorbent. Purification is thereafter accomplished by washing the column with a buffer used to free the adsorbent matrix of unwanted materials, followed by elution of the adsorbed target molecule. Washing is accomplished by passing a volume of physiological buffer, such as phosphate buffered saline, about pH 7.2, through the column. The volume of buffer used in the washing step should not be so great as to result in target molecule loss but, on the other hand, not so limited so as not to remove impurities. Elution is the step wherein the target molecule is removed from the column by using a solvent that reduces the affinity of the target molecule to the ligand or the affinity of the ligand-target molecule complex to the solid support. Elution of an antibody coupled to the antigen may be accomplished by either a salt gradient, to change the pH; buffered step-gradient, to change the ionic strength; or other methods.

The ideal solid support or matrix should possess several characteristics including, macroporosity, mechanical stability, ease of activation, hydrophilicity, and inertness, i.e., low nonspecific adsorption. No matrix is ideal in all of these respects; the matrix is often determined empirically. Affinity chromatography matrices commonly used by those skilled in the art include cross-linked dextran, agarose, polyacrylamide, cellulose, silica and poly(hydroxyethylmethacrylate). For immuno-adsorbents, beaded agarose is generally the preferred solid support by those skilled in the art due to its high adsorptive capacity for proteins, high porosity, hydrophilicity, chemical stability, lack of charge and relative inertness toward nonspecific adsorption.

Ligands may be physically adsorbed to matrices or covalently attached to polymeric matrices containing hydroxylic or amino groups by means of bifunctional reagents. Attachment usually requires two steps, activation of the matrix and coupling of the ligand to the activated matrix. Activated matrices are available commercially. The selection method for coupling the ligand to the matrix is dictated in part by the choice of matrix, and, in part, by the choice of ligand.

The specific buffering conditions used for equilibrating the affinity column in preparation for sample application should reflect the specific properties of the interacting system being used. The nature of the buffer used, including its pH and ionic strength, should be optimal for the ligand-target molecule system. The target sample applied to the column should preferably be contained in the same buffer used to equilibrate the column. After sample application and adsorption, the column may be washed with the starting buffer to remove any unbound sample and any impurities. It is also common to then wash the column with buffers different from the starting buffer in order to remove nonspecifically adsorbed substances.

Elution of the target molecule may be accomplished by a number of methods, including but not limited to these presented here. Typically, the conditions of the buffer may be changed such that the affinity of the binding complex falls sufficiently, thereby destroying effective binding to each other or to the solid support. This is achieved by altering the pH, or the ionic strength of the buffer or both, or by chaotropic ions, e.g., cyanates. Increased separation may be obtained by gradient elution. Suitable methods of elution include use of chaotropic agents such as KSCN; organic solvents, e.g., ethylene glycol, DMSO, or acetonitrile; denaturing agents, e.g., 8 M urea or 6 M guanine; electrophoretic elution; pressure induced elution and metal ion elution. Incomplete elution results in both loss of product and loss of column capacity. Ideally, the elution conditions should allow for complete elution of the product after one or two column volumes have passed through the column.

Detailed discussions of affinity chromatography can be found in Handbook of Affinity Chromatography, David S. Hage (ed.) CRC Press (2006), and Affinity Chromatography: A Practical Approach, edited by Dean P. D. G., Johnson, W. S., Middle, F. A., Affinity Chromatography, Principles and Methods, as published by Pharmacia, (Pharmacia LKB Biotechnology, Uppsala, Sweden), and Immunoaffinity Purification: Basic Principles and Operational Considerations, Yarmush, M. L, et al., (1992) Biotech Adv., 10:412-446.

Ligands used for affinity chromatography are structurally and biologically closely related to the target molecule to be purified. For the purposes of the present invention, any suitable affinity chromatography material and ligand thereof can be employed for binding and eluting the sample of interest (i.e., plasmid DNA). In general, this makes the selection of the ligand specific for each case.

Preferably, the ligand used in the affinity chromatography material has specificity for diol complexes, preferably vicinal or cis-diols. Polysaccharides, such as colanic acid, for example, contain vicinal diol complexes. In a particularly preferred embodiment, the affinity chromatography material is a boronate affinity chromatography material. Boronate affinity columns were first employed for the separation of sugars and nucleic acid components by Weith et al, Biochemistry 9, 4396-4401, 1970; since then, this technique has been employed in the separation of a wide range of cis-diol compounds, including nucleosides, nucleotides, carbohydrates, glycoproteins, and enzymes.

In general, the mechanism of action between boronic acids and cis-diols involves hydroxylation of the boronate under basic conditions; the boronate goes from a trigonal coplanar form to a tetrahedral boronate anion, which can then form esters with cis-diols. The resulting diester can by hydrolyzed under acidic conditions, thus reversing the reaction. Other methods for separation of vicinal diols are described by Barry et al., Australian J. Chem. 37, (1984); Gable, Organometallics 13(6), 2486-88 (1994); Liu, J. Microbial Methods 29, 85-95 (1997) Kinrade et al., DaltonTrans. 3713-3716 (2003); and Zhao et al., Analytical Sciences, 22(5), 747 (2006).

Suitable boronate ligands for use in the affinity chromatography material of the present processes include, for example, 3-aminophenylboronic acid (3aPBA), 2-(((4-boronophenyl)-methyl)-ethylammonio)ethyl, 2-(((4-boronophenyl)-methyl)-diethylammonio)ethyl, p-(ω-aminoethyl)phenyl-boronate, poly(p-vinylbenzeneboronic acid), N-(4-nitro-3-dihydroxyborylphenyl)succinamic acid, 4-(N-methyl)carboxamido-benzeneboronic acid), 3-nitro-4-carboxamidobenzeneboronic acid, 2-nitro-3-succinamido-benzeneboronic acid, and 3-succinamido-4-nitro-benzeneboronic acid, among others. One preferred boronate ligand is 3-aminophenylboronic acid (3aPBA).

A range of support matrices for the affinity chromatographic materials disclosed herein, including boronate affinity chromatographic materials, are not critical, however, support matrices based on dextran, cellulose, agarose, polyacrylamide, silica, polystyrene, and polymethacrylate are conventional in the art and suitable for use herein. Boronate affinity matrices are commercially available from a variety of vendors, including for example, Sigma-Aldrich Inc. (Boric acid gel; polymethacrylate support) (m-aminophenylboronic acid-acrylate; acrylic bead support); Bio-Rad (Alli-Gel 601; polyacrylamide support); Pierce (immobilized boronic acid gel; polyacrylamide support); and Tosoh (m-aminophenylboronic acid-agarose; agarose support) (TSKgel Boronate-5PW column; polymethacrylate support). Other companies supplying boronic acid and derivatives thereof include Denisco (Hyderabad, India) and Synthonix Corporation (Wake Forest, N.C.).

Polymer gels containing boronate groups described in U.S. Pat. No. 5,969,129 (hereby incorporated by reference herein in its entirety) may also be used.

The principles, theory and devices used for boronate affinity chromatography are also described in Boronate Affinity Chromatography, Chapter 8, pages 215-230, Handbook of Affinity Chromatography, David S. Hage (ed.) CRC Press (2006).

Hydrophobic Interaction Chromatography

In the embodiments in which hydrophobic interaction chromatography (HIC) materials and methods are employed, these chromatography methods generally employ hydrophobic moieties on a substrate to attract hydrophobic regions in molecules in the sample for purification. In general, HIC supports work by a clustering effect; typically, no covalent or ionic bonds are formed or shared when these molecules associate. Hydrophobic interaction chromatography is beneficial as it is at least partially removes open circular plasmid forms and other contaminants, such as genomic DNA, RNA, and endotoxin.

For the purposes of the present invention, any suitable hydrophobic interaction matrix can be employed for binding and eluting the sample of interest (e.g., plasmid DNA). Such hydrophobic interaction matrices include, but are not limited to, natural or artificial surfaces containing uncharged groups, such as methyl, ethyl, or other alkyl groups. These groups form hydrophobic bonds with proteins which are passed through the matrix and result in separation of polynucleotides and/or polypeptides based on the strength of interaction between the polynucleotides and/or polypeptides and matrix groups. The degree of hydrophobicity of the resin material may vary depending on the concentration of salt in the medium or the concentration of salt in the eluent. Hydrophobic interaction columns normally comprise a base matrix (e.g., cross-linked agarose or synthetic copolymer material) to which hydrophobic ligands (e.g., alkyl or aryl groups) are coupled. Preferred hydrophobic interaction chromatography resins generally include alkyl moieties of 2 to 20 carbon atoms in length (e.g., 4 to 18 carbon atoms, or 6 to 15 carbon atoms), which are typically unsubstituted.

The pore diameter of the base material for hydrophobic interaction chromatography is generally between 500 to 4000 Å, but it can be appropriately selected from said range depending on the molecular size of sample to be separated and the components thereof. In general, since the retention of nucleic acids on the packing material and the adsorption capacity may differ depending on the pore diameter, it may be preferable to use a base material with a relatively large pore diameter for nucleic acids with relatively large molecular size and a base material with relatively small pore diameter for nucleic acids with a relatively small molecular size.

Hydrophobic interaction chromatography can be performed at low or high pressures, wherein the column is equilibrated in the presence of aqueous buffers using relatively high salt concentrations (e.g., 1.2 to 1.7 M ammonium sulfate) and eluted in the presence of aqueous buffers using relatively low salt concentrations (e.g., a decreasing ammonium sulfate gradient from 1.2 M to 0.5 M). As such, polynucleotides and polypeptides are selectively eluted based on the differing strengths of hydrophobic interaction with the hydrophobic groups on the matrix, i.e., in order of increasing hydrophobicity of the protein. Examples of commercially available hydrophobic interaction matrices for relatively low pressure applications include phenyl-SEPHAROSE (Pharmacia) and butyl, phenyl and ether TOYOPEARL 650 series resins (Toso Haas). Other commercially available hydrophobic interaction chromatography resins include Phenyl SEPHAROSE 6 FAST FLOW™ column with low or high substitution (Pharmacia LKB Biotechnology, AB, Sweden); Phenyl SEPHAROSE™ High Performance column (Pharmacia LKB Biotechnology, AB, Sweden); Octyl SEPHAROSE™ High Performance column (Pharmacia LKB Biotechnology, AB, Sweden); FRACTOGEL™ EMD Propyl or FRACTOGEL™ EMD Phenyl columns (E. Merck, Germany); MACRO-PREP™ Methyl or MACRO-PREP™ t-Butyl Supports (Bio-Rad, California); and WP HI-Propyl (C 3)™ column (J. T. Baker, New Jersey). Still other commercially available hydrophobic interaction chromatography resins are available from Sigma-Aldrich, Inc (St. Louis, Mo.) (e.g., TSK-GEL® Butyl-NPR; TSK-GEL® Ether-5PW; TSK-GEL® Phenyl-5PW; each of which and others may have various particle sizes); GE Healthcare (Piscataway, N.J.) (e.g., HiScreen Phenyl FF (high or low sub); HiScreen Butyl FF; HiScreen Butyl-S FF; HiScreen Octyl FF).

Elution from the hydrophobic interaction matrix can be performed with a step-wise or linear gradient. Suitable elution buffers are well known in the art. Suitable column sizes are described above in connection with the ion exchange chromatography materials. Likewise, the support matrices for the hydrophobic interaction chromatographic materials disclosed herein are not critical, however, support matrices based on dextran, cellulose, cross-linked agarose, synthetic organic polymers, coated silica or agarose are conventional in the art and suitable for use herein.

Synthesis of base materials for hydrophobic interaction chromatography, as well as process for preparing, polymerizing and functionalizing hydrophobic interaction chromatography and eluting and separating samples such as plasmid DNA therethrough are well known in the art, and are inter alia described in U.S. Pat. No. 6,441,160 and U.S. Pat. No. 7,169, 917 (each of which is hereby incorporated by reference herein in its entirety).

Filtration

According to certain preferred embodiments, one or more filtration, ultrafiltration, or diafiltration steps may also be performed, including tangential flow filtration. Filtration through size exclusion filters can be used to at least partially remove endotoxin and other contaminants while resulting in minimal nucleic acid loss. For many applications, for example, it will be desirable to further purify the sample (e.g., plasmid DNA), lower the salt concentration of the resulting sample, concentrate the sample, and/or exchange the buffer to a more suitable buffer for subsequent uses. For therapeutic uses, e.g. use in gene therapy, it may be desirable to further purify the nucleic acid obtained from the tangential flow filtration, or other, step.

One or more (initial or final) filtration, ultrafiltration, or diafiltration steps may be performed to generally achieve that result(s). If desired, a smaller MWCO ultrafiltration membrane may be used for subsequent or final diafiltration steps than used previously for initial purification, since the nucleic acid will typically be highly purified at later stages and predominantly small solute molecules will be passed through the membrane into the filtrate. For many plasmid DNAs, for example, a 10,000 to 100,000 MWCO membrane, or greater may be used. Hollow fiber devices with about a 100,000 MWCO membrane are commonly used, particularly when handling concentrated nucleic acid solutions, due to smaller hold-up volumes, increased flux, higher yields and shorter processing times. Standard, commercially available filtration and diafiltration materials are suitable for use in this process, according to standard techniques known in the art.

Filtration of fine particle size contaminants from fluids has been accomplished by the use of various porous filter media through which a contaminated composition is passed such that the filter retains the contaminant. Retention of the contaminant may occur by mechanical straining or electrokinetic particle capture and adsorption. In mechanical straining, a particle is retained by physical entrapment when it attempts to pass through a pore smaller than itself. In the case of electrokinetic capture mechanisms, the particle collides with a surface within the porous filter and is retained on the surface by short-range attractive forces. To achieve electrokinetic capture, charge-modifying systems can be used to alter the surface charge characteristics of a filter (see, e.g., WO 90/11814). For example, where the contaminant to be removed is anionic, a cationic charge modifier can be used to alter the charge characteristics of the filter such that the contaminant is retained by the filter.

In certain embodiments, either before or after filtration, the sample is treated with an aqueous solution comprising a zwitterionic detergent. Suitable zwittergents include, for example, EMPIGEN BB® (n-dodecyl-N,Ndimethylglycine), ZWITTERGENT® 3-08, ZWITTERGENT® 3-10, ZWITTERGENT® 3-12, ZWITTERGENT® 3-14, ZWITTERGENT® 3-16, CHAPS, CHAPSO, and others.

In one preferred embodiment, the sample is filtered using tangential flow filtration. The principles, theory and devices used for tangential flow filtration are described in Michaels, S. L. et al., "Tangential Flow Filtration" in Separations Technology, Pharmaceutical and Biotechnology Applications, W. P. Olson, ed., Interpharm Press, Inc., Buffalo Grove, Ill. (1995). To filter and concentrate a sample by tangential flow filtration, for example, a membrane is generally selected with a molecular weight cut off (MWCO) that is substantially lower than the molecular weight of the molecules to be retained. A general rule is to select a membrane with a molecular weight cut off that is 3 to 6 times lower than the molecular weight of the molecules to be retained. The membrane is installed, the tangential flow filtration system is initialized (typically flushed with water and tested for water filtrate flow rate and integrity), sample is added, a crossflow is established, feed and retentate pressures are set, and filtrate is collected. When the desired concentration or volume is reached, the process is stopped, and the sample is recovered.

One preferred filtration method is diafiltration using an ultrafiltration membrane having a molecular weight cutoff in the range of 30,000 to 500,000 MWCO, depending on the plasmid size. This step of diafiltration allows for buffer exchange, followed by concentration. The eluate is typically concentrated 3- to 4-fold by tangential flow filtration as described above using, for example, 30 kDa membrane cutoff, to a target concentration, and the concentrate is buffer exchanged by diafiltration at constant volume and adjusted to the target plasmid concentration. The resulting plasmid DNA solution may then be further filtered, e.g., through a 0.2 μm filter, and is typically divided into several aliquots, which are stored in containers at a relatively cold temperature (e.g., ~0° C.) until further processing.

Additionally or alternatively, the filter may be one which binds nucleic acid while allowing endotoxins and other contaminants to pass through the filter. Once the undesirable materials have passed through the filter, the nucleic acid may be eluted from the filter and collected.

Suitable size exclusion filters are available from a variety of commercial sources including, e.g., Ambion (Austin, Tex.), GE Healthcare (Piscataway, N.J.), Gelman (Ann Arbor, Mich.), Pall-Filtron (East Hills, N.Y.), Roche (Basel, Switzerland), Sartorius (Edgewood, N.Y.), and Thermo Scientific Pierce (Rockford, Ill.). The filter used will be one that binds endotoxin and other contaminants while allowing nucleic acid to pass through. Pall Ultipor® $N_{66}$® filters have been found to remove substantial endotoxin with high yield of nucleic acid. The lysate solution or lysate derivative containing the nucleic acid may also be pre-filtered (e.g., using a 0.45 μm filter) prior to one or more of the chromatography or filtration steps described herein.

Where DNA purified according to the above protocol is to be complexed with a lipid carrier for use in gene therapy, for example, it may also be desirable to exchange the DNA into a low conductivity buffer, preferably by diafiltration. A low-conductivity buffer is meant to include any buffer of less than about 10 mS, preferably less than about 1 mS.

In addition to the filtration techniques described above, conventional gel filtration methods (i.e., using a size exclusion chromatography material) may be employed. See, e.g., Gel Filtration Principles and Methods, Edition AI, Amersham Biosciences, 2002.

The polypeptides described herein may additionally or alternatively used in a variety of industrial processes requiring or benefiting from the digestion of colanic acid and other polysaccharides. In general, this may involve treating machinery, product and/or effluent pipelines, and the products, intermediates, or effluents themselves with the polypeptides described herein in order to, for instance, remove or prevent corrosion, fouling, or other build-up resulting from these industrial processes. One particular example is the removal or prevention of biofilms (e.g., those containing bacteria, such as gram negative bacterial) that may form during the processes or over time; biofilms and similar materials can constrict or block passageways and conduits, or increase wear-and-tear on machinery parts or systems. Representative industrial processes that may benefit from use of the polypeptides described herein include, for example, in paper and cellulose-making processes, membrane reconstitution and cleaning, recycling, waste-water treatments (e.g., digestions of aerobic solids and sludges), petrochemical refining and waste remediation, high purity water filtration and systems, water cooling systems/heat exchangers, and food processing. For paper or cellulose processing operations, for example, biofilms may form in intermediate processing streams, which can adversely influence downstream processing and/or affect the quality of the final product. The polypeptides described herein may benefit such processes by removing, minimizing, or preventing such biofilms.

Polypeptides

As noted above, the present invention relates to polypeptides that are capable of degrading colanic acid that may be found, for example, in biological materials. This may include, for example, biofilms or bacterial nucleic acid preparations derived from bacteria such as *E. coli, Salmonella*, or other enterobacteriaceae, such as plasmid DNA derived from *E. coli*. The polypeptides described herein also advantageously enable the preparation of highly pure gram negative bacterial plasmid DNA preparations.

In certain embodiments, the polypeptide comprises an amino acid sequence generally corresponding to SEQ ID NO: 1, and conservative amino acid substitutions thereof. This polypeptide generally corresponds to a full-length colanic acid-degrading polypeptide having a molecular weight of about 84,354 Daltons. In general, the polypeptide is an isolated polypeptide. In certain embodiments, the polypeptide is isolated from a bacterial source organism and purified. Typically, the polypeptide has a purity of at least 70%, more preferably at least 80%, more preferably at least 90%, more preferably at least 95%, more preferably at least 98%, and more preferably at least 99%.

Polypeptide fragments are also provided herein. Such fragments may be truncated at the N-terminus or C-terminus, or may lack internal residues, for example, when compared with a full-length protein. For example, certain fragments lack amino acid residues that are not essential for a desired activity (e.g., biological or otherwise) of the polypeptide. In one particular, embodiment, the polypeptide comprises an amino acid sequence generally corresponding to SEQ ID NO: 2, and conservative amino acid substitutions thereof. This polypeptide generally corresponds to a truncated version of the full-length polypeptide, wherein the first 106 amino acids of the full-length polypeptide (SEQ ID NO: 1) are absent.

In addition to the full-length and truncated polypeptides described herein, it is contemplated that polypeptide variants can be prepared, e.g., by introducing appropriate nucleotide changes to the polypeptide DNA, and/or by synthesis of the desired polypeptide, or by isolating and purifying a variant polypeptide having colanic acid-degrading activity. Those skilled in the art will appreciate that amino acid changes may alter certain post-translational processes of the polypeptide, such as changing the number or position of glycosylation sites or altering membrane anchoring characteristics.

Variations in the full-length and/or truncated sequences or in various domains of the polypeptides described herein, can be made, for example, using any of the techniques and guidelines for conservative and non-conservative mutations set forth in the literature (for example, U.S. Pat. No. 5,364,934 (hereby incorporated by reference herein in its entirety)). Variations may be a substitution, deletion or insertion of one or more codons encoding the polypeptide that results in a change in the amino acid sequence of the polypeptide as compared with the native sequence polypeptide. Optionally the variation is by substitution of at least one amino acid with any other amino acid in one or more of the domains of the polypeptide. Guidance in determining which amino acid residue may be inserted, substituted or deleted without adversely affecting the desired activity may be found by comparing the sequence of the polypeptide with that of homologous protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids, 5 to 10 amino acids, 10 to 25 amino acids, 25 to 50 amino acids, or more, such as 100 amino acids or more. The variation allowed may be determined by systematically making insertions, deletions or substitutions of amino acids in the sequence and testing the resulting variants for activity exhibited by the full-length or mature native sequence.

As noted above, the polypeptide may be a variant of the full-length or truncated polypeptide described herein. Ordinarily, a polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length polypeptide sequence as disclosed herein (e.g., SEQ ID NO: 1).

For truncated polypeptide variants, the polypeptide variant will ordinarily have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a truncated polypeptide sequence as disclosed herein (e.g., SEQ ID NO: 2).

In one embodiment, the polypeptide comprises an amino acid sequence having at least about 90% amino acid sequence identity to SEQ ID NO: 1, and conservative amino acid substitutions thereof. In another embodiment, the polypeptide comprises an amino acid sequence having at least about 95% amino acid sequence identity to SEQ ID NO: 1, and conservative amino acid substitutions thereof. In another embodiment, the polypeptide comprises an amino acid sequence having at least about 98% amino acid sequence identity to SEQ ID NO: 1, and conservative amino acid substitutions thereof. In another embodiment, the polypeptide comprises an amino acid sequence having at least about 99% amino acid sequence identity to SEQ ID NO: 1, and conservative amino acid substitutions thereof.

In one embodiment, the polypeptide comprises an amino acid sequence having at least about 90% amino acid sequence identity to SEQ ID NO: 2, and conservative amino acid substitutions thereof. In another embodiment, the polypeptide comprises an amino acid sequence having at least about 95% amino acid sequence identity to SEQ ID NO: 2, and conservative amino acid substitutions thereof. In another embodiment, the polypeptide comprises an amino acid sequence having at least about 98% amino acid sequence identity to SEQ ID NO: 2, and conservative amino acid substitutions thereof. In another embodiment, the polypeptide comprises an amino acid sequence having at least about 99% amino acid sequence identity to SEQ ID NO: 2, and conservative amino acid substitutions thereof.

In certain embodiments, exemplary conservative substitutions of interest are shown in Table 1. If such substitutions result in a change in biological activity, or a reduction in the desired activity, then more other changes, such as those described below in reference to amino acid classes, may be introduced and the products screened. It is understood that codons capable of coding for such conservative substitutions are known in the art.

TABLE 1

| Original Residue | Conservative Substitutions |
|---|---|
| Ala (A) | Ser; Val; Leu; Ile |
| Arg (R) | Lys; Gln; Asn |
| Asn (N) | Gln; His; Lys; Arg |
| Asp (D) | Glu |
| Cys (C) | Ser; Ala |
| Gln (Q) | Asn |
| Glu (E) | Asp |
| Gly (G) | Pro; Ala |
| His (H) | Asn; Gln; Lys; Arg |
| Ile (I) | Leu; Val; Met; Ala; Phe; Norleucine |
| Leu (L) | Ile; Val; Met; Ala; Phe; Norleucine |
| Lys (K) | Arg; Gln; Glu; Asn |
| Met (M) | Leu; Ile; Phe |
| Phe (F) | Leu; Val; Ile; Ala; Met; Tyr |
| Pro (P) | Ala |
| Ser (S) | Thr |
| Thr (T) | Ser |
| Trp (W) | Tyr; Phe |
| Tyr (Y) | Trp; Phe; Thr; Ser |
| Val (V) | Ile; Leu; Met; Phe; Ala; Norleucine |

Within the scope of the present invention is polypeptide analogs of the invention arrived at by amino acid substitutions based on the relative similarity of the amino acid side-chain substituents, for example, their hydrophobicity, hydrophilicity, charge, size, etc. One factor that can be considered in making amino acid substitutions is the hydropathic index of amino acids. The importance of the hydropathic amino acid index in conferring interactive biological function on a protein has been discussed by Kyte and Doolittle (J. Mol. Biol., 157: 105-132, 1982). It is accepted that the relative hydropathic character of amino acids contributes to the secondary structure of the resultant protein. This, in turn, affects the interaction of the protein with molecules such as enzymes, substrates, receptors, DNA, antibodies, antigens, etc.

Based on its hydrophobicity and charge characteristics, each amino acid has been assigned a hydropathic index as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

As is known in the art, certain amino acids in a peptide or protein can be substituted for other amino acids having a similar hydropathic index or score and produce a resultant peptide or protein having similar biological activity, i.e., which still retains biological functionality. In making such changes, it is preferable that amino acids having hydropathic indices within ±2 are substituted for one another. More preferred substitutions are those wherein the amino acids have hydropathic indices within ±1. Most preferred substitutions are those wherein the amino acids have hydropathic indices within ±0.5.

Like amino acids can also be substituted on the basis of hydrophilicity. U.S. Pat. No. 4,554,101 discloses that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4). Thus, one amino acid in a peptide, polypeptide, or protein can be substituted by another amino acid having a similar hydrophilicity score and still produce a resultant protein having similar biological activity, i.e., still retaining correct biological function. In making such changes, amino acids having hydropathic indices within ±2 are preferably substituted for one another, those within ±1 are more preferred, and those within ±0.5 are most preferred.

Substantial or minor modifications in function or biological or other identity of the polypeptides of the invention are also accomplished by selecting substitutions that differ significantly in their effect on maintaining, among other things: (a) the structure of the polypeptide backbone in the area of the substitution, for example, as a sheet or helical conformation; (b) the charge or hydrophobicity of the molecule at the target site; or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gln, his, lys, arg; (5) residues that influence chain orientation: gly, pro; and (6) aromatic: trp, tyr, phe.

Non-conservative substitutions will generally entail exchanging a member of one of these classes for another class. Such substituted residues also may be introduced into the conservative substitution sites or, more preferably, into the remaining (non-conserved) sites.

In one embodiment, for example, in the amino acid sequences described in SEQ ID NO: 1, 2, 3, 4, 5, and/or 6, the amino acid leucine (L) may alternatively be either leucine (L) or isoleucine (I), the amino acid aspartic acid (D) may alternatively be aspartic acid (D) or asparagine (N), the amino acid glutamine (Q) may alternatively be glutamine (Q) or lysine (K), and the amino acid phenylalanine (F) may alternatively be phenylalanine (F) or oxidized methionine.

The variations can be made using methods known in the art, such as alanine scanning, oligonucleotide-mediated (site-directed) mutagenesis, and PCR mutagenesis, among other known techniques. Site-directed mutagenesis, for example, (see, e.g., Carter et al., Nucl. Acids Res., 13:4331 (1986); Zoller et al., Nucl. Acids Res., 10:6487 (1987)), cassette mutagenesis (see, e.g., Wells et al., Gene, 34:315 (1985)), restriction selection mutagenesis (see, e.g., Wells et al., Philos. Trans. R. Soc. London SerA, 317:415 (1986)) or other known techniques can be performed on cloned DNA to produce the CAE variant DNA. Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant (see, e.g., Cunningham and Wells, Science, 244: 1081 1085 (1989)). Alanine is also typically preferred because it is the most common amino acid. Further, it is frequently found in both buried and exposed positions (see Creighton, The Proteins, (W.H. Freeman & Co., N.Y.); Chothia, J. Mol. Biol., 150:1 (1976)). If alanine substitution does not yield adequate amounts of variant, or the colanic acid-degrading ability of the resulting polypeptide is diminished or non-existent, another amino acid can be used.

Covalent modifications of the polypeptides described herein are also included within the scope of this invention. One type of covalent modification, for example, includes reacting targeted amino acid residues of a polypeptide with an organic derivatizing agent that is capable of reacting with selected side chains or the N- or C-terminal residues of the polypeptide. Derivatization with bifunctional agents is useful, for instance, for crosslinking the polypeptide(s) to a water-insoluble support matrix or surface for use in the method for purifying anti-CAE antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate. In one particular embodiment, the C-terminal isoleucine of certain polypeptides described herein can be removed or deleted to expose a terminal tyrosine which can be used, for example, to crosslink the polypeptide to an insoluble matrix, either directly or through a spacer, to form an affinity resin or immobilized resin.

Other modifications include, for instance, deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and/or histidine side chains (see, e.g., T. E. Creighton, Proteins: Structure and Molecular Properties, W.H. Freeman & Co., San Francisco, pp. 79 86 (1983)), acetylation of the N-terminal amine, and amidation of any C-terminal carboxyl group.

Another type of covalent modification of the polypeptides described herein and included within the scope of this invention comprises altering the native glycosylation pattern of the polypeptide. In general, altering the native glycosylation pattern involves deleting one or more carbohydrate moieties found in the polypeptide (e.g., the full-length) sequence (either by removing the underlying glycosylation site or by deleting the glycosylation by chemical and/or enzymatic means), and/or adding one or more glycosylation sites that are not present in the polypeptide sequence. In addition, this may include qualitative changes in the glycosylation of the native proteins, involving a corresponding change in the nature and proportions of the various carbohydrate moieties that may be present.

Addition of glycosylation sites to the polypeptide of the invention may be accomplished by altering the amino acid sequence. The alteration may be made, for example, by the addition of, or substitution by, one or more serine or threonine residues to the polypeptide sequence (for O-linked glycosylation sites). The amino acid sequences described herein (e.g., SEQ ID NO. 1, SEQ ID NO. 2, etc.) may optionally be altered through changes at the DNA level, particularly by mutating the DNA encoding the polypeptide at preselected bases such that codons are generated that will translate into the desired amino acids.

Another means of increasing the number of carbohydrate moieties on the polypeptide is by chemical or enzymatic coupling of glycosides to the polypeptide. Such methods are generally described in the art, e.g., in PCT International Pub. No. WO 87/05330, and in Aplin and Wriston, CRC Crit. Rev. Biochem., pp. 259 306 (1981).

Removal of carbohydrate moieties present on the polypeptides described herein may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification comprises linking the polypeptides described herein to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337 (each of which is hereby incorporated by reference herein).

Additionally or alternatively, the polypeptides of the present invention may also be modified in a way to form a chimeric molecule comprising the polypeptide fused to another, heterologous polypeptide or amino acid sequence. The polypeptides may also be labeled with reagents that facilitate their detection. For example, the agents may be combined with fluorescent labels (e.g., Prober et al., Science 238:336-340 (1987); Albarella et al., EP 0 144 914); chemical labels (e.g., Sheldon et al., U.S. Pat. No. 4,582,789; Albarella et al., U.S. Pat. No. 4,563,417); and/or modified bases (e.g., Miyoshi et al., EP 0 119 448) (each of which are hereby incorporated by reference in their entirety).

In one embodiment, such a chimeric molecule comprises a fusion of the polypeptide with a tag polypeptide which provides an epitope to which an anti-tag antibody can selectively bind. The epitope tag is generally placed at the amino- or carboxyl-terminus of the polypeptide amino acid sequence. The presence of such epitope-tagged forms of the polypeptide can be detected using an antibody against the tag polypeptide. Also, provision of the epitope tag enables the polypeptide to be readily purified by affinity purification using an anti-tag antibody or another type of affinity matrix that binds to the epitope tag. Various tag polypeptides and their respective antibodies are well known in the art. Examples include the c-myc tag and the 8F9, 3C7, 6E10, G4, B7 and 9E10 antibodies thereto (see, e.g., Evan et al., Molecular and Cellular Biology, 5:3610 3616 (1985)); the flu HA tag polypeptide and its antibody 12 CA5 (see, e.g., Field et al., Mol. Cell. Biol., 8:2159 2165 (1988)); the Herpes Simplex virus glycoprotein D (gD) tag and its antibody (see, e.g., Paborsky et al., Protein Engineering, 3(6):547 553 (1990)); and poly-histidine (poly-his) or poly-histidine-glycine (poly-his-gly) tags. Other tag polypeptides include an α-tubulin epitope peptide (see, e.g., Skinner et al., J. Biol. Chem., 266:15163 15166 (1991)); the FLAG®-peptide (Sigma-Aldrich, Inc. (St. Louis, Mo.); see also Hopp et al., BioTechnology, 6:1204 1210 (1988)); the KT3 epitope peptide (see, e.g., Martin et al., Science, 255:192 194 (1992)); and the T7 gene 10 protein peptide tag (Lutz-Freyermuth et al., Proc. Natl. Acad. Sci. USA, 87:6393 6397 (1990)).

To facilitate isolation and/or purification, for example, an amino acid tag can be added to the polypeptides described herein using genetic engineering techniques that are well known to practitioners of the art. In certain embodiments, for example, the polypeptide(s) may include one, and more preferably six, consecutive histidine residues at either the amino or carboxy terminus of the protein. Such consecutive histidine residues are commonly referred to as a histidine tag. Terminal consecutive histidine residues can facilitate detection and/or purification of expressed recombinant proteins, and generally do not interfere with the function/activity/structure of the protein. The consecutive histidine residues can be incorporated into the protein coding gene by primers that carry the 5'-CAT-3' triplets. Consecutive histidine residues at either terminus serve as convenient aids for purification of proteins with immobilized metal affinity chromatography, which exploits the ability of the amino acid histidine to bind chelated transition metal ions such as nickel ($Ni^{2+}$), zinc ($Zn^{2+}$) and copper ($Cu^{2+}$). As noted above, other techniques include, but are not limited to, epitopes for polyclonal or monoclonal antibodies including but not limited to the T7 epitope, the myc epitope, and the V5a epitope; and fusion of the polypeptides described herein to suitable protein partners including but not limited to glutathione-S-transferase or maltose binding protein. In a particular embodiment, the amino acid sequence comprises an affinity tag allowing for, e.g., isolation and purification of the protein, such as, for example, a GST tag, a His tag, a FLAG® tag, or an XPRESS™ tag; in certain preferred embodiments, the affinity tag comprises a His tag (i.e., one or more, and preferably six histidine residues) (see, e.g., SEQ ID NO: 3 or SEQ ID NO: 4), one or more copies of the FLAG® octapeptide (DYKDDDDK) (see, e.g., SEQ ID NO: 5), or the XPRESS™ octapeptide (DLYDDDDK). These additional amino acid sequences can be added to the C-terminus of the polypeptides, as well as the N-terminus, or at intervening positions within the polypeptides.

In an alternative embodiment, the chimeric molecule may comprise a fusion of the polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a polypeptide in place of at least one variable region within an Ig molecule. In a particular embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130; U.S. Pat. No. 6,165,476; U.S. Pat. No. 6,444,792; U.S. Pat. No. 7,442,778; and U.S. Pat. No. 7,465,447 (each of which is hereby incorporated by reference herein in its entirety).

Preparation of Polypeptides

Full-length polypeptides (including, for example, the polypeptide comprising the amino acid sequence corresponding to SEQ ID NO: 1) and polypeptide fragments (including, for example, the truncated polypeptide comprising the amino acid sequence corresponding to SEQ ID NO: 2) may be prepared by any of a number of conventional techniques. The polypeptides of the invention may be prepared, in general, by culturing host cells transformed or transfected with a vector containing polynucleotides encoding the desired polypeptide. In certain embodiments, the vector is selected from a plasmid, a virus, and a bacteriophage; more preferably in this embodiment, the vector is a bacteriophage (see, e.g., Example 2). Methods of preparing vectors, and in particular phage, for the production of polypeptides are well known in the art.

Generally, host cells, such as bacteria, are transfected or transformed with expression or cloning vectors described herein for polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated, and electroporation. Depending on the host cell used, transformation is performed using standard techniques appropriate to such cells. The calcium treatment employing calcium chloride, as described in Sambrook et al., supra, or electroporation, for example, is generally used for prokaryotes. Infection with Agrobacterium tumefaciens is used for transformation of certain plant cells, as described by Shaw et al., Gene, 23:315 (1983) and PCT International Pub. No. WO 89/05859. For mammalian cells without such cell walls, the calcium phosphate precipitation method of Graham and van der Eb, Virology, 52:456 457 (1978) can be employed. General aspects of mammalian cell host system transfections have likewise been described in U.S. Pat. No. 4,399,216 (hereby incorporated by reference herein in its entirety). Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., Methods in Enzymology, 185:527 537 (1990) and Mansour et al., Nature, 336:348 352 (1988).

Suitable host cells for cloning or expressing the DNA in the vectors herein include prokaryote, yeast, or higher eukaryote cells. Suitable prokaryotes include but are not limited Enterobacteriaceae such as Escherichia, e.g., E. coli, Enterobacter, Erwinia, Klebsiella, Proteus, Salmonella, e.g., Salmonella typhimurium, Serratia, e.g., Serratia marcescans, and Shigella, as well as Bacilli such as B. subtilis and B. licheniformis (e.g., B. licheniformis 41P disclosed in DD 266,710), Pseudomonas such as P. aeruginosa, and Streptomyces. Preferably, the host cell secretes minimal amounts of proteolytic enzymes. For example, the strain may be modified to effect a genetic mutation in the genes encoding proteins endogenous to the host (see, e.g., U.S. Pat. No. 4,946,783). Alternatively, in vitro methods of cloning, e.g., PCR or other nucleic acid polymerase reactions, are suitable.

Preferred host cells for producing polypeptides of the invention are prokaryotes, and more preferably bacteria, including eubacteria and archaebacteria. Preferred of these are eubacteria, including gram-positive and gram-negative bacteria. More preferred are gram-negative bacteria. One preferred type of bacteria is Enterobacteriaceae. Examples of bacteria belonging to Enterobacteriaceae include Escherichia, Enterobacter, Erwinia, Klebsiella, Proteus, Salmonella, Serratia, and Shigella. Other types of suitable bacteria include Azotobacter, Pseudomonas, Rhizobia, Vitreoscilla, and Paracoccus. E. coli is particularly preferred herein.

Prokaryotic cells used to produce the polypeptides of the invention are grown in media known in the art and suitable for culture of the selected host cells, including the media generally described by Sambrook et al., supra. Media that are suitable for bacteria include, but are not limited to, AP5 medium, nutrient broth, Luria-Bertani (LB) broth, Neidhardt's minimal medium, and C.R.A.P. minimal or complete medium (see, e.g., U.S. Pat. No. 6,828,121), plus necessary nutrient supplements. The media may also contains a selection agent, chosen based on the construction of the expression vector, to selectively permit growth of prokaryotic cells containing the expression vector. For example, ampicillin is added to media for growth of cells expressing ampicillin resistant gene. Any necessary supplements besides carbon, nitrogen, and inorganic phosphate sources may also be included at appropriate concentrations introduced alone or as a mixture with another supplement or medium such as a complex nitrogen source. The culture medium may also optionally contain one or more reducing agents selected from the group consisting of glutathione, cysteine, cystamine, thioglycollate, dithioerythritol, and dithiothreitol. The prokaryotic host cells are cultured at suitable temperatures. For E. coli growth, for example, the preferred temperature ranges from about 20° C. to about 39° C., more preferably from about 25° C. to about 37° C., even more preferably at about 30° C. Any necessary supplements may also be included at appropriate concentrations that would be known to those skilled in the art, introduced alone or as a mixture with another supplement or medium such as a complex nitrogen source. The pH of the medium may be any pH from about 5.9, depending mainly on the host organism. For E. coli, the pH is preferably from about 6.8 to about 7.4, and more preferably about 7.0.

In addition to prokaryotes, eukaryotic microbes such as filamentous fungi or yeast are suitable cloning or expression hosts for polypeptide-encoding vectors. Saccharomyces cerevisiae is a commonly used lower eukaryotic host microorganism. Other conventional host microorganisms include filamentous fungi such as, e.g., Neurospora, Penicillium, Tolypocladium (WO 91/00357), and Aspergillus hosts such as A. nidulans (Ballance et al., Biochem. Biophys. Res. Commun, 112:284 289 (1983); Tilburn et al., Gene, 26:205 221 (1983); Yelton et al., Proc. Natl. Acad. Sci. USA, 81: 1470 1474 (1984)) and A. niger (Kelly and Hynes, EMBO J., 4:475 479 (1985)); Kluyveromyces hosts (U.S. Pat. No. 4,943,529; Fleer et al., Bio/Technology, 9:968 975 (1991)) such as, e.g., K. lactis (MW98-8C, CBS683, CBS4574; Louvencourt et al., J. Bacteriol., 154(2):737 742 (1983)), K. fragilis (ATCC 12,424), K. bulgaricus (ATCC 16,045), K. wickeramii (ATCC 24,178), K. waltii (ATCC 56,500), K. drosophilarum (ATCC 36,906; Van den Berg et al., Bio/Technology, 8:135 (1990)), K. thermotolerans, and K. marxianus; yarrowia (EP 0 402 226); Pichia pastoris (EP 0 183 070; Sreekrishna et al., J. Basic Microbiol., 28:265 278 (1988)); Candida; Trichoderma reesia (EP 0 244 234); Neurospora crassa (Case et al., Proc. Natl. Acad. Sci. USA, 76:5259 5263 (1979));

*Schizosaccharomyces pombe* (Beach and Nurse, Nature, 290: 140 (1981); EP 0 139 383); and *Schwanniomyces* such as *Schwanniomyces occidentalis* (EP 0 394 538).

Methylotropic yeasts are also suitable and include, but are not limited to, yeast capable of growth on methanol selected from the genera consisting of *Hansenula, Candida, Kloeckera, Pichia, Saccharomyces, Torulopsis*, and *Rhodotorula*. Representative species that are exemplary of this class of yeasts may be found in C. Anthony, The Biochemistry of Methylotrophs, 269 (1982).

Suitable host cells for the expression of glycosylated polypeptides are generally derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include Chinese hamster ovary cells/–DHFR (CHO, Urlaub and Chasin, Proc. Natl. Acad. Sci. USA, 77:4216 (1980)); human embryonic kidney line (293 or 293 cells subcloned for growth in suspension culture, Graham et al., J. Gen Virol., 36:59 (1977)); human liver cells (Hep G2, HB 8065); human lung cells (W138, ATCC CCL 75); monkey kidney CV1 line transformed by SV40 (COS-7, ATCC CRL 1651); mouse sertoli cells (TM4, Mather, Biol. Reprod., 23:243 251 (1980)); and mouse mammary tumor (MMT 060562, ATCC CCL51), among others. The selection of the appropriate host cell is deemed to be within the skill in the art.

Once identified, the nucleic acid (e.g., cDNA or genomic DNA) encoding the target polypeptide may be inserted into a replicable vector for cloning (amplification of the DNA) or for expression, and various vectors are publicly available. The vector may, for example, be in the form of a cosmid, plasmid, phage, or viral particle. Many vectors are available for this purpose, and selection of the appropriate vector will depend mainly on the size of the nucleic acid to be inserted into the vector and the particular host cell to be transformed with the vector. The appropriate nucleic acid sequence (such as described below may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the polypeptide-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion, for example, the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 0 362 179), or the signal described in PCT International Pub. No. WO 90/13646. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors may also contain a selection gene, also referred to in the art as a selectable marker. Typical selection genes encode proteins that: (a) complement auxotrophic deficiencies; (b) confer resistance to antibiotics or other drugs or toxins, e.g., ampicillin, G418, hygromycin, neomycin, methotrexate, or tetracycline; or (c) supply critical nutrients not available from complex media, e.g., the gene encoding D-alanine racemase for Bacilli.

One example of suitable selectable markers for mammalian cells are those that enable the identification of cells competent to take up the colanic acid-degrading polypeptide-encoding nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980). A suitable selection gene for use in yeast is the trp1 gene present in the yeast plasmid YRp7 (see, e.g., Stinchcomb et al., Nature, 282:39 (1979); Kingsman et al., Gene, 7:141 (1979); Tschemper et al., Gene, 10:157 (1980). The trp1 gene provides a selection marker for a mutant strain of yeast lacking the ability to grow in tryptophan, for example, ATCC No. 44076 or PEP4-1 (see, e.g., Jones, Genetics, 85:12 (1977)).

Expression and cloning vectors usually contain a promoter operably linked to the polypeptide-encoding nucleic acid sequence to direct mRNA synthesis. Promoters recognized by a variety of potential host cells are well known. Promoters suitable for use with prokaryotic hosts include alkaline phosphatase, a tryptophan (trp) promoter system (e.g., Goeddel, Nucleic Acids Res., 8:4057 (1980); EP 0 036 776); the β-lactamase and lactose promoter systems (e.g., Chang et al., Nature, 275:615 (1978); Goeddel et al., Nature, 281:544 (1979)); and hybrid promoters such as the tac promoter (see, e.g., deBoer et al., Proc. Natl. Acad. Sci. USA, 80:21 25 (1983)). Promoters for use in bacterial systems may also contain a Shine-Dalgarno (S.D.) sequence operably linked to the DNA encoding the target polypeptide.

Examples of suitable promoting sequences for use with yeast hosts include the promoters for 3-phosphoglycerate kinase (Hitzeman et al., J. Biol. Chem., 255:2073 (1980)) or other glycolytic enzymes (Hess et al., J. Adv. Enzyme Reg., 7:149 (1968); Holland, Biochemistry, 17:4900 (1978)), such as enolase, hexokinase, glucokinase, glucose-6-phosphate isomerase, glyceraldehyde-3-phosphate dehydrogenase, phosphofructokinase, phosphoglucose isomerase, 3-phosphoglycerate mutase, pyruvate decarboxylase, pyruvate kinase, and triosephosphate isomerase. Other yeast promoters, which are inducible promoters having the additional advantage of transcription controlled by growth conditions, are the promoter regions for acid phosphatase, alcohol dehydrogenase 2, degradative enzymes associated with nitrogen metabolism, enzymes responsible for maltose and galactose utilization, glyceraldehyde-3-phosphate dehydrogenase, isocytochrome C, and metallothionein. Suitable vectors and promoters for use in yeast expression are further described in EP 0 073 657.

Target polypeptide transcription from vectors in mammalian host cells is controlled, for example, by promoters obtained from the genomes of viruses such as adenovirus (such as Adenovirus 2), avian sarcoma virus, bovine papilloma virus, cytomegalovirus, fowlpox virus (see, e.g., UK 2,211,504), hepatitis-B virus, polyoma virus, a retrovirus, and Simian Virus 40 (SV40), or from heterologous mammalian promoters (e.g., the actin promoter or an immunoglobulin promoter), and/or from heat-shock promoters, provided such promoters are compatible with the host cell systems.

Transcription of a DNA encoding the target polypeptide by higher eukaryotes may be increased in many instances by inserting an enhancer sequence into the vector. Enhancers are cis-acting elements of DNA, typically about from 10 to 300 bp, that act on a promoter to increase its transcription. Numerous enhancer sequences are known from mammalian genes (albumin, α-fetoprotein, elastase, globin, and insulin). Typically, an enhancer from a eukaryotic cell virus will be used. Non-limiting examples include the SV40 enhancer on the late side of the replication origin (bp 100 270), the cytomegalovirus early promoter enhancer, the polyoma enhancer on the late side of the replication origin, and adenovirus enhancers. The enhancer may be spliced into the vector at a position 5' or 3' to the polypeptide coding sequence, typically located at a site 5' from the promoter.

Expression vectors used in prokaryotic (e.g., bacteria) and/or eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of prokaryotic, eukaryotic, or viral DNAs or cDNAs. These regions contain nucleotide segments transcribed as polyadenylated fragments in the untranslated portion of the mRNA encoding the polypeptide of interest. Still other methods, vectors, and host cells suitable for adaptation to the synthesis of polypeptides in recombinant vertebrate cell culture are described in Gething et al., Nature, 293:620 625 (1981); Mantei et al., Nature, 281:40 46 (1979); EP 0 117 060; and EP 0 117 058.

Gene amplification and/or expression may be measured in a sample directly, for example, by conventional Southern blotting, Northern blotting to quantitate the transcription of mRNA (see, e.g., Thomas, Proc. Natl. Acad. Sci. USA, 77:5201 5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal Conveniently, the antibodies may be prepared against a full-length sequence polypeptide or against a truncated or fragment peptide based on the DNA sequences provided herein or against exogenous sequence fused to CAE DNA and encoding a specific antibody epitope.

Forms of the polypeptide may be recovered from culture medium or from host cell lysates. If membrane-bound, it can be released from the membrane using a suitable detergent solution (e.g. Triton-X 100) or by enzymatic cleavage. Cells employed in expression of polypeptides can be disrupted by various physical or chemical means, such as freeze-thaw cycling, sonication, mechanical disruption, or cell lysing agents. It may be desired to purify the polypeptide(s) from recombinant cell proteins or polypeptides. Exemplary of suitable purification procedures are ammonium sulfate precipitation; chromatofocusing; chromatography on silica or on a cation-exchange resin such as DEAE; ethanol precipitation; fractionation on an ion-exchange column; gel filtration using, for example, Sephadex G-75; metal chelating columns to bind epitope-tagged forms of the polypeptide; protein A Sepharose columns to remove contaminants such as IgG; reverse phase HPLC; and SDS-PAGE. Various methods of protein purification may be employed and such methods are known in the art and described for example in Deutscher, Methods in Enzymology, 182 (1990); Scopes, Protein Purification: Principles and Practice, Springer-Verlag, New York (1982). In general, the purification step(s) performed will depend, for example, on the nature of the production process, the particular polypeptide produced, and the downstream use(s) of the polypeptide.

Alternatively, for instance, desired peptides and fragments thereof may be chemically synthesized, or may be extracted from a natural source organism(s). Another alternative approach involves generating polypeptides and fragments thereof by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA sequence or fragment encoding a desired polypeptide or polypeptide fragment, by polymerase chain reaction (PCR). Oligonucleotides that define the desired termini of the DNA are employed at the 5' and 3' primers in the PCR. Where the polypeptide is a polypeptide fragment, the polypeptide fragment preferably shares at least one biological and/or immunological activity with the native (i.e., full-length) polypeptide disclosed herein. In certain instances, the polypeptide fragment may have greater activity than the full-length polypeptide, or may otherwise be optimized or improved relative to the full-length polypeptide.

Other alternative methods, which are well known in the art, may also be employed to prepare the polypeptides described herein. For instance, the polypeptide sequence, or portions thereof, may be produced by direct peptide synthesis using solid-phase techniques (see, e.g., Stewart et al., Solid-Phase Peptide Synthesis, W.H. Freeman Co., San Francisco, Calif. (1969); Merrifield, J. Am. Chem. Soc., 85:2149 2154 (1963)). In vitro protein synthesis may be performed using automation, or by manual techniques. Automated synthesis may be accomplished, for instance, using an Applied Biosystems Peptide Synthesizer (Foster City, Calif.) in accordance with the manufacturer's instructions. Various portions of the polypeptides described herein may be chemically synthesized separately and combined using chemical or enzymatic methods to produce the full-length, truncated, or other variant polypeptides.

Polynucleotides

Another aspect of the disclosure provides polynucleotides and fragments thereof, and partial or complete complements thereof, mRNA, and/or coding sequences, preferably in isolated form, including polynucleotides encoding a polypeptide or enzyme having colanic acid-degrading (CAE) activity and/or a CAE-related protein and fragments thereof (as described above), DNA, RNA, DNA/RNA hybrid, and related molecules, polynucleotides or oligonucleotides complementary to the polynucleotides described herein or mRNA sequence or a part thereof, and polynucleotides or oligonucleotides that hybridize to a CAE-encoding polynucleotide or mRNA of the same.

In certain embodiments, the polynucleotide comprises a nucleic acid sequence generally corresponding to SEQ ID NO: 7, and the complement thereof. In certain other embodiments, the polynucleotide comprises a nucleic acid sequence generally corresponding to SEQ ID NO: 8. Preferably, the polynucleotide is an isolated polynucleotide. In other embodiments, the polynucleotide is a recombinant polynucleotide.

Polynucleotide variants are also provided herein. Polynucleotide variants may contain one or more substitutions, additions, deletions, and/or insertions such that the activity of the polynucleotide is not substantially diminished, as described above. The effect on the activity of the polynucleotide may generally be assessed as described herein, or using conventional methods. Generally, polynucleotide variants have at least about 80% nucleic acid sequence identity with a nucleotide acid sequence encoding a full-length or truncated polypeptide having colanic acid-degrading activity, as disclosed herein or any other fragment of a full-length or truncated polypeptide sequence as disclosed herein. Variants preferably exhibit at least about 85%, 87%, 88% or 89% identity and more preferably at least about 90%, 92%, 95%, 96%, or 97% identity to a portion of a polynucleotide sequence that encodes a polypeptide having endotoxin-degrading capabilities. The percent identity may be readily determined by comparing sequences of the polynucleotides to the corresponding portion of the target polynucleotide, using any method including using computer algorithms well known to those having ordinary skill in the art, such as Align or the BLAST algorithms (see, e.g., Altschul, J. Mol. Biol. 219:555-565, 1991; Henikoff and Henikoff, Proc. Natl. Acad. Sci. USA 89:10915-10919, 1992), which is available at the NCBI website, and which are described elsewhere herein. Default parameters may be used.

Ordinarily, a variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length polypeptide sequence as disclosed herein (e.g., SEQ ID NO: 7).

For polynucleotides encoding truncated polypeptides, the polynucleotide variant will ordinarily have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a truncated polypeptide sequence as disclosed herein (e.g., SEQ ID NO: 8).

In one embodiment, the nucleic acid molecule shares at least 90% sequence identity with the nucleic acid sequence set forth in SEQ ID NO: 7. For example, the nucleic acid molecule may share at least 95% sequence identity with the nucleic acid sequence set forth in SEQ ID NO: 7, or may share at least 98% sequence identity with the nucleic acid sequence set forth in SEQ ID NO: 7. In a particular embodiment, the nucleic acid molecule has the sequence set forth in SEQ ID NO: 7; that is, the nucleic acid molecule exhibits 100% sequence identity with the nucleic acid sequence set forth in SEQ ID NO: 7.

In another embodiment, the nucleic acid molecule shares at least 90% sequence identity with the nucleic acid sequence set forth in SEQ ID NO: 8. For example, the nucleic acid molecule may share at least 95% sequence identity with the nucleic acid sequence set forth in SEQ ID NO: 8, or may share at least 98% sequence identity with the nucleic acid sequence set forth in SEQ ID NO: 8. In a particular embodiment, the nucleic acid molecule has the sequence set forth in SEQ ID NO: 8; that is, the nucleic acid molecule exhibits 100% sequence identity with the nucleic acid sequence set forth in SEQ ID NO: 8.

Certain polynucleotide and variants thereof are substantially homologous to a portion of a native gene that encodes a desired target polypeptide. Single-stranded nucleic acids derived (e.g., by thermal denaturation) from such polynucleotides and variants are capable of hybridizing under moderately stringent conditions to a naturally occurring DNA or RNA sequence encoding a native target polypeptide. A polynucleotide that detectably hybridizes under moderately stringent conditions may have a nucleotide sequence that includes at least 10 consecutive nucleotides, for example, at least 50, at least 100, at least 150, at least 200, at least 250, and least 300, at least 350, at least 400, at least 450, at least 500, or more consecutive nucleotides that are complementary to a particular target polynucleotide. In certain preferred embodiments such a sequence (or its complement) will be unique to a single particular target polypeptide for which interference with expression is desired, and in certain other embodiments the sequence (or its complement) may be shared by two or more related target polypeptides for which interference with polypeptide expression is desired.

Sequence specific polynucleotides of the present invention may be designed using one or more of several criteria. For example, to design a polynucleotide that has 10, 20, 30, 40, 50, 60, 70, 80, 90, 100, 200, 300, 400, 500, 600, or more, consecutive nucleotides identical to a sequence encoding a polypeptide of interest (e.g., a polypeptide having colanic acid-degrading activity, such as those described herein), the open reading frame of the polynucleotide sequence may be scanned for sequences that have one or more of the following characteristics: (1) an A+T/G+C ratio of approximately 1:1 but no greater than 2:1 or 1:2; (2) an AA dinucleotide or a CA dinucleotide at the 5' end; (3) an internal hairpin loop melting temperature less than 55° C.; (4) a homodimer melting temperature of less than 37° C. (melting temperature calculations as described in (3) and (4) can be determined using computer software known to those skilled in the art); (5) a sequence of at least 10-20 consecutive nucleotides not identified as being present in any other known polynucleotide sequence (such an evaluation can be readily determined using computer programs available to a skilled artisan such as BLAST to search publicly available databases). Alternatively, a polynucleotide sequence may be designed and chosen using a computer software available commercially from various vendors (e.g., OligoEngine™ (Seattle, Wash.); Dharmacon, Inc. (Lafayette, Colo.); Ambion Inc. (Austin, Tex.); and QIAGEN, Inc. (Valencia, Calif.)). See also Elbashir et al., Genes & Development 15:188-200 (2000); Elbashir et al., Nature 411:494-98 (2001). The polynucleotides of interest may then be tested for their ability to encode target polypeptides, to hybridize to other polynucleotides of interest, or to interfere with the expression of the target polypeptide according to methods known in the art, and the determination of the effectiveness of a particular polynucleotide based on these tests will be evident to one of skill in the art.

Persons having ordinary skill in the art will also readily appreciate that as a result of the degeneracy of the genetic code, many nucleotide sequences may encode a polypeptide as described herein. That is, an amino acid may be encoded by one of several different codons and a person skilled in the art can readily determine that while one particular nucleotide sequence may differ from another (which may be determined by alignment methods disclosed herein and known in the art), the sequences may encode polypeptides with identical amino acid sequences. By way of example, the amino acid leucine in a polypeptide may be encoded by one of six different codons (TTA, TTG, CTT, CTC, CTA, and CTG) as can serine (TCT, TCC, TCA, TCG, AGT, and AGC). Other amino acids, such as proline, alanine, and valine, for example, may be encoded by any one of four different codons (CCT, CCC, CCA, CCG for proline; GCT, GCC, GCA, GCG for alanine; and GTT, GTC, GTA, GTG for valine). Some of these polynucleotides bear minimal homology to the nucleotide sequence of any native gene. Nonetheless, polynucleotides that vary due to differences in codon usage are specifically contemplated by the present invention.

The polynucleotide may also comprise a codon optimized sequence; that is, a nucleotide sequence that has been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization may be generally referred to in the art as expression enhanced sequences.

The polynucleotides may also be labeled with reagents that facilitate their detection. For example, the agents may be combined with fluorescent labels (e.g., Prober et al., Science 238:336-340 (1987); Albarella et al., EP 144914); chemical labels (e.g., Sheldon et al., U.S. Pat. No. 4,582,789; Albarella et al., U.S. Pat. No. 4,563,417); and/or modified bases (e.g., Miyoshi et al., EP 0 119 448) (each of which are hereby incorporated by reference in their entirety).

Polynucleotides or fragments thereof of the present invention are also generally capable of specifically hybridizing to other nucleic acid molecules under certain circumstances. For example, two nucleic acid molecules are said to be capable of specifically hybridizing to one another if the two molecules are capable of forming an anti-parallel, double-stranded nucleic acid structure. A nucleic acid molecule or polynucleotide is said to be the complement of another nucleic acid molecule or polynucleotide if they exhibit complete complementarity. Molecules are said to exhibit complete complementarity when every nucleotide of one of the molecules is complementary to a nucleotide of the other. Two molecules are said to be minimally complementary if they can hybridize to one another with sufficient stability to permit them to remain annealed to one another under at least conventional low-stringency conditions. Similarly, the molecules are said to be complementary if they can hybridize to one another with sufficient stability to permit them to remain annealed to one another under conventional high-stringency conditions. Conventional stringency conditions are described elsewhere herein and by Sambrook et al., Molecular Cloning, A Laboratory Manual, 2nd Ed., Cold Spring Harbor Press, Cold Spring Harbor, N.Y. (1989) and by Haymes et al., Nucleic Acid Hybridization, A Practical Approach, IRL Press, Washington, D.C. (1985), each of which is herein incorporated by reference. Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

In a particular embodiment, a polynucleotide of the present invention will specifically hybridize to one or more of SEQ ID NO: 7 and SEQ ID NO: 8, or complements thereof, under moderately stringent conditions.

Preparation of Polynucleotides

Polynucleotides, including polynucleotides encoding polypeptides having colanic acid-degrading activity, may be prepared using any of a variety of techniques, which will be useful for the preparation of specifically desired polynucleotides and for the identification and selection of desirable sequences to be used in polynucleotides. For example, a polynucleotide may be amplified from cDNA prepared from a suitable bacteria, cell, or tissue type. Such polynucleotides may be amplified via polymerase chain reaction (PCR). For this approach, sequence-specific primers may be designed based on the sequences provided herein and may be purchased or synthesized. An amplified portion may be used to isolate a full-length gene, or a desired portion thereof, from a suitable library using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences. Suitable sequences for a polynucleotide contemplated by the present invention may also be selected from a library of polynucleotide sequences.

For hybridization techniques, a partial sequence may be labeled (e.g., by nick-translation or end-labeling with $^{32}P$)

using well known techniques. A bacterial or bacteriophage library may then be screened by hybridizing filters containing denatured bacterial colonies (or lawns containing phage plaques) with the labeled probe (see, e.g., Sambrook et al., Molecular Cloning: A Laboratory Manual, Cold Spring Harbor Laboratories, Cold Spring Harbor, N.Y., 2001). Hybridizing colonies or plaques are selected and expanded, and the DNA is isolated for further analysis. Clones may be analyzed to determine the amount of additional sequence by, for example, PCR using a primer from the partial sequence and a primer from the vector. Restriction maps and partial sequences may be generated to identify one or more overlapping clones. A full-length cDNA molecule can be generated by ligating suitable fragments, using well known techniques.

Alternatively, numerous amplification techniques are known in the art for obtaining a full-length coding sequence from a partial cDNA sequence. Within such techniques, amplification is generally performed via PCR. One such technique is known as rapid amplification of cDNA ends or RACE. This technique involves the use of an internal primer and an external primer, which hybridizes to a polyA region or vector sequence, to identify sequences that are 5' and 3' of a known sequence. Any of a variety of commercially available kits may be used to perform the amplification step. Primers may be designed using, for example, software well known in the art. Primers (or oligonucleotides for other uses contemplated herein, including, for example, probes and antisense oligonucleotides) are preferably 15, 16, 17, 18, 19, 20, 21, 22, 23, 24, 25, 26, 27, 28, 29, 30, 31 or 32 nucleotides in length, have a GC content of at least 40% and anneal to the target sequence at temperatures of about 54° C. to 72° C. The amplified region may be sequenced as described above, and overlapping sequences assembled into a contiguous sequence. Certain oligonucleotides contemplated by the present invention may, for some preferred embodiments, have lengths of 10, 11, 12, 13, 14, 15, 16, 17, 18, 19, 20, 21, 22, 23, 24, 25, 26, 27, 28, 29, 30, 31, 32, 33-35, 35-40, 41-45, 46-50, 56-60, 61-70, 71-80, 81-90, or more, nucleotides.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives, and cosmids. Vectors of particular interest include expression vectors, replication vectors, probe generation vectors, and sequencing vectors. In general, a suitable vector contains an origin of replication functional in at least one organism, convenient restriction endonuclease sites, and one or more selectable markers. (See, e.g., PCT International Pub. No. WO 01/96584; PCT International Pub. No. WO 01/29058; U.S. Pat. No. 6,326,193; U.S. Pub. App. No. 2002/0007051 (each of which is hereby incorporated by reference herein in its entirety). Other elements will depend upon the desired use, and will be apparent to those having ordinary skill in the art. For example, the invention contemplates the use of polynucleotide sequences in the preparation of recombinant nucleic acid constructs including vectors for the expression of a desired target polypeptide such as a CAE polypeptide; the invention also contemplates the generation of transgenic animals and cells (e.g., cells, cell clones, lines or lineages, or organisms in which expression of one or more desired polypeptides (e.g., a target polypeptide) is facilitated). Within certain embodiments, polynucleotides may be formulated so as to permit entry into a cell of a mammal, and expression therein. Such formulations are particularly useful for therapeutic purposes, as described below. Those having ordinary skill in the art will appreciate that there are many ways to achieve expression of a polynucleotide and/or polypeptide in a target cell, and any suitable method may be employed. For example, a polynucleotide may be incorporated into a viral vector using well known techniques (see also, e.g., U.S. Pub. App. No. 2003/0068821 (hereby incorporated by reference herein in its entirety)). A viral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those having ordinary skill in the art.

In other embodiments, one or more promoters may be identified, isolated and/or incorporated into recombinant nucleic acid constructs of the present invention, using standard techniques. The present invention provides nucleic acid molecules comprising such a promoter sequence or one or more cis- or trans-acting regulatory elements thereof. Such regulatory elements may enhance expression of a polynucleotide or polypeptide described herein. A 5' flanking region may be generated using standard techniques, based on the genomic sequence provided herein. If necessary, additional 5' sequences may be generated using PCR-based or other standard methods. The 5' region may be subcloned and sequenced using standard methods. Primer extension and/or RNase protection analyses may be used to verify the transcriptional start site deduced from the cDNA.

To define the boundary of the promoter region, putative promoter inserts of varying sizes may be subcloned into a heterologous expression system containing a suitable reporter gene without a promoter or enhancer. Suitable reporter genes may include genes encoding beta-galactosidase, chloramphenicol acetyl transferase, luciferase, secreted alkaline phosphatase, or the Green Fluorescent Protein (GFP) gene (see, e.g., Ui-Tei et al., FEBS Lett. 479:79-82 (2000)). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Once a functional promoter is identified, cis- and trans-acting elements may be located. Cis-acting sequences may generally be identified based on homology to previously characterized transcriptional motifs. Point mutations may then be generated within the identified sequences to evaluate the regulatory role of such sequences. Such mutations may be generated using site-specific mutagenesis techniques or a PCR-based strategy. The altered promoter is then cloned into a reporter gene expression vector, as described above, and the effect of the mutation on reporter gene expression is evaluated.

Antibodies

One aspect of the present invention concerns antibodies, single-chain antigen binding molecules, or other proteins that specifically bind to one or more of the polypeptides of the present invention and their homologues, fusions or fragments. Such antibodies may be used to quantitatively or qualitatively detect the polypeptides of the present invention. In general, an antibody or peptide is said to specifically bind to a protein or peptide molecule of the present invention if such binding is not competitively inhibited by the presence of non-related molecules.

Polynucleotides that encode all or part of the polypeptide of the present invention can be expressed, via recombinant means, to yield protein or peptides that can in turn be used to elicit antibodies that are capable of binding the expressed protein or peptide. Such antibodies may be used, for example, in immunoassays for that protein. Such protein-encoding molecules, or their fragments may be a fusion molecule (i.e., a part of a larger nucleic acid molecule) such that, upon expression, a fusion protein is produced. It is understood that any of the nucleic acid molecules of the present invention may be expressed, via recombinant means, to yield proteins or peptides encoded by these nucleic acid molecules.

The antibodies that specifically bind polypeptides and fragments thereof may be polyclonal or monoclonal and may comprise intact immunoglobulins, or antigen binding portions of immunoglobulins fragments (such as (F(ab'), F(ab').sub.2), or single-chain immunoglobulins producible, for example, via recombinant means. It is understood that practitioners are familiar with the standard resource materials which describe specific conditions and procedures for the construction, manipulation and isolation of antibodies (see, for example, Harlow and Lane, In: Antibodies: A Laboratory Manual, Cold Spring Harbor Press, Cold Spring Harbor, N.Y. (1988), the entirety of which is herein incorporated by reference).

As discussed elsewhere herein, such antibody molecules or their fragments may be used for diagnostic purposes. Where the antibodies are intended for diagnostic purposes, it may be desirable to derivatize them, for example with a ligand group (such as biotin) or a detectable marker group (such as a fluorescent group, a radioisotope or an enzyme). The ability to produce antibodies that bind the protein or peptide molecules of the present invention permits the identification of mimetic compounds of those molecules. Generally, mimetic compounds are compounds that is not the particular compound of interest, or a fragment of that compound, but which nonetheless exhibits an ability to specifically bind to antibodies directed against that compound. In one embodiment, the antibody is a rabbit polyclonal antibody.

Kits

Other aspects of the invention are directed to kits useful in carrying out the processes described herein. In general, the kits for practice of the methods of the invention preferably have somewhat different forms depending on their intended functions The kits will typically be packaged and include vessels containing reagents, the solution volumes of which will vary based on the amount of preparations for which the kit is rated. The vessels will generally include one or more reagents useful in carrying out the processes described herein. In certain embodiments, the kit is a compartmentalized kit; that is, the kit includes reagents contained in the same or separate vessels. Examples of vessels include, but are not limited to, small glass containers, plastic containers, or strips of plastic or paper. These and other similar vessels allow the efficient transfer of reagents from one compartment to another, or to some other vessel, such that the various samples and reagents are not cross-contaminated and the agents or solutions of each container can be added in a quantitative fashion from one compartment to another. Such containers can include a container which will accept the test sample, a container which contains the polypeptide or polynucleotide of the disclosure, a container which contains host cells or other materials for producing the polypeptides described herein (e.g., a vector, virus, or bacteriophage), containers which contain chromatography materials (such as one or more of the ion exchange, affinity, and hydrophobic interaction chromatography resins described above), containers which contain wash reagents (such as phosphate buffered saline, Tris-buffers, and the like), and/or containers which contain reagents useful in the detection of polysaccharides such as colanic acid (such as those described in the assays detailed below in Example 16). The kit can include sources and concentrations of the CAE polypeptides described herein. For larger scale applications, the kits will generally include similar reagents and solutions, but in larger quantity.

For instance, the kit may include a suitable bacterial expression vector for cloning the CAE polynucleotides described herein. Alternatively, the kit may include the polynucleotides and/or polypeptides themselves. The kit may also include cells, such as competent cells, for transforming recombinant clones into expression vectors. The kit may also include media (such as broth) for bacterial expression of the polypeptides of the invention. The kits may also include a set of three common alkaline lysis buffers as described in the Qiagen product manual and in Sambrook et al. as Solutions I, II, and III (i.e., 25 mM Tris HCl with 10 mM EDTA at pH 8.0, 1% SDS and 0.2 N NaOH, and 3 M potassium acetate at pH 5.5 respectively) and/or a resuspension solution (e.g., 10 mM Tris HCl at pH 8.0).

In some embodiments, for example, centrifuge-based spin filters or disc filters can be included. One model spin filter that works for this application is a Millipore Durapore centrifuge filter (Millipore Corporation, Billerica, Mass.). In addition, or by way of an alternative, filters can be included that have a packed steel wool, cellulose or polymer/plastic material in a centrifuge or other filter mechanism (e.g., a disc). Ceramic filters can also be included. Filter aids, such as a diatomaceous earth or similar compound, may also be included. For larger scale applications, a tangential-flow filter can be provided.

In one particular embodiment, the kit includes one or more of the polypeptides described herein. For example, the polypeptide included in the kit may be a purified polypeptide comprising an amino acid sequence having at least 90%, 98%, 99%, or 100% homology to SEQ ID NO: 1, and conservative amino acid substitutions thereof. In a particular embodiment, the polypeptide may have the amino acid sequence of SEQ ID NO: 1. Additionally or alternatively, the polypeptide included in the kit may be a purified polypeptide comprising an amino acid sequence having at least 90%, 98%, 99%, or 100% homology to SEQ ID NO: 2, and conservative amino acid substitutions thereof. In a particular embodiment, the polypeptide may have the amino acid sequence of SEQ ID NO: 2. The polypeptide included in the kit may also include a tag for isolation or purification (e.g., a His-tag or a FLAG®-tag); thus, the polypeptide included in the kit correspond to SEQ ID NO: 3, SEQ ID NO: 4, SEQ ID NO: 5, or SEQ ID NO: 6. Alternatively, the kit may include reagents and compositions that may be used to form such tagged polypeptides, along with the polypeptides of SEQ ID NO: 1 or SEQ ID NO: 2, and variants thereof.

The kits will also typically include instructions for use. The instructions will generally be suitable to enable an end user to carry out the desired preparation or assay. The instructions will generally be in a tangible expression, e.g., describing the reagent concentration for at least one preparation or assay, parameters such as the relative amount of reagent and sample to be admixed, maintenance or incubation time periods for reagent/sample admixtures, temperature requirements or preferences, and the like. The instructions may be printed on the outer or inner packaging of the kit, in a brochure, card, or other paper within the kit, and/or on the outer surface of the containers or vessels included in the kit.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLES

Colanic acid is present at significant levels in all plasmid DNA preparations, including clinical grade (cGMP) preparations. Colanic Acid comprises about 25% of the bacterial cell wall of gram negative bacteria. Colanic acid must be removed in order to provide the greatest safety, especially when mixed with cationic carriers for delivery in animals and in humans. Removal of colanic acid also increases gene expression from each plasmid because colanic acid is an inhibitor of RNA polymerase activity. A range of 2.2 to 4.4-fold increased reporter gene expression (CAT, chloramphenicol acetyltransferase) in the organs of Balb/c mice post-intravenous (iv) injection of BIV DNA-liposome complexes has been observed. Because colanic acid is often extremely large and branched-chain, it typically must be degraded in order to be effectively removed.

With the identification of colanic acid as a primary contaminating component of plasmid DNA polysaccharides, experiments were performed to develop methods for removing colanic acid from plasmid DNA. A specific enzyme, referred to hereafter as colanic acid degrading enzyme (CAE), had been reported to be produced by specific lytic bacteriophages (Hughes, K. A. et al. 1998. *J. Appl. Microbiol.* 85:583-590). The colanic acid degrading enzyme (CAE) had only been partially purified by researchers. Therefore, in order to develop a method for removal of colanic acid using a CAE, the enzyme must be purified, sequenced and expressed.

A bacteriophage (NST1) was identified that has the ability to lyse the *E. coli* strain SC12078, a strain that overproduces colanic acid. The NST1 bacteriophage was isolated and used as a source to isolate a purified CAE. It has been shown that polysaccharide viscosity decreases after incubation with a specific polysaccharide degrading enzyme (Sutherland, I. W. 1967. *Biochem. J.* 104:278-285). Thus, the protein samples containing CAE were identified by their ability to affect viscosity of samples containing colanic acid. It was found that the purified CAE isolated from NST1 had high levels of CAE activity as demonstrated by its ability to decrease the viscosity of colanic acid.

Once the purified CAE was isolated, as identified by bioassay of the ability to decrease sample viscosity, it was subjected to mass spectrometry and Edman degradation. Using Edman degradation, 15 amino acids were identified. By mass spectrometry, 8 additional protein fragments were sequenced, with each fragment containing between 6 to 16 amino acids. Screening of publicly available protein databases, including bacteriophage databases, did not reveal a single match with any of the peptide fragments.

A set of degenerate oligonucleotides was prepared based on the peptide sequences. These oligonucleotides were used to sequence the Colanic Acid Degrading Enzyme from the genomic DNA purified from the NST1 bacteriophage. The open reading frame (ORF) of the CAE was determined. The nucleotide CAE ORF was sequenced and the amino acid sequence of CAE determined using the universal genetic code. These sequences are shown in FIG. 1. PCR primers made to the beginning and end of the CAE ORF were used to amplify the ORF sequences from the NST1 bacteriophage genomic DNA by PCR for subsequent cloning into a yeast expression vector.

A naturally occurring colanic acid degrading enzyme (CAE) has been produced from bacteriophage that is a newly identified protein; generally, only small amounts are produced, approximately 110 μg from a 4.5 L phage+bacterial growth. A rabbit polyclonal antibody to this protein has also been produced that is a peptide generated antibody. This antibody is highly active and can be used for any purpose including Western blotting, ELISA assay, etc.

In order to produce large-scale amounts of CAE, a recombinant form of CAE was created for use in further purifying plasmid DNA preparations. Prior attempts to produce full-length recombinant CAE in yeast, baculovirus, and bacteria were generally unsuccessful, believed to be due to improper protein folding. After examining the predicted structure of the CAE and chymotrypsin digestion of the natural protein, we determined that 107 amino acids could be removed from the amino terminus (N-terminus) of the CAE protein without loss of activity. Chymotrypsin was the only protease that cleaved the natural full-length protein at this one location, amino acids 106-107. The recombinant CAE protein is not cleaved by any protease and is extremely stable (>2 years). We produced the functional truncated form of CAE in bacteria using the expression vector pET28a (Invitrogen; see Example 9). The truncated protein is produced in *Escherichia coli*, BL21 (DE3) grown at 16° C. overnight and then purified. About 10 mg of CAE recombinant protein from 1 L of growth can be produced.

Any plasmid DNA preparation can then be digested with recombinant CAE and further purified. Briefly, plasmid DNA is digested with CAE for 3 hours at 37° C. and then at 50° C. for 21 hours. Protein is removed, and the DNA is first purified by boronic acid chromatography. The plasmid DNA flows through and does not bind the column. Most polysaccharides except for extremely small fragments bind to the column. To remove the smallest, digested polysaccharides, the DNA suspension is finally purified by a Macrosep 100 Centrifugal Concentrator unit in the presence of zwittergent. The zwittergent is generally preferred because colanic acid appears to bind tightly to the plasmid DNA.

For use in the preparation of clinical grade plasmid DNA and to reduce cost, recombinant CAE can also be placed on a solid support that can be regenerated and reused multiple times.

By the assays described herein, we find no detectable levels of polysaccharides including colanic acid.

Example 1

Preparation of Colanic Acid

Colanic acid was prepared using SC12078 bacteria, a bacterial strain that is known to overproduce colanic acid. A few colonies of SC12078 bacteria were picked from a plate and inoculated into 2 liters of LB broth with 0.4% glycerol containing chloramphenicol (10 ug/ml). The bacteria were allowed to grow at 37° C. in a shaker incubator at 230 rpm overnight. The growth was stopped when the cultures reached an optical density (OD) 600 between about 4.5 to about 4.7.

Prior to removing the bacteria by centrifugation, the flasks of bacteria were briefly shaken to increase the amount of colanic acid released into the culture medium. The bacteria were pelleted by centrifugation at 6,000×g for 15 min at 4° C.

The bacterial pellet was discarded and the supernatant saved and concentrated using an Amicon filter apparatus with a YM30 membrane.

The colanic acid was precipitated from the concentrated supernatant by adding 3 volumes of ice cold ethanol to one volume of supernatant and letting the mixture sit on ice for 15 min. The precipitate was collected by centrifuging the mixture at 10,000×g for at least 15 min at 0° C., or until the supernatant is clear. The precipitate was dissolved in a minimal amount of sterile water and dialyzed overnight against at least three changes of water.

The dialyzed solution was lyophilized to dryness, being sure to weigh the tube that the solution was to be dried in before adding the solution in order to determine the weight of the sample after freeze drying. Once the sample was totally dried, water was added to the sample to make a 2% solution of the lyophilized sample.

Solid ammonium sulfate was added to the 2% solution of the lyophilized sample to achieve a 90% ammonium sulfate saturated solution. The 90% ammonium sulfate saturated solution precipitated the O antigen and the colanic acid. The precipitated polysaccharides were collected by centrifugation at 10,000×g for at least 15 min at 0° C., or until the supernatant was clear. The pelleted precipitate was dissolved in a minimal amount of water, dialyzed overnight against at least three changes of water, and lyophilized to dryness.

The lyophilate was dissolved in 150 ml of 0.1 M sodium phosphate pH 7.2. The colanic acid was precipitated from the lyophilate solution by adding 37.5 ml of hexa-decyl-trimethyl-ammonium bromide (also called cetavlon or cetrimide). The colanic acid precipitate was collected by centrifugation at 10,000×g for at least 15 min at 0° C., or until the supernatant was clear.

The pelleted precipitate was dissolved in 100 ml of 1M NaCl. The colanic acid is reprecipitated by adding 3 volumes of ice cold ethanol to the 1M NaCl solution and letting the mixture sit on ice for 15 min. The colanic acid precipitate was collected by centrifuging the mixture at 10,000×g for at least 15 min at 0° C., or until the supernatant was clear. The colanic acid precipitate was dissolved in a minimal amount of sterile water and dialyzed in a cold room overnight against at least three changes of water.

The dialyzed solution was lyophilized to dryness, being sure to weigh the tube that the solution was to be dried in before adding the solution in order to determine the weight of the sample after freeze drying. Once the sample was totally dried, the colanic acid was dissolved in a minimal amount of water, aliquoted into sterile tubes, and stored at −25° C.

Example 2

NST1 Phage Production

The NST1 bacteriophage was identified as a good source of CAE by its ability to lyse $E.\ coli$ strain SC12078, a strain that overproduces colanic acid. The NST1 bacteriophage was isolated and used as a source to isolate a purified CAE.

A few colonies of SC12078 bacteria were taken from agar plates and inoculated into two tubes containing 5 ml of LB-glycerol media containing 0.4% chloramphenicol (10 ug/ml). The bacteria were allowed to grow at 37° C. overnight to prepare a phage stock that is. Serial dilutions ($1:10^2$, $1:10^1$, $1:10^0$, $1:10^{-1}$, and $1:10^{-2}$) are prepared of the phage stock containing five different NST1 phage particle numbers. The dilutions are based on 1 ul of phage stock stored at 4° C. containing $10^7$ phage particles). The overnight growth (200 ul) is mixed with 1 ul of phage stock to make the $10^7$ concentration of phage. Additional dilutions are made containing 180 ul of overnight bacterial growth mixed with 20 ul of the next higher concentration of phage. The highest concentrations containing $10^7$ through $10^3$ particles are discarded.

The lower 5 dilutions were plated by quickly mixing each into 3 ml of LB+glycerol top agar (agarose at 0.7%, kept at 55° C.). The mixture was quickly poured onto LB+Chloramphenicol (10 ug/ml) plates. The mixing and pouring is preferably done quickly to avoid solidification of the top agar. The plates were then incubated upside down at 37° C. for 5 hours. After incubation, plates were wrapped with parafilm and stored at 4° C. Plates that do not contain plaques are discarded.

Example 3

Large Scale Production of NST1 Phage Supernatant

The bacterial strain SC12078 (a strain overproducing colanic acid) was maintained on LB-containing chloramphenicol (10 ug/ml) agar plates and stored at 4° C. Several plates of NST1 phage, as described in Example 2, were maintained on LB-glycerol top agar (agarose 0.7%), layered on top of LB-chloramphenicol (10 mg/ml) agar plates stored at 4° C. The plates were not stored for more than one month as NST1 loses viability and its ability to infect bacteria with longer storage time periods.

A few colonies of the SC12078 bacteria were inoculated into four 50 ml sterile tubes, each tube containing 15 ml of LB-glycerol-chloramphenicol (10 ug/ml) media. The colonies were allowed to grow overnight at 37° C. in a shaker incubator.

Three 4 liter flasks were then inoculated with 15 ml of the overnight culture, each flasks containing 1.5 liters of LB-glycerol-chloramphenicol (10 ug/ml) media. The bacterial colonies were allowed to grow at 37° C. in a shaker incubator (230 rpm) for about 2-4 hours until the solution had an OD600 between 0.12 and 0.67.

Each flask was then inoculated with 30 NST1 phage plugs and the flask incubated overnight at 37° C. with shaking (230 rpm). The OD600 of the SC12078 cultures inoculated with the NST1 phage that were incubated overnight was measured and was typically between 4.5 and 4.7. These cultures were centrifuged at 4200 rpm at 4° C. for 5 min using large, autoclaved centrifuge bottles. The supernatant, containing the NST1 phage, was poured into sterile containers and stored at −80° C., or immediately purified. The pellets containing the bacterial cells and debris were discarded.

Example 4

Isolation of the Colanic Acid Degrading Enzyme

Phage supernatant was prepared as described in Example 3. Phenyl methyl sulfonyl fluoride (PMSF) was added to the phage supernatant to a final concentration of 0.1 mM PMSF to prepare the starting solution and then stored at 4° C.

The starting solution for CAE purification was centrifuged in the table-top centrifuged at about 4200 rpm for 20 min at 4° C. The resulting supernatant was removed and saved and the pellet discarded. Using an Amicon filter apparatus and a YM30 membrane, the supernatant volume was reduced from 4 liters to a 4 ml sample. The 4 ml sample was further centrifuged in a polycarbonate centrifuge tube at 40,000×g in an SS34 rotor for 60 minutes at 4° C. The sample was dialyzed overnight in the cold room against at least 3 changes of 10 mM Tris HCl, pH 7.5, containing 0.1 mM PMSF.

A Q Sepharose Fast Flow column (10 cm high, 1.5 cm diameter) was equilibrated with 10 mM Tris HCl, pH 7.5, 0.1 mM PMSF until the pH of the fluid eluting from the column was 7.5. The dialyzed supernatant was loaded onto the equilibrated column and the column washed with 2 column volumes (about 30 ml) of 10 mM Tris HCl, pH 7.5, 0.1 mM PMSF.

The column was eluted using a linear gradient from 10 mM Tris HCl, pH 7.5, 0.1 mM PMSF (150 ml) to 200 mM Tris HCl, pH 6.5, 0.1 mM PMSF (150 ml) collecting 4 ml fractions (75 fractions total) at a flow rate of 7 ml per hour. The fractions collected were tested for colanic acid degrading activity using a viscometer test, described below in Example 5, and those fractions containing CAE activity were pooled.

The pooled CAE active fractions were then concentrated on a disposable Amicon filter by centrifugation. The protein concentration of the resulting concentrate was determined and a sample of the concentrate was electrophoresed on a gradient polyacrylamide gel (4-12%). The electrophoresed sample contained five protein bands.

The protein concentrate was then separated by size on a 120 cm column containing Toyopearl HW-50F resin equilibrated with phosphate buffered saline (PBS), pH 7.3-7.4, containing 0.1 mM PMSF. The column eluate was collected in 1 ml fractions. Each fraction was tested for CAE activity and the active fractions were pooled.

The pooled fractions were concentrated on a disposable Amicon filter by centrifugation. The protein concentration of the concentrate was determined and a sample of the concentrate was electrophoresed on a gradient polyacrylamide gel (4-12%). A single protein band was obtained that had a molecular weight of about 84,000 Daltons.

The protein band was prepared by standard procedures and submitted for mass spectrometric analysis and Edman degradation.

Example 5

Identification of the Partial Amino Acid Sequence of CAE Isolated from Bacteriophage NST1

The CAE protein was purified as described previously. The purified CAE protein was subjected to mass spectrometry using the Applied Biosystems Procise Sequencer PROCISE-cLC for 17 cycles and Edman degradation. Using Edman degradation, 15 amino acids of the N-terminus were identified as set forth below:

ANSYNAYVANGSQTA (SEQ ID NO: 9)

By mass spectrometry, 8 additional protein fragments were sequenced, with each fragment containing between 6 to 16 amino acids as set out below:

LLEQGTGEALTDGVLR (SEQ ID NO: 10)
VPNSEVSLNALPNVQR (SEQ ID NO: 11)
LADYEFTSAPSNSK (SEQ ID NO: 12)
YSDLSTLN (SEQ ID NO: 13)
QLLFDTAPLA (SEQ ID: 14)
APYQVDDNL (SEQ ID NO: 15)
FGAYLPDD (SEQ ID NO: 16)
LGTLGG (SEQ ID NO: 17)

In each of these peptide fragment sequences the amino acid leucine (L) may actually be either leucine (L) or isoleucine (I), the amino acid aspartic acid (D) may actually be aspartic acid (D) or asparagine (N), the amino acid glutamine (Q) may actually be glutamine (Q) or lysine (K), and the amino acid phenylalanine (F) may actually be phenylalanine (F) or oxidized methionine.

Example 6

Cloning the Colanic Acid Degrading Enzyme

A. Preparation of Degenerate Oligonucleotide Primers

Degenerate oligonucleotide primers are prepared using degenerate codons of the amino acid sequences from the protein fragments of the CAE protein described above.

B. Preparation of Bacteriophage Genomic DNA

The genomic DNA of the Bacteriophage NST1 was purified using standard DNA purification methods. The degenerate oligonucleotide primers were used to hybridize with the bacteriophage genomic DNA to identify the CAE gene as described below.

C. Sequencing and Amplification of CAE Gene from Genomic DNA

Sequencing of the CAE ORF was performed directly on the NST1 bacteriophage genomic DNA starting with the degenerate primers and then using primers based on known sequences for subsequent rounds of sequencing. The CAE ORF was fully sequenced on both strands of the NST1 bacteriophage genomic DNA.

Primers made to the beginning and end of the CAE ORF sequences were made and then used to amplify the sequences of the CAE gene from the NST1 bacteriophage genomic DNA using the Polymerase Chain Reaction (PCR) using the Deep Vent DNA Polymerase (New England BioLabs) to avoid errors during amplification. The amplified DNA was then electrophoresed and the appropriate band was excised and purified from the gel.

Example 7

Sequence of the Colanic Acid Degrading Enzyme

The nucleotide sequence of the CAE was determined as set out in FIG. 9:

```
ATGGCGAACA GCTATAATGC TTACGTGGCG AACGGTTCAC AGACCGCATT CCTCGTCACG    60   (SEQ ID NO: 7)

TTCGAGCAGC GCGTGTTCAC TGAGATTCAG GTGTACCTCA ACTCCGAACT CCAGACGGAA   120

GGGTACACCT ACAACTCTGT GACCAAACAG ATTATCTTCG ACACCGCCCC GCTCGCCGGG   180

GTGATTGTCC GACTCCAACG CTACACCTCT GAGGTTCTGC TGAACAAGTT TGGCCAAGAC   240

GCTGCCTTCA CCGGGCAGAA CCTTGACGAG AACTTTGAGC AGATTCTGTT CAAGGCTGAG   300

GAAACTCAGG AAGCATGGCT CGCGCCACTT GACCGCGCCG TCCGTGTTCC GAACTCCGAA   360

GTCTCCATCA ACGCATTACC GAACGTCGCT GGCCGCCGCA ACAAGGCACT GGGCTTTGAC   420

AGCAATGGTC AGCCGTTCAT GATTCCTCTG GTCGATATCC CGGACTCCGC GCTGGCGATT   480
```

```
GCTCTGGCAA TGGCTGACGG CGGTAAGTGG ATTGGTACTC TCGGCGGGGG CACGTTCCTC   540

GACCGTCAGG ATACCGTCTG CCTGTCCGAG TTCACCAACA ACACTGGGTA CGCCTCTGTC   600

GCCGCTGCGG TGCAGGCTTG CTTCGACTAT GCGAAAGCCA ACGGCAAGGT CGTTGACGCT   660

CGCGGCTGGG AAGGTACGGT GGATTCCACT GTGCTGATGG ACGGTATTGA GGTCGTCGGC   720

GGTACGTGGC ACGGCAAGGC TGACATTCGC CTGCTGAACT CCACCTTCCG CAACTTCGTG   780

GCCTCTACTG TCCGTGTCGC CTACTGGGGC GGCGAGGTGC GTATTGCTGA CTATGAGTTC   840

ACCAGCGCAC CGAGCAACTC CAAGGTTACG TCTATCCTGT TCCAAGGCAA CATCGCCGGG   900

GGCAGCTACG TCATTGAGAA CGGTATCCAC CGCAATGGTA AGTTCGGTAT TCTCCAACAG   960

GGTACTGGCG AGGCTATCAC CAACGGCGTT ATCCGTGGCA TCACCATGAT GGATATGCAG  1020

GGTGACGGTA TCGAGATGAA CGTAATCAAC AAGCACTATG ATGGTGGCCT GCTGATTGAG  1080

AACATCTTCC TTGAGAACAT CGACGGCACC AACGCGCCTA TCCCACTGTC CAACTGGGGC  1140

ATTGGTATCG GTATCGCTGG TCAAGGCCCG TTCGGTTGGG ATGCTGCTGA GACGCAGTAT  1200

GCGAAGAACG TCACTGTCCG TAACGTCCAT GCTCCGCGTG GTGTGCGTCA GGTCGTCCAC  1260

TTCGAGGTTA CGCGTGACAG CACCTGCGAG AACGTAGTGG CCAACCCTGA CCTGTCCGTC  1320

TCCATTGGTA CTGGCCTGAC TGCCGCTGGT GTAATCACGT ACGGCTGCAA GCGCATGACC  1380

ATTGACGGTG TAGTCGGTGA GCCTATGAAC ACCGGAGCAA CCTCTCCGAA CGATATTCGT  1440

ATCGTGATGT TGGAGTGGGG TGCGAACCAA GCAGGTGCTG GCGGTACGCC GGGTGCAGCT  1500

TGCCCATCGT TCGACATGAC CGTGCGTAAC GTGCAGACCC GTACCGGGCG CTTCTATGCT  1560

GGTGTCGGCT CCGACGATGA CAACACCAAC ACATATCACC TTGAAAACAT TCACTGTTAC  1620

AAGATGACGC TGTTTGGTGT GGCAACTCTG CTGAACATGA CCAACGTGAC TGGTGTGGTG  1680

TTCGACGCTG TAGGCGATGA CTCCAGCGGC GGTACGTCCT CCAACGGTCT GTACCCGCGT  1740

AAGAAGACTG TTCTCAACAT GGTGAACGTG AACTTCTACG GCCGGGCAT GACCGAGGGT  1800

GCGCTGTACA GTAAGGCTCG CTACTCGGAT ATCAGCACGC TGAACTCCAA CGTGCGTGCT  1860

ATCCCGTACA CCAACATCCA AGGTAACGTG GGTGTCATCC TGTCTCCGGT CAACCGCATG  1920

TACACGCTGC CGAACGCCCT CGCTACCCTT GACGGTAATG AGTTCCCCAC CGGGAAAGAG  1980

TTCTGCGAAG GTACTGTGCT GTTCAAGACC GATGGCTCCG GTGGCAACTT CATCGTGACC  2040

CGGTTCGGTG CGTACATCCC GGATGACGGT AACAACTTCA AGGTGCGTGC TGCTGCCGCT  2100

GGCCAGACGT ATCTGGAGCA GAACCTGACT CCGGCTGGTA CTCAGGCTTC CACCTCGTGG  2160

CTGTACCATA AGCCAATCTC TGCTGGTACT CGACTCAATG TTCCGGGTGC CGGGCCGAGC  2220

GGCGGTACGC TCACTGTGAC GGTGGTGCGT GCTCCGTATC AGGTGGACAA CAACATCGGA  2280

AACCCGGTAC GCATCGACAT TACCCCGGCC ATTGTGACGG CAATCCCTGC GGGAACGCAG  2340

CTCGCCGCTA CCTACCCGGT GGCTTACATC TAA
```

The amino acid sequence was determined using the universal genetic code and is shown in alignment with the nucleotide sequence in FIG. 1. The amino terminus of the CAE matched the Edman degradation results, except the Edman degradation did not detect the terminal methionine. In addition, the molecular weight for the CAE was determined to be 84,354 and corresponded to the molecular weight of the protein band sequenced as determined by its position on polyacrylamide gels.

Example 8

Using Colanic Acid Degrading Enzyme in the Purification of Plasmid DNA

A plasmid DNA sample is tested for the presence of colanic acid. If colanic acid is present in the plasmid DNA sample then the sample of plasmid DNA is incubated with the recombinant colanic acid degrading enzyme of the present invention. The CAE will digest the colanic acid into a number of smaller polysaccharides that can be separated from the plasmid DNA by a variety of methods known in the art. The plasmid DNA sample will then be separated from the CAE and further purified as described herein.

Example 9

Construction of Recombinant CAE, Amino Acids 107-790 (Underlined) Including 6 Histidines at the N-Terminus, in Vector Pet-28A-C(+)

Amino Acids Contained in the Construct: [(Nco1) MGH-HHHHH . . . stop (Xho1)]

(SEQ ID NO: 4)
MGHHHHHH<u>LAPLDRAVRVPNSEVSINALPNVAGRRNKALGFDSNGQPFMI</u>

<u>PLVDIPDSALAIALAMADGGKWIGTLGGGTFLDRQDTVCLSEFTNNTGYA</u>

<u>SVAAAVQACFDYAKANGKVVDARGWEGTVDSTVLMDGIEVVGGTWHGKAD</u>

<u>IRLLNSTFRNFVASTVRVAYWGGEVRIADYEFTSAPSNSKVTSILFQGNI</u>

<u>AGGSYVIENGIHRNGKFGILQQGTGEAITNGVIRGITMMDMQGDGIEMNV</u>

<u>INKHYDGGLLIENIFLENIDGTNAPIPLSNWGIGIGIAGQGPFGWDAAET</u>

<u>QYAKNVTVRNVHAPRGVRQVVHFEVTRDSTCENVVANPDLSVSIGTGLTA</u>

<u>AGVITYGCKRMTIDGVVGEPMNTGATSPNDIRIVMLEWGANQAGAGGTPG</u>

<u>AACPSFDMTVRNVQTRTGRFYAGVGSDDDNTNTYHLENIHCYKMTLFGVA</u>

<u>TLLNMTNVTGVVFDAVGDDSSGGTSSNGLYPRKKTVLNMVNVNFYGPGMT</u>

<u>EGALYSKARYSDISTLNSNVRAIPYTNIQGNVGVILSPVNRMYTLPNALA</u>

<u>TLDGNEFPTGKEFCEGTVLFKTDGSGGNFIVTRFGAYIPDDGNNFKVRAA</u>

<u>AAGQTYLEQNLTPAGTQASTSWLYHKPISAGTRLNVPGAGPSGGTLTVTV</u>

<u>VRAPYQVDNNIGNPVRIDITPAIVTAIPAGTQLAATYPVAYI</u> stop.

The PCR amplified region of CAE from amino acids 107 to 790, including 8 additional amino acids at the N-terminus, was digested with restriction enzymes Nco1 and Xho1, and ligated into the multiple cloning site of vector pET-28a-c (+) that was also digested with Nco1 and Xho1. This construct was transformed and grown in expression host BL21 (DE3) in Hyper Broth medium containing 50 mg/liter kanamycin. The large-scale culture was grown at 37° C. with shaking at 225 rpm until $OD_{600}$ reached 0.5 (about 2 to 4 hours). The temperature was changed to 16° C., and growth was continued for 30 min. Then IPTG was added to a final concentration of 0.015 mM, and growth continued for an additional 20 hours. The recombinant CAE is then purified on a Ni-NTA column that selectively binds the 6 histidines at the N-terminus. The bound protein is then eluted, concentrated, reconstituted in storage buffer, and stored in the refrigerator at 4° C.

Example 10

Transform Recombinant CAE Clone into Expression Host BL21 (DE3)

Thaw on ice one vial of One Shot® BL21 (DE3) cells. Add 10 ng of plasmid DNA, in a volume of 1 to 5 µl, to the cells and mix by tapping gently. Do not mix cells by pipetting. Incubate the vial on ice for 30 minutes. Incubate for exactly 30 seconds in the 42° C. water bath. Do not mix or shake. Remove vial from the 42° C. bath and quickly place on ice. Add 250 µl of pre-warmed SOC medium to the vial. Place the vial in a microcentrifuge rack and secure the vials in the rack with tape. Place the rack on its side in a shaking incubator, and shake the vial at 37° C. for exactly 1 hour at 225 rpm. Plate 20 to 200 µl each of the transformation reaction onto two LB plates containing 80 µg/ml Kanamycin. Plate two different volumes to ensure well-spaced colonies on at least one plate. The remaining transformation reaction may be stored at +4° C. and plated out the next day, if needed. Invert the plates and incubate at 37° C. overnight.

Example 11

Growing Bacteria Expressing Recombinant CAE

Inoculate a single colony or 30 µl from a glycerol stock into 30 ml LB medium containing 50 mg/liter kanamycin. Incubate at 37° C. with shaking at 225 rpm overnight. Add 24 ml overnight culture to 2 liters of Hyper Broth medium containing 50 mg/liter kanamycin. Grow the culture at 37° C. with shaking at 225 rpm until $OD_{600}$ reaches 0.5 (2-4 hours). Change temperature to 16° C., continue shaking for 30 min. Add IPTG to the final concentration Of 0.015 mM, continue growing for 20 hours. Harvest cell by centrifugation at 4800×g for 15 min and store the pellet at −80° C.

Example 12

Purification of Recombinant CAE

Make solutions. Add PMSF just before use.
A. 20 mM Tris-HCl pH 8.0, 0.25M NaCl, 10% Glycerol, 10 mM Imidazole, 0.1 ml/liter β-mercaptoethanol, 1 mM PMSF.
B. 20 mM Tris-HCl pH 8.0, 0.25M NaCl, 10% Glycerol, 125 mM Imidazole, 0.1 ml/liter β-mercaptoethanol, 0.1 mM PMSF.
C. 20 mM Tris-HCl pH 8.0, 0.25M NaCl, 10% Glycerol, 500 mM Imidazole, 0.1 ml/liter β-mercaptoethanol, 0.1 mM PMSF.
D. 20 mM Tris-HCl pH 8.0, 0.25M NaCl, 10% Glycerol, 0.1 mM PMSF.

Equilibrate Ni-NTA column (20 ml bed volume, for 2 liter culture) with 200 ml of buffer A. Thaw and suspend the cell pellet (from 2 liter culture) in 150 ml of buffer A. Break cell pastes using MICROFLUIDIZER PROCESSOR (Model M-110Y) (according to manufacture's instructions) and centrifuge at 40,000×g to obtain clear supernatant. Load supernatant to Ni-NTA column and wash with 600 ml of Buffer A, then wash with 80 ml of Buffer B. Elute bound recombinant CAE with 80 ml of Buffer C. Add elutant to Amicon Ultra-4 Centrifugal Filter unit with 30K cutoff. Spin at 2800×g at 4° C. to concentrate elutant. Reconstitute the retentate to the original sample volume with Buffer D. Repeat this process three times. Examine the total protein obtained.

Example 13

Digestion of Plasmid DNA with Recombinant CAE

Purify plasmid DNA from 2.5 liters LB culture using EndoFree Plasmid Giga Kit (according to manufacture's instructions). Dissolve plasmid DNA in 4 ml of 0.05 M potassium phosphate buffer, pH 6.5. Add a suitable amount of recombinant CAE (plasmid DNA: CAE=10:1), incubate at 37° C. for 3 hours. Change temperature to 50° C. and incubate for 21 hours.

Example 14

Boronate Affinity Chromatography

Boronate chromatography has been used to purify samples containing RNA, mononucleotides, oligonucleotides, thymine glycol-containing DNA, and benzo(a) pyrene: DNA adducts (Schott, H. et al. 1973. *Biochemistry* 12:932-938; Singh, N. and R. C. Wilson. 1999. *J. Chromatography* 840: 205-213; Jerkovic, B. et al. 1998. *Anal. Biochem.* 255:90-94; Pruess-Schwartz, D. et al. 1984. *Cancer Res.* 44:4104-4110). Boronate chromatography, however, has not been used in the past for successful purification of plasmid DNA because no one had identified the presence of substantial quantities of polysaccharides present in plasmid DNA and the toxic effects of these polysaccharides during gene therapy.

Commercially available boronic acid affinity resins bind compounds containing cis-diol groups. A preferred boronic acid affinity column can be acquired from Pierce, Rockford, Il. This boronic acid column has a coupled m-aminophenyl-boronic acid to polyacrylamide spherical beads at 100 mmoles of boronate/ml of gel.

The boronic acid column was equilibrated in 0.2 M ammonium acetate, pH 8.8. The plasmid DNA samples were precipitated in ethanol and the precipitate washed with 70% ethanol. The washed pellet of DNA was dissolved in 0.2 M ammonium acetate, pH 8.8. The DNA solution was then loaded onto a boronic acid column at approximately 10 mg DNA per 2 ml of boronate column material. The column was then washed with 0.2 M ammonium acetate, pH 8.8. The column wash was collected in fractions and the optical density (O.D.) of each fraction at 260 nm was measured. The fractions having the highest O.D. 260 nm were pooled and loaded onto a second boronic acid column. The second column was washed with 0.2 M ammonium acetate, pH 8.8. Fractions from the column wash were collected and each of their O.D. 260 nm measured. The fractions having the highest O.D. 260 nm were pooled and the DNA precipitated with ethanol. The precipitate was washed with 70% ethanol and resuspended in 10 mM Tris buffer, pH 8.0. The DNA sample was filter sterilized and stored at $-20°$ C. until it was used.

Plasmid DNA did not bind to the boronate column and flowed through the boronate column with the wash buffer. On the other hand, the polysaccharide contaminants, RNA, and LPS bound or adsorbed onto the boronate column. Eluting the polysaccharide fractions with 0.1 M formic acid regenerated the boronic acid columns. The boronic acid columns were then washed and stored in 0.1 M sodium chloride and 0.02% sodium azide.

The purified DNA sample was then subjected to the methods of detection and quantification for polysaccharides of the present invention. Each purified sample was subjected to one or more polysaccharide detection method (i.e., the uronic acid detection method, the fucose detection method, and/or the fluorescence labeling method). The results of the polysaccharide detection methods consistently demonstrated that the use of boronate chromatography produced DNA samples with polysaccharide contents that were reduced to undetectable levels. These data are provided below in Table 2.

Example 15

Macrosep Clean-Up

After Boronic Acid chromatography, pool the fractions having the highest OD260. Precipitate plasmid DNA with 2 volume of 100% cold ethanol, and ¹/₁₀ volume of 3M sodium acetate, pH 5.2. Incubate at $-20°$ C. (1 hour to O/N). Spin at 13000 rpm for 15 min at 4° C. Wash the pellet twice with 1 ml of 70% ethanol, spin at 13000 rpm for 5 min. Air dry and resuspend the pellet in 14 ml of 10 mM Tris-HCl, pH 8.0, containing 0.1% zwittergent. Incubate at 37° C. for 15 min. Add solution to Macrosep 100 Centrifugal Concentrator unit with 300K cutoff (according to manufacture's instructions). Spin at 3500 rpm for 1 hour at 30° C. to concentrate plasmid DNA. Reconstitute the retentate to the original sample volume with 10 mM Tris-HCl, pH 8.0, containing 0.1% zwittergent. Spin at 3500 rpm for 1 hour at 30° C. Repeat this process three times. Reconstitute the retentate to the original sample volume with 10 mM Tris-HCl, pH 8.0. Spin at 3500 rpm for 1 hour at 30° C. Repeat this process two times. Precipitate plasmid DNA with 2 volume of 100% cold ethanol, and ¹/₁₀ volume of 3M sodium acetate, pH 5.2. Incubate at $-20°$ C. (1 hour to O/N). Spin at 13000 rpm for 15 min at 4° C. Wash the pellet twice with 1 ml of 70% ethanol, spin at 13000 rpm for 5 min. Air dry and resuspend the plasmid DNA pellet in sterile water and adjust the final concentration to 5 mg/ml.

Example 16

Quantification of Polysaccharides in Plasmid DNA Samples

In order to assure that any method of purification of a plasmid DNA sample successfully removes virtually all of the contaminating polysaccharides, a means for assessing polysaccharide contamination of DNA before and after such purification process was developed.

Three assays were developed, one based on detection of uronic acid levels (where polysaccharides are known to contain high levels of uronic acid), one based on fucose levels (where fucose is known to make up 22% of colanic acid), and one based on the visual detection of fluorescent-labeled polysaccharides in gel-electrophoresed samples.

1. Uronic Acid Assay

*E. coli* expresses several major classes of polysaccharides, including O- and K-antigen associated polysaccharides, colanic acid, and enterobacterial common antigen (ECA). Colanic acid exists in both high and low molecular weight forms, whereas ECA is typically in a low molecular weight form. The O- and K-antigen associated polysaccharides have variants that are associated with Lipid A and other variants that are not associated with Lipid A. The Lipid A associated polysaccharides may be either covalently linked, or non-covalently linked. The Lipid A associated polysaccharides are characteristically low molecular weight variants. The O- and K-antigen associated polysaccharides that are not associated with Lipid A exist as high and low molecular weight variants.

Each of these *E. coli* capsular polysaccharides, particularly the long-chain and branched polysaccharides found in plasmid DNA preparations, contains uronic acid. For example, colanic acid is approximately 11 weight % uronic acid. Enterobacterial common antigen (ECA) consists of about 33 weight % uronic acid and the O- and K-antigen associated polysaccharides have about 25 weight % uronic acid.

The uronic acid content of a plasmid DNA sample was measured using standard curves generated with heparin sulfate and glucuronic acid as standards. Heparin sulfate resembles the polysaccharide contaminants from *E. coli*, because uronic acid comprises about 25% of the total weight of heparin sulfate. Heparin sulfate consists of 50% sugars by weight. Half of these sugars are glucosamine and the other half of the sugars are iduronic acid and glucuronic acid. The rest of the heparin sulfate is contributed by modifications of the sugars including sulfates and acetylamides. Alternatively, glucuronic acid can be used to create a standard curve for the direct measurement of uronic acid.

Standard curves are generated using 0.1 ml of heparin or glucuronic acid standards containing 0.0, 0.05, 0.1, 0.2, or 0.5 mg of the standard per milliliter of solution. The standard solution (0.1 ml) is placed is a glass test tube with 3 ml of a borate/sulfuric acid solution (i.e., 0.025 M sodium tetraborate 10-hydrate dissolved in sulfuric acid having a specific gravity of 1.84) and mixed well. A 0.1 ml of a 0.125% solution of carbazole in absolute ethanol is added to the mixture and the entire mixture is vortexed. The top of each test tube is covered and the tubes are immersed in boiling water for 10 min. The tubes are allowed to cool and the absorbance of the solution at 530 nm is read in a spectrophotometer. The absorbance values obtained for the standards are plotted against the concentration of the standards. The uronic acid content of plasmid DNA samples can be extrapolated from its absorbance value at 530 nm when the DNA sample has undergone the same reaction.

The polysaccharide content of the plasmid DNA sample can then be extrapolated by multiplying the amount of uronic acid by a number ranging from 3.3 to 9.1 (depending on the prevalence of colanic acid, ECA and the O- and K-antigens in the sample). The uronic acid content of plasmid DNA samples was calculated from standard curves generated with heparin and glucuronic acid standards. The results generated from the two standard curves were substantially equivalent.

This method was used to assess the uronic acid content of many plasmid DNA preparations; such DNA preparations included GMP grade DNA prepared by certain companies for use in human drug trials, as well as clinical grade DNA. "GMP" is a term used by the U.S. Food and Drug Administration to designate a compound as having been produced according to regulations known as the Good Manufacturing Practice (GMP) regulations. Compounds produced by GMP are considered to be safe for use in humans. The results of testing various plasmid DNA preparations are presented below in Table 2.

TABLE 2

| DNA Plasmid Preparation/Source | Amount of Uronic Acid Detected (mg/mg DNA) |
|---|---|
| Qiagen Endotoxin Free, Prep A | 0.12 |
| Qiagen Endotoxin Free, Prep B | 0.18 |
| GMP Grade DNA, Company 1 | 0.11 |
| Clinical Grade DNA, Company 1 | 0.11 |
| GMP Grade DNA, Company 2 | 0.11 |
| GMP Grade DNA, Company 3, Prep A | 0.20 |
| GMP Grade DNA, Company 3, Prep B | 0.22 |
| GMP Grade DNA, Company 4, Prep A | 0.22 |
| GMP Grade DNA, Company 4, Prep A | 0.25 |
| Plasmid DNA prepared according to present disclosure | 0.00 |

2. Fucose Assay

Since gram-negative bacteria are known to consist of approximately 25% colanic acid, plasmid DNA preparations were also subjected to an assay for colanic acid. The colanic acid assay was based on the amount of fucose present per mg of DNA. Colanic acid consists of 22% fucose in the ratio of 2:2:1:1:3 (fucose:galactose:glucose:uronic acid:other modifications), whereas the other polysaccharide contaminants do not contain fucose, or only small amounts of fucose. Thus, the fucose assay allowed for identification of the amount of colanic acid contamination in a purified plasmid DNA preparation.

For example, a plasmid DNA preparation containing about 0.7 mg polysaccharide per mg of DNA, as estimated by the uronic acid assay, had 0.14 mg of fucose per mg of DNA or about 0.64 mg of colanic acid. It was generally found that the primary polysaccharide contaminant in plasmid DNA preparations was colanic acid.

Since colanic acid was present in high levels in even clinical grade plasmid DNA, it is necessary to assure that any method of purification of a plasmid DNA sample successfully removes virtually all of the contaminating colanic acid. Thus, a method for assessing colanic acid contamination of DNA before and after such purification process was developed.

The basic procedures for assay of fucose content in samples can be found in a paper by Morris (Morris, J. B. 1982. *Anal. Biochem.* 121:129-134). Detailed descriptions of the solution preparation and storage conditions for solutions and samples for this assay have also been published (Passonneau, J. V. and O. H. Lowry. 1974. In: *Methods of Enzymatic Analysis*, U. H. Bergmeyer (ed.), 2nd edition, Academic Press: New York, volume 4, pp. 2059-2072).

DNA samples to be assayed (450 ug) are transferred to 3 ml vials and lyophilized. To each sample, 200 ul of 5.5 M trifluoroacetic acid is added and the reaction vials are sealed with a Teflon-lined cap. Hydrolysis is accomplished by heating the samples for 4 hours at 100° C. After cooling to room temperature, the trifluoroacetic acid is removed with a stream of argon gas under a fume hood. The remaining residue is then redissolved in 212 ul of sterile water. Only 200 ul of the resulting sample, which corresponds to 425 ug of the initial DNA sample, is used in the fucose assay.

Using the method described by Morris (1982. *Anal. Biochem.* 121:129-134), 200 ul of the samples and standards are pipetted into 1.5 ml micro centrifuge tubes. The standards used are fucose solutions ranging in concentration from 0 ug fucose to 200 ug fucose (0, 1, 12.5, 25, 50, 100 and 200 ug fucose).

The tubes are placed on ice and 50 ul of a 1 mg/ml fucose dehydrogenase solution is added, followed by 50 ul of 200 uM NAD+. The tubes are mixed and incubated for 3 hours at 4° C. To stop the enzymatic reaction, 50 ul of 1 N NaOH is added to each tube, mixed, and incubated for 10 minutes at 60° C. The tubes are then cooled on ice and the samples are mixed with 50 ul of 1 M hydrochloric to neutralize the samples.

From each sample, a 50 ul aliquot is removed and transferred to a fresh 1.5 ml micro centrifuge tube. To each sample, 250 ul of cycling reagent (200 mM Tris pH 8.4; 50 mM ammonium acetate; 0.5 mM ADP; 100 mM lactate; 5 mM alpha-ketoglutarate; 20 units/ml lactate dehydrogenase; 20 units/ml glutamate dehydrogenase) is added, the solution is mixed, and incubated for 1 hour at room temperature. Heating each tube for 2 minutes in boiling water stops the enzymatic reaction of the cycling reagent.

The tubes are cooled on ice and then 250 ul of pyruvate reagent (800 mM imidazole buffer, pH 6.2; 0.45 mM NADH; 0.06 units/ml lactate dehydrogenase) is added and the tubes mixed. The tubes are then warmed for 1 to 2 minutes at room temperature in a water bath before placement in an incubator at 30° C. for 20 minutes. The pyruvate reaction is stopped by adding 200 ul of 1.5 M HCl to each sample and mixing the solution.

The contents of each tube are then transferred to a 15 ml capped tube and 2.5 ml of 6 N NaOH is added and mixed. The tubes are then incubated for 10 minutes at 60° C. After cooling the samples to room temperature, 4 ml of sterile water is added to each tube, the tubes inverted and then subjected to fluorescence measurement.

A part of each sample (300 ul) is aliquoted into a well of a 96-well microtiter plate. Three to five wells are filled with sterile water and used as blanks. The fluorometer is set using a 360 nm excitation filter and a 465 nm emission filter. The fluorescence of the standards and samples is read and the fluorescence of the blanks subtracted out. The fluorescence readings of the standards are graphed as a standard curve and the amount of fucose in the plasmid DNA samples is determined by interpolation from the standard curve.

Using this method, the fucose levels of plasmid DNA samples were determined and the concentration of colanic acid levels calculated. Colanic acid was consistently found to be the primary contaminant in plasmid DNA from a variety of sources, even GMP grade plasmid DNA.

3. Fluorescent Detection of Gel Electrophoresed DNA Samples

A visual method developed for the detection of polysaccharides in plasmid DNA samples involved labeling of the samples with a substance capable of selectively labeling polysaccharides in a plasmid DNA sample. One such substance is DTAF, (4,6-dichlorotriazinyl) aminofluorescein (Molecular Probes, Eugene, Oreg.). DTAF specifically labels all polysaccharides whether or not they contain uronic acid. This fluorescence probe reacts with hydroxyl groups found in polysaccharides or carbohydrates and is therefore a probe with application beyond the assay method using uronic acid detection.

DTAF does not label DNA, since DNA does not have free hydroxyl groups available. All of the available hydroxyl groups in DNA are phosphorylated. This specificity makes DTAF the preferred label for distinguishing DNA from its polysaccharide contaminants. Although DTAF was used in the method of the present invention, one of skill would understand that any fluorescence label that provides for specificity of labeling between polysaccharides and DNA would be useful in the method of the present invention.

DNA and polysaccharide can be visualized in parallel samples run on one gel. DNA is pretreated with ethidium bromide (EtBr) before adding the samples to the gel. Polysaccharides are labeled with DTAF. A plasmid DNA sample can be run in two lanes on one gel with the sample in one lane stained with EtBr and the sample in the other lane stained with DTAF; thereby, allowing one to visualize the polysaccharide and DNA content of a plasmid DNA sample.

DNA and polysaccharide standards (40 ul of a 2 mg/ml solution) were precipitated by the addition of 10 ul of 3M sodium acetate, pH 5.2, followed by 200 ul of cold ethanol. The samples were incubated for 30 minutes at $-20°$ C., then centrifuged 4 minutes at 10,000 rpm in an Eppendorf microfuge. The precipitates were then suspended in 10 ul sodium acetate plus 200 ul ethanol and recentrifuged. The precipitates were then resuspended in 200 ul ethanol, recentrifuged and dissolved in 50 ul 0.1 M sodium carbonate, pH 10.5.

A fresh DTAF suspension is prepared by suspending 60 mg/ml DTAF in carbonate buffer. Since not all of the DTAF will go into solution, the resulting suspension is vortexed before its addition to each sample. A 5 ul sample of the fresh DTAF suspension (which has been kept dark and cold) is added to the dissolved sample at timed intervals of 0 minutes, 45 minutes, and 90 minutes. Upon each addition of the DTAF suspension, the reaction mixture is vortexed and placed at room temperature in the dark. The reaction is terminated after 2.5 hours by precipitating each sample with the addition of 10 ul sodium acetate and 325 ul ethanol. Incubating these samples for 45 minutes at $-20°$ C. encourages the precipitation. The samples are then centrifuged and the precipitates washed 3 times with 25 ul sodium acetate and 500 ul ethanol. The samples are finally washed with 500 ul ethanol and then dried for 20 minutes at room temperature in the dark.

The washed samples are dissolved in 40 ul Tris Acetate EDTA (TAE) buffer and 2.5 ul to 20 ul of the sample are applied to the gel. DNA samples that were not reacted with DTAF were added to other lanes in the gel in the presence of EtBr. Lambda DNA-Hind III Digest and PhiX174 DNA-HaeIII Digest are run as gel markers.

The gel is a 1% agarose Tris Acetate EDTA gel, pH 8.3. Neither the gel nor the running buffer contain ethidium bromide. The gel is electrophoresed for 45 minutes at 90 volts. It is important to note that the sample buffer must be free of bromophenol blue, which will quench the DTAF fluorescence, except in the Lambda Hind III marker lane.

FIG. 2 shows a gel where several different DNA plasmid samples were tested using this gel electrophoretic method for polysaccharide visualization and quantification. LPS (Sigma Chemical Company, St. Louis, Mo.) and "detoxified" LPS, where the fatty acid portions of the Lipid A have been removed, (Sigma Chemical Company, St. Louis, Mo.) were added as controls in lanes 10 and 8 respectively of the gel. Lanes 1-4 and 12 illustrate the DTAF staining of plasmid DNA samples for which the uronic acid content is given in Table 1. Lane 5, 7, 9, 11 and 13 have no sample loaded. Lane 6 illustrates the DTAF staining of a Qiagen endotoxin free DNA sample (currently considered the gold standard for purified plasmid DNA).

Lanes 14 through 20 of the gel illustrated in FIG. 2 show the results of EtBr staining of different DNA samples. Lanes 14-17 are the same DNA samples stained with EtBr that are stained with DTAF in Lanes 1-4. Lane 18 is the DNA sample shown in Lane 12 stained with EtBr. Lane 19 is the EtBr stain of the Qiagen endotoxin-free DNA sample, shown in Lane 6 stained with DTAF. Lane 20 is a mixture of high and low DNA molecular weight markers labeled with EtBr.

The results showed that the polysaccharides and the DNA migrate at different locations on the gel and that DTAF only labeled polysaccharides contained in the DNA samples and ethidium bromide only labeled DNA. All of the DNA samples, including the Qiagen endotoxin-free DNA, had detectable levels of polysaccharides. LPS and detoxified LPS also contained detectable levels of polysaccharides. Therefore, although the "detoxified" LPS (Sigma Chemical Company, St. Louis, Mo.) has supposedly had all Lipid A removed, there were still significant levels of polysaccharides detected in Lane 8 which contained the detoxified LPS sample.

These data are provided below in Table 3.

TABLE 3

| DNA Plasmid Preparation | Method of Detection | Polysaccharide Detected (mg/mg DNA) |
|---|---|---|
| Boronate-purified plasmid DNA | uronic acid assay | undetectable, $\leq 0.05$ |
| Boronate-purified plasmid DNA | DTAF/EtBr gels | undetectable by visualization |

4. Toxicity of Polysaccharides Found in Plasmid DNA Samples

To determine whether the levels of polysaccharide detected in plasmid DNA samples were clinically significant, acute toxicity studies of the samples were performed in animals. Balb/c mice, six weeks old, were injected intravenously with DNA-liposome complexes, where the liposomes were prepared according to published procedures (Nancy Smyth Templeton, et al. July 1997. *Nature Biotechnology* 15:647-652). Twenty mice in each group were injected and followed for one week post-injection. The results are shown in Table 4.

Results showed that the intravenous injection of 100 ul of DNA containing 0.4 mg polysaccharide per mg DNA caused all of the mice to die within 18 hours post-injection. In contrast, the injection of 50 ul of the same DNA did not cause any of the animals to dies within a week after injection. Similar results were obtained using DNA samples from various sources.

Plasmid DNA containing levels of about 0.26 mg polysaccharide per mg DNA were found to reduce gene expression when 50 ug DNA were injected into immune compromised transgenic mice once a week for three months. When plasmid DNA preparations contained undetectable levels of polysaccharide per mg DNA (<0.03 mg), there were no adverse effects in the animals.

TABLE 4

| Source of DNA | [DNA] | # Mice Injected | # Dead Mice 18 hr Post-Injection | # Dead Mice 1 Wk Post-Injection |
|---|---|---|---|---|
| Clean DNA* | 100 µg | 20 | 0 | 0 |
| Clean DNA* | 50 µg | 20 | 0 | 0 |
| Qiagen Endo-Free | 100 µg | 20 | 20 | NA |
| Qiagen Endo-Free | 50 µg | 20 | 0 | 0 |
| GMP, Company #1 | 100 µg | 20 | 20 | NA |
| GMP, Company #1 | 50 µg | 20 | 0 | 0 |
| GMP, Company #2 | 100 µg | 20 | 20 | NA |
| GMP, Company #2 | 50 µg | 20 | 0 | 0 |
| Clean DNA + 0.4 mg polysaccharide/mg DNA | 100 µg | 20 | 20 | NA |
| Clean DNA + 0.4 mg polysaccharide/mg DNA | 50 µg | 20 | 0 | 0 |
| Liposomes** | 0 | 20 | 0 | 0 |

*Clean DNA contains no detectable polysaccharide as measured by the uronic acid assay or staining with DTAF.
**The quantity of liposomes injected were equivalent to the quantity injected with 100 µl of DNA.

We also performed additional in vivo studies in mice to test our DNA purification procedure using the truncated CAE recombinant protein. These studies were performed in normal mice (Balb/c), and in SCID mice with or without pancreatic tumors. SCID mice are more sensitive to colanic acid and die at iv injections containing 40 ug of commercially produced plasmid DNA complexed to liposomes and other cationic carriers, whereas Balb/c mice die at levels just above 50 ug of plasmid DNA. In the tables show in FIGS. 12-14, we showed that a total of 120 mice survived high doses of DNA-BIV liposomal complexes post-iv injections, purified according to the processes of the invention.

5. Assay for Detecting CAE Using BCA Reagent

Principle: Colanic Acid Enzyme (6×His-CAE) and other carbohydrases increase the reducing ends when degrading their substrates. The miniaturized highly sensitive bicinchoninic acid (BCA) reducing value assay, presented in this protocol detects reducing ends of sugars. This assay can be used for the detection of all carbohydrases degrading any polysaccharide; enzymes with either an exo- or endo-type of mechanisms. However caution should be exercised to reduce background absorbance caused by culture medium, proteins and substrates.

Material and Equipment:
Colanic Acid (CA): 2 µg/µl in 0.05 M potassium phosphate buffer pH 6.5
6×His-CAE: 0.5 µg/µl in 0.05 M potassium phosphate buffer pH 6.5
Bovine Serum Albumin (BSA): 0.5 µg/µl in 0.05 M potassium phosphate buffer pH 6.5
Buffer: 0.05 M potassium phosphate buffer pH 6.5
Micro BCA Protein Assay Kit (Pierce Product #23235)
Optical 96-Well Reaction plate (Applied Biosystems, Part #4306737)
96 Well, Flat bottom Non Tissue Culture tested, Nonsterile PVC Flexible Plate (Falcon#353912) or Fisherbrand Flat Bottom 96 Well plate, clear, PS, non-sterile (Cat#12565501)
Multichannel pipet
96 Well Plate Reader
37° C. and 50° C. Incubator
Centrifuge with rotor for spinning 96 well plate Brief Procedure: Briefly, this assay uses a 96 well format, with each well contains a mixture of 2 µg of CAE (TEST) or BSA (BLANK), 100 µg CA, in a total volume of 110 µl of Buffer which is incubated at 37° C. for 3 hours, and later at 50° C. for 21 hours. Subsequently 100 µl of each reaction mix is transferred to a new 96 well plate, to which 100 µl of freshly prepared BCA reagent is added and allowed to incubate at 37° C. for 2 hours, cooled to RT for 15 min, and readings at 550 nm are taken using a multiplate reader.

Detailed Procedure: In an Optical 96-Well Reaction plate (Applied Biosystems), Aliquot Blank total volume is 110 µl (i.e. Buffer+CA+BSA) in triplicates, i.e. add the following in the same sequence, 56 µl Buffer+50 µl of 2 µg/µl CA+4 µl of 0.5 µg/µl BSA.

Aliquot Test total volume is 110 µl (i.e. Buffer+CA+6×His CAE) in triplicates, i.e. add the following in the sequence, 56 µl Buffer+50 µl of 2 µg/µl CA+4 µl of 0.5 µg/µl 6×His-CAE.

Seal all the wells using the strip caps provided. Spin the plate at 1500 rpm at RT for 1 min. Remove caps from the wells, and mix by gently pipeting up and down three times using Multichannel pipet. Reseal the wells using the caps and incubate plate in 37° C. incubator for 3 hours.

Shift plate to 50° C. incubator and incubate overnight for a total of 21 hours.

Spin plate at 1500 rpm at RT for 1 min.

Use a multichannel pipet to aliquot 100 µl of each well sample to a new 96 well plate (Falcon or Fisherbrand).

Prepare BCA reagent by mixing the three reagents provided in the Micro BCA kit, i.e., MA+MB+MC in a ratio of 0.5:0.48:0.02 using enough to be sufficient for all the wells. Aliquot 100 µl of this freshly prepared BCA reagent to each of the well using a multichannel pipet, mixing gently by pipeting three times up and down. Put lid on 96 well plate, and incubate plate in 37° C. incubator for 2 hours. Let plate cool at room temp for 15 mins, and take reading at 550 nm using multiplate reader.

To get the value of CAE activity subtract values of Blank from the Test. Note: You can take readings at other wavelengths if the Multiplate reader does not allow you to take at 550 nm, For example at 544 nm, 570 nm, 595 nm. But readings are best near to the 550 nm.

References: P. J. A. Meeuwsen, J.-P. Vincken, G. Beldman and A. G. J. Voragen, J. A Universal Assay for screening expression libraries for carbohydrases. Biosci. Bioeng. 89 (2000), pp. 107-109; Verhoef R, Beldman G, Schols H A, Siika-aho M, Rättö M, Buchert J, Voragen A G. Characterisation of a 1,4-beta-fucoside hydrolase degrading colanic acid. Carbohydr Res. 2005 Aug. 15; 340(11): 1780-1788.

6A. Viscosity Assay for the Detection of CAE in Plasmid DNA Preparations

Principle: Colanic Acid (CA) is viscous, and there is a reduction of its viscosity when it is catalytically degraded by Colanic Acid Enzyme (6×His-CAE). This drop in viscosity can be accurately measured using a viscometer and can be used to calculate activity of CAE by comparing it to the values obtained using a Control reaction i.e., containing CA but in the absence of the enzyme.

Material and Equipment:
Colanic Acid (CA) 1.2 mg/ml in 0.05 M Potassium Phosphate Buffer pH 6.5
Colanic Acid Enzyme (6×His-CAE) 1.0 μg/μl in 0.05 M Potassium Phosphate Buffer pH 6.5
Buffer: 0.05 M Potassium Phosphate Buffer pH 6.5
Water Bath at 37° C.
Brookfield DV-I+Viscometer
Brookfield CPE 40 spindle Brief Procedure:
600 μg CA was mixed with 1 μg CAE in the presence of 0.05 M Pot Phosphate Buffer pH 6.5, in a total volume of 500 μl. Mix an incubate at 37° C. using a water bath. Let cool to RT for 10 min, and take readings using a viscometer. This is compared to a Control reaction in the absence of CAE.

Detailed Procedure:
For CONTROL, in a 1.5 ml eppendorf tube, aliquot 0.5 ml of 1.2 mg/ml CA+50 μl 0.05 M Pot Phosphate Buffer pH 6.5.

For TEST, in a 1.5 ml eppendorf tube, aliquot 0.5 ml of 1.2 mg/ml CA+1 μl of 6×His-CAE (1.0 μg/μl)+49 μl 0.05 M Pot Phosphate Buffer pH 6.5.

Mix by gently pipeting up and down, and incubate at 37° C. for 1 hour using a water bath. Remove tubes from water bath and let cool to RT for 10 min.

Measure Viscosity of Test and Control using a Brookfield DV+Viscometer, set at 100 rpm, for 30 seconds using 0.5 ml of the respective reaction mix aliquoted into a CPE 40 spindle.

Note down Viscosity values as CentiPoise (cP) for both Test and Control, and calculate CAE activity using cP values as follows: The calculation is based on the fact that water which has no viscosity has a cP value of 1.00. If CAE has 100% activity it would reduce the viscosity of CA to a cP value of 1.00. Hence for eg If the CONTROL has a cP value of 1.57, we would subtract 1.00 from it to get a value of 1.57−1.00=0.57 which represents 100% activity (that is if the cP value drops by 0.57 in the test it would have 100% CAE activity). If the TEST has a cP value of 1.05, we would similarly subtract this cP value from that of the Control. i.e. 1.57−1.05=0.52, this figure would be used to calculate actual CAE activity as follows: 0.57 is 100% activity, hence 0.52 is how much % activity ? 0.52 multiplied by 100 and divided by 0.57=91.22% CAE activity.

6B. Viscometry Testing for Identification of CAE Activity

A bioassay measuring changes in the viscosity of colanic acid samples was used to detect CAE. A decrease the viscosity of colanic acid samples was indicative of CAE activity. The viscosity of the colanic acid samples, before and after incubation with an enzyme fraction, was measured using a Wells-Brookfield Cone Plate viscometer with a CPE-40 cone. This viscometer provided the most sensitive measurement of changes in viscosity in small volumes of about 500 ul. Viscometer accuracy was monitored by measuring the viscosity of a mineral oil standard and comparing the reading with the known viscosity for mineral oil.

The CAE assay utilized a 500 ul sample of a 1.5% colanic acid solution. Diluted enzyme samples or controls samples, between 50 to 100 ul, was added to the 1.5% colanic acid solution. Controls for the enzyme assays were prepared by adding the diluted enzyme samples to buffer and by adding non-proteinaceous samples to the 1.5% colanic acid solution. Each test sample (enzyme samples or control samples) was incubated for one hour at 37° C. After the one hour incubation, the test samples were allowed to adjust to room temperature for 10 minutes.

The viscosity of all test samples was taken at room temperature for 30 seconds at 100 rpm. All test samples having CAE activity, isolated and purified as described above, demonstrated a significant decrease in viscosity, as compared to the control samples that showed no change in viscosity. The CAE test samples decreased the viscosity of the 1.5% colanic acid solution from 1.51 to 0.99, where 0.99 was the lowest viscometry reading obtainable using the Wells-Brookfield Cone Plate viscometer and was equal to the viscometry reading of the buffer controls.

Therefore, the present invention provides both a method of detection and quantification of polysaccharides in plasmid DNA samples and a method for removing polysaccharide from plasmid DNA samples to levels of polysaccharides below levels that produce clinically significant toxicity.

It is to be understood that this invention is capable of other embodiments and of being practiced and carried out in various ways. Also, it is to be understood that the phraseology and terminology employed herein is for the purposes of description and should not be regarded as limiting.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An isolated polynucleotide comprising a nucleic acid sequence that encodes a polypeptide having colanic acid degrading activity having at least 98% sequence identity with SEQ ID NO: 1, or the complement thereof.

2. The polynucleotide of claim 1, wherein the polypeptide has at least 99% sequence identity with SEQ ID NO: 1, or the complement thereof.

3. The polynucleotide of claim 1, wherein the nucleic acid sequence is SEQ ID NO: 7.

4. A vector comprising the polynucleotide of claim 1, wherein the vector is selected from the group consisting of a plasmid, a virus, and a bacteriophage, and wherein the nucleic acid is operably linked to a heterologous promoter.

5. The vector of claim 4, wherein the vector is a plasmid or a bacteriophage.

6. The vector of claim 4, wherein the vector is a bacteriophage.

7. The vector of claim 4, wherein the nucleic acid encodes a polypeptide having at least 99% sequence identity with SEQ ID NO:1, or the complement thereof.

8. The vector of claim 4, wherein the nucleic acid sequence is SEQ ID NO: 7.

9. An isolated polynucleotide comprising a nucleic acid sequence encoding a polypeptide having colanic acid degrading activity having at least 98% sequence identity with SEQ ID NO: 2, or the complement thereof.

10. The polynucleotide of claim 9, wherein the nucleic acid encodes a polypeptide having at least 99% sequence identity with SEQ ID NO: 2, or the complement thereof.

11. The polynucleotide of claim 9, wherein the nucleic acid sequence is SEQ ID NO: 8.

12. A vector comprising the polynucleotide of claim 9, wherein the vector is selected from the group consisting of a plasmid, a virus, and a bacteriophage, and wherein the nucleic acid is operably linked to a heterologous promoter.

13. The vector of claim 12, wherein the vector is a plasmid or a bacteriophage.

14. The vector of claim 12, wherein the vector is a bacteriophage.

15. The vector of claim 12, wherein the nucleic acid encodes a polypeptide having at least 99% sequence identity with SEQ ID NO: 2, or the complement thereof.

16. The vector of claim 12, wherein the nucleic acid sequence is SEQ ID NO: 8.

17. A method of making a recombinant polypeptide comprising: transforming a cell with a recombinant vector comprising a nucleic acid sequence encoding a polypeptide having colanic acid degrading activity and at least 98% sequence identity with at least one of SEQ ID NO: 1 or SEQ ID NO: 2, and growing the cell under conditions in which the cell expresses the polypeptide.

18. The method of claim 17, wherein the vector is selected from the group consisting of a plasmid, a virus, and a bacteriophage, wherein the nucleic acid is operably linked to a heterologous promoter.

19. The method of claim 17, wherein the nucleic acid sequence encodes a polypeptide having at least 99% sequence identity with at least one of SEQ ID NO:1 or SEQ ID NO:2.

20. A host cell transformed with a recombinant vector that comprises a polynucleotide comprising a nucleic acid sequence encoding a polypeptide having colanic acid degrading activity and at least 98% sequence identity with at least one of SEQ ID NO:1 or SEQ ID NO:2, wherein the nucleic acid is operably linked to a heterologous promoter.

21. The host cell of claim 20, wherein the polynucleotide comprises a nucleic acid sequence that encodes a polypeptide having at least 99% sequence identity with SEQ ID NO:1 or SEQ ID NO:2.

22. The host cell of claim 20, wherein the recombinant vector is selected from the group consisting of a plasmid, a virus, and a bacteriophage.

23. The host cell of claim 20, wherein the nucleic acid sequence is SEQ ID NO: 7 or SEQ ID NO: 8.

24. The host cell of claim 20, wherein the nucleic acid sequence is SEQ ID NO: 7 or SEQ ID NO: 8.

* * * * *

SEQUENCE LISTING

```
<160> NUMBER OF SEQ ID NOS: 17

<210> SEQ ID NO 1
<211> LENGTH: 790
<212> TYPE: PRT
<213> ORGANISM: Artificial
<220> FEATURE:
<223> OTHER INFORMATION: Amino acid sequence for colanic acid degrading
      enzyme (CAE), derived from Bacteriophage (NST1).

<400> SEQUENCE: 1
```

-continued

```
Met Ala Asn Ser Tyr Asn Ala Tyr Val Ala Asn Gly Ser Gln Thr Ala
1               5                   10                  15

Phe Leu Val Thr Phe Glu Gln Arg Val Phe Thr Glu Ile Gln Val Tyr
            20                  25                  30

Leu Asn Ser Glu Leu Gln Thr Glu Gly Tyr Thr Tyr Asn Ser Val Thr
        35                  40                  45

Lys Gln Ile Ile Phe Asp Thr Ala Pro Leu Ala Gly Val Ile Val Arg
    50                  55                  60

Leu Gln Arg Tyr Thr Ser Glu Val Leu Leu Asn Lys Phe Gly Gln Asp
65                  70                  75                  80

Ala Ala Phe Thr Gly Gln Asn Leu Asp Glu Asn Phe Glu Gln Ile Leu
                85                  90                  95

Phe Lys Ala Glu Glu Thr Gln Glu Ala Trp Leu Ala Pro Leu Asp Arg
            100                 105                 110

Ala Val Arg Val Pro Asn Ser Glu Val Ser Ile Asn Ala Leu Pro Asn
        115                 120                 125

Val Ala Gly Arg Arg Asn Lys Ala Leu Gly Phe Asp Ser Asn Gly Gln
    130                 135                 140

Pro Phe Met Ile Pro Leu Val Asp Ile Pro Asp Ser Ala Leu Ala Ile
145                 150                 155                 160

Ala Leu Ala Met Ala Asp Gly Gly Lys Trp Ile Gly Thr Leu Gly Gly
                165                 170                 175

Gly Thr Phe Leu Asp Arg Gln Asp Thr Val Cys Leu Ser Glu Phe Thr
            180                 185                 190

Asn Asn Thr Gly Tyr Ala Ser Val Ala Ala Val Gln Ala Cys Phe
        195                 200                 205

Asp Tyr Ala Lys Ala Asn Gly Lys Val Val Asp Ala Arg Gly Trp Glu
    210                 215                 220

Gly Thr Val Asp Ser Thr Val Leu Met Asp Gly Ile Glu Val Val Gly
225                 230                 235                 240

Gly Thr Trp His Gly Lys Ala Asp Ile Arg Leu Leu Asn Ser Thr Phe
                245                 250                 255

Arg Asn Phe Val Ala Ser Thr Val Arg Val Ala Tyr Trp Gly Gly Glu
            260                 265                 270

Val Arg Ile Ala Asp Tyr Glu Phe Thr Ser Ala Pro Ser Asn Ser Lys
        275                 280                 285

Val Thr Ser Ile Leu Phe Gln Gly Asn Ile Ala Gly Gly Ser Tyr Val
    290                 295                 300

Ile Glu Asn Gly Ile His Arg Asn Gly Lys Phe Gly Ile Leu Gln Gln
305                 310                 315                 320

Gly Thr Gly Glu Ala Ile Thr Asn Gly Val Ile Arg Gly Ile Thr Met
                325                 330                 335

Met Asp Met Gln Gly Asp Gly Ile Glu Met Asn Val Ile Asn Lys His
            340                 345                 350

Tyr Asp Gly Gly Leu Leu Ile Glu Asn Ile Phe Leu Glu Asn Ile Asp
        355                 360                 365

Gly Thr Asn Ala Pro Ile Pro Leu Ser Asn Trp Gly Ile Gly Ile Gly
    370                 375                 380

Ile Ala Gly Gln Gly Pro Phe Gly Trp Asp Ala Ala Glu Thr Gln Tyr
385                 390                 395                 400

Ala Lys Asn Val Thr Val Arg Asn Val His Ala Pro Arg Gly Val Arg
                405                 410                 415

Gln Val Val His Phe Glu Val Thr Arg Asp Ser Thr Cys Glu Asn Val
```

```
                    420               425               430
Val Ala Asn Pro Asp Leu Ser Val Ser Ile Gly Thr Gly Leu Thr Ala
                435               440               445

Ala Gly Val Ile Thr Tyr Gly Cys Lys Arg Met Thr Ile Asp Gly Val
            450               455               460

Val Gly Glu Pro Met Asn Thr Gly Ala Thr Ser Pro Asn Asp Ile Arg
465               470               475               480

Ile Val Met Leu Glu Trp Gly Ala Asn Gln Ala Gly Ala Gly Gly Thr
                485               490               495

Pro Gly Ala Ala Cys Pro Ser Phe Asp Met Thr Val Arg Asn Val Gln
            500               505               510

Thr Arg Thr Gly Arg Phe Tyr Ala Gly Val Gly Ser Asp Asp Asp Asn
            515               520               525

Thr Asn Thr Tyr His Leu Glu Asn Ile His Cys Tyr Lys Met Thr Leu
            530               535               540

Phe Gly Val Ala Thr Leu Leu Asn Met Thr Asn Val Thr Gly Val Val
545               550               555               560

Phe Asp Ala Val Gly Asp Asp Ser Ser Gly Gly Thr Ser Ser Asn Gly
                565               570               575

Leu Tyr Pro Arg Lys Lys Thr Val Leu Asn Met Val Asn Val Asn Phe
                580               585               590

Tyr Gly Pro Gly Met Thr Glu Gly Ala Leu Tyr Ser Lys Ala Arg Tyr
                595               600               605

Ser Asp Ile Ser Thr Leu Asn Ser Asn Val Arg Ala Ile Pro Tyr Thr
            610               615               620

Asn Ile Gln Gly Asn Val Gly Val Ile Leu Ser Pro Val Asn Arg Met
625               630               635               640

Tyr Thr Leu Pro Asn Ala Leu Ala Thr Leu Asp Gly Asn Glu Phe Pro
                645               650               655

Thr Gly Lys Glu Phe Cys Glu Gly Thr Val Leu Phe Lys Thr Asp Gly
                660               665               670

Ser Gly Gly Asn Phe Ile Val Thr Arg Phe Gly Ala Tyr Ile Pro Asp
            675               680               685

Asp Gly Asn Asn Phe Lys Val Arg Ala Ala Ala Gly Gln Thr Tyr
            690               695               700

Leu Glu Gln Asn Leu Thr Pro Ala Gly Thr Gln Ala Ser Thr Ser Trp
705               710               715               720

Leu Tyr His Lys Pro Ile Ser Ala Gly Thr Arg Leu Asn Val Pro Gly
                725               730               735

Ala Gly Pro Ser Gly Gly Thr Leu Thr Val Thr Val Arg Ala Pro
                740               745               750

Tyr Gln Val Asp Asn Asn Ile Gly Asn Pro Val Arg Ile Asp Ile Thr
            755               760               765

Pro Ala Ile Val Thr Ala Ile Pro Ala Gly Thr Gln Leu Ala Ala Thr
            770               775               780

Tyr Pro Val Ala Tyr Ile
785               790

<210> SEQ ID NO 2
<211> LENGTH: 684
<212> TYPE: PRT
<213> ORGANISM: Artificial
<220> FEATURE:
<223> OTHER INFORMATION: Amino acid sequence for truncated colanic acid
      degrading enzyme (CAE).
```

```
<400> SEQUENCE: 2

Leu Ala Pro Leu Asp Arg Ala Val Arg Val Pro Asn Ser Glu Val Ser
1               5                   10                  15

Ile Asn Ala Leu Pro Asn Val Ala Gly Arg Arg Asn Lys Ala Leu Gly
            20                  25                  30

Phe Asp Ser Asn Gly Gln Pro Phe Met Ile Pro Leu Val Asp Ile Pro
        35                  40                  45

Asp Ser Ala Leu Ala Ile Ala Leu Ala Met Ala Asp Gly Gly Lys Trp
    50                  55                  60

Ile Gly Thr Leu Gly Gly Gly Thr Phe Leu Asp Arg Gln Asp Thr Val
65                  70                  75                  80

Cys Leu Ser Glu Phe Thr Asn Asn Thr Gly Tyr Ala Ser Val Ala Ala
                85                  90                  95

Ala Val Gln Ala Cys Phe Asp Tyr Ala Lys Ala Asn Gly Lys Val Val
            100                 105                 110

Asp Ala Arg Gly Trp Glu Gly Thr Val Asp Ser Thr Val Leu Met Asp
        115                 120                 125

Gly Ile Glu Val Val Gly Gly Thr Trp His Gly Lys Ala Asp Ile Arg
    130                 135                 140

Leu Leu Asn Ser Thr Phe Arg Asn Phe Val Ala Ser Thr Val Arg Val
145                 150                 155                 160

Ala Tyr Trp Gly Gly Glu Val Arg Ile Ala Asp Tyr Glu Phe Thr Ser
                165                 170                 175

Ala Pro Ser Asn Ser Lys Val Thr Ser Ile Leu Phe Gln Gly Asn Ile
            180                 185                 190

Ala Gly Gly Ser Tyr Val Ile Glu Asn Gly Ile His Arg Asn Gly Lys
        195                 200                 205

Phe Gly Ile Leu Gln Gln Gly Thr Gly Glu Ala Ile Thr Asn Gly Val
    210                 215                 220

Ile Arg Gly Ile Thr Met Met Asp Met Gln Gly Asp Gly Ile Glu Met
225                 230                 235                 240

Asn Val Ile Asn Lys His Tyr Asp Gly Gly Leu Leu Ile Glu Asn Ile
                245                 250                 255

Phe Leu Glu Asn Ile Asp Gly Thr Asn Ala Pro Ile Pro Leu Ser Asn
            260                 265                 270

Trp Gly Ile Gly Ile Gly Ile Ala Gly Gln Gly Pro Phe Gly Trp Asp
        275                 280                 285

Ala Ala Glu Thr Gln Tyr Ala Lys Asn Val Thr Val Arg Asn Val His
    290                 295                 300

Ala Pro Arg Gly Val Arg Gln Val Val His Phe Glu Val Thr Arg Asp
305                 310                 315                 320

Ser Thr Cys Glu Asn Val Val Ala Asn Pro Asp Leu Ser Val Ser Ile
                325                 330                 335

Gly Thr Gly Leu Thr Ala Ala Gly Val Ile Thr Tyr Gly Cys Lys Arg
            340                 345                 350

Met Thr Ile Asp Gly Val Val Gly Glu Pro Met Asn Thr Gly Ala Thr
        355                 360                 365

Ser Pro Asn Asp Ile Arg Ile Val Met Leu Glu Trp Gly Ala Asn Gln
    370                 375                 380

Ala Gly Ala Gly Gly Thr Pro Gly Ala Ala Cys Pro Ser Phe Asp Met
385                 390                 395                 400

Thr Val Arg Asn Val Gln Thr Arg Thr Gly Arg Phe Tyr Ala Gly Val
                405                 410                 415
```

-continued

```
Gly Ser Asp Asp Asn Thr Asn Thr Tyr His Leu Glu Asn Ile His
            420                 425                 430

Cys Tyr Lys Met Thr Leu Phe Gly Val Ala Thr Leu Leu Asn Met Thr
            435                 440                 445

Asn Val Thr Gly Val Val Phe Asp Ala Val Gly Asp Asp Ser Ser Gly
        450                 455                 460

Gly Thr Ser Ser Asn Gly Leu Tyr Pro Arg Lys Lys Thr Val Leu Asn
465                 470                 475                 480

Met Val Asn Val Asn Phe Tyr Pro Gly Met Thr Glu Gly Ala Leu
                485                 490                 495

Tyr Ser Lys Ala Arg Tyr Ser Asp Ile Ser Thr Leu Asn Ser Asn Val
            500                 505                 510

Arg Ala Ile Pro Tyr Thr Asn Ile Gln Gly Asn Val Gly Val Ile Leu
            515                 520                 525

Ser Pro Val Asn Arg Met Tyr Thr Leu Pro Asn Ala Leu Ala Thr Leu
        530                 535                 540

Asp Gly Asn Glu Phe Pro Thr Gly Lys Glu Phe Cys Glu Gly Thr Val
545                 550                 555                 560

Leu Phe Lys Thr Asp Gly Ser Gly Gly Asn Phe Ile Val Thr Arg Phe
                565                 570                 575

Gly Ala Tyr Ile Pro Asp Asp Gly Asn Asn Phe Lys Val Arg Ala Ala
            580                 585                 590

Ala Ala Gly Gln Thr Tyr Leu Glu Gln Asn Leu Thr Pro Ala Gly Thr
            595                 600                 605

Gln Ala Ser Thr Ser Trp Leu Tyr His Lys Pro Ile Ser Ala Gly Thr
        610                 615                 620

Arg Leu Asn Val Pro Gly Ala Gly Pro Ser Gly Gly Thr Leu Thr Val
625                 630                 635                 640

Thr Val Val Arg Ala Pro Tyr Gln Val Asp Asn Asn Ile Gly Asn Pro
                645                 650                 655

Val Arg Ile Asp Ile Thr Pro Ala Ile Val Thr Ala Ile Pro Ala Gly
            660                 665                 670

Thr Gln Leu Ala Ala Thr Tyr Pro Val Ala Tyr Ile
        675                 680
```

<210> SEQ ID NO 3
<211> LENGTH: 798
<212> TYPE: PRT
<213> ORGANISM: Artificial
<220> FEATURE:
<223> OTHER INFORMATION: Amino acid sequence for HIS-tagged colanic acid
      degrading enzyme (CAE).

<400> SEQUENCE: 3

```
Met Gly His His His His His His Met Ala Asn Ser Tyr Asn Ala Tyr
1               5                   10                  15

Val Ala Asn Gly Ser Gln Thr Ala Phe Leu Val Thr Phe Glu Gln Arg
            20                  25                  30

Val Phe Thr Glu Ile Gln Val Tyr Leu Asn Ser Glu Leu Gln Thr Glu
        35                  40                  45

Gly Tyr Thr Tyr Asn Ser Val Thr Lys Gln Ile Ile Phe Asp Thr Ala
    50                  55                  60

Pro Leu Ala Gly Val Ile Val Arg Leu Gln Arg Tyr Thr Ser Glu Val
65                  70                  75                  80

Leu Leu Asn Lys Phe Gly Gln Asp Ala Ala Phe Thr Gly Gln Asn Leu
                85                  90                  95
```

-continued

```
Asp Glu Asn Phe Glu Gln Ile Leu Phe Lys Ala Glu Thr Gln Glu
                100                 105                 110
Ala Trp Leu Ala Pro Leu Asp Arg Ala Val Arg Val Pro Asn Ser Glu
    115                 120                 125
Val Ser Ile Asn Ala Leu Pro Asn Val Ala Gly Arg Arg Asn Lys Ala
130                 135                 140
Leu Gly Phe Asp Ser Asn Gly Gln Pro Phe Met Ile Pro Leu Val Asp
145                 150                 155                 160
Ile Pro Asp Ser Ala Leu Ala Ile Ala Leu Ala Met Ala Asp Gly Gly
                165                 170                 175
Lys Trp Ile Gly Thr Leu Gly Gly Thr Phe Leu Asp Arg Gln Asp
    180                 185                 190
Thr Val Cys Leu Ser Glu Phe Thr Asn Asn Thr Gly Tyr Ala Ser Val
    195                 200                 205
Ala Ala Ala Val Gln Ala Cys Phe Asp Tyr Ala Lys Ala Asn Gly Lys
    210                 215                 220
Val Val Asp Ala Arg Gly Trp Glu Gly Thr Val Asp Ser Thr Val Leu
225                 230                 235                 240
Met Asp Gly Ile Glu Val Val Gly Gly Thr Trp His Gly Lys Ala Asp
                245                 250                 255
Ile Arg Leu Leu Asn Ser Thr Phe Arg Asn Phe Val Ala Ser Thr Val
            260                 265                 270
Arg Val Ala Tyr Trp Gly Gly Glu Val Arg Ile Ala Asp Tyr Glu Phe
        275                 280                 285
Thr Ser Ala Pro Ser Asn Ser Lys Val Thr Ser Ile Leu Phe Gln Gly
    290                 295                 300
Asn Ile Ala Gly Gly Ser Tyr Val Ile Glu Asn Gly Ile His Arg Asn
305                 310                 315                 320
Gly Lys Phe Gly Ile Leu Gln Gln Gly Thr Gly Glu Ala Ile Thr Asn
                325                 330                 335
Gly Val Ile Arg Gly Ile Thr Met Met Asp Met Gln Gly Asp Gly Ile
            340                 345                 350
Glu Met Asn Val Ile Asn Lys His Tyr Asp Gly Gly Leu Leu Ile Glu
        355                 360                 365
Asn Ile Phe Leu Glu Asn Ile Asp Gly Thr Asn Ala Pro Ile Pro Leu
    370                 375                 380
Ser Asn Trp Gly Ile Gly Ile Gly Ile Ala Gly Gln Gly Pro Phe Gly
385                 390                 395                 400
Trp Asp Ala Ala Glu Thr Gln Tyr Ala Lys Asn Val Thr Val Arg Asn
                405                 410                 415
Val His Ala Pro Arg Gly Val Arg Gln Val His Phe Glu Val Thr
            420                 425                 430
Arg Asp Ser Thr Cys Glu Asn Val Val Ala Asn Pro Asp Leu Ser Val
    435                 440                 445
Ser Ile Gly Thr Gly Leu Thr Ala Ala Gly Val Ile Thr Tyr Gly Cys
    450                 455                 460
Lys Arg Met Thr Ile Asp Gly Val Val Gly Glu Pro Met Asn Thr Gly
465                 470                 475                 480
Ala Thr Ser Pro Asn Asp Ile Arg Ile Val Met Leu Glu Trp Gly Ala
                485                 490                 495
Asn Gln Ala Gly Ala Gly Gly Thr Pro Gly Ala Ala Cys Pro Ser Phe
            500                 505                 510
Asp Met Thr Val Arg Asn Val Gln Thr Arg Thr Gly Arg Phe Tyr Ala
        515                 520                 525
```

```
Gly Val Gly Ser Asp Asp Asn Thr Asn Thr Tyr His Leu Glu Asn
            530                 535                 540

Ile His Cys Tyr Lys Met Thr Leu Phe Gly Val Ala Thr Leu Leu Asn
545                 550                 555                 560

Met Thr Asn Val Thr Gly Val Val Phe Asp Ala Val Gly Asp Asp Ser
                565                 570                 575

Ser Gly Gly Thr Ser Ser Asn Gly Leu Tyr Pro Arg Lys Lys Thr Val
            580                 585                 590

Leu Asn Met Val Asn Val Asn Phe Tyr Gly Pro Gly Met Thr Glu Gly
            595                 600                 605

Ala Leu Tyr Ser Lys Ala Arg Tyr Ser Asp Ile Ser Thr Leu Asn Ser
            610                 615                 620

Asn Val Arg Ala Ile Pro Tyr Thr Asn Ile Gln Gly Asn Val Gly Val
625                 630                 635                 640

Ile Leu Ser Pro Val Asn Arg Met Tyr Thr Leu Pro Asn Ala Leu Ala
                645                 650                 655

Thr Leu Asp Gly Asn Glu Phe Pro Thr Gly Lys Glu Phe Cys Glu Gly
            660                 665                 670

Thr Val Leu Phe Lys Thr Asp Gly Ser Gly Gly Asn Phe Ile Val Thr
            675                 680                 685

Arg Phe Gly Ala Tyr Ile Pro Asp Asp Gly Asn Asn Phe Lys Val Arg
690                 695                 700

Ala Ala Ala Ala Gly Gln Thr Tyr Leu Glu Gln Asn Leu Thr Pro Ala
705                 710                 715                 720

Gly Thr Gln Ala Ser Thr Ser Trp Leu Tyr His Lys Pro Ile Ser Ala
                725                 730                 735

Gly Thr Arg Leu Asn Val Pro Gly Ala Gly Pro Ser Gly Gly Thr Leu
            740                 745                 750

Thr Val Thr Val Val Arg Ala Pro Tyr Gln Val Asp Asn Asn Ile Gly
            755                 760                 765

Asn Pro Val Arg Ile Asp Ile Thr Pro Ala Ile Val Thr Ala Ile Pro
            770                 775                 780

Ala Gly Thr Gln Leu Ala Ala Thr Tyr Pro Val Ala Tyr Ile
785                 790                 795

<210> SEQ ID NO 4
<211> LENGTH: 692
<212> TYPE: PRT
<213> ORGANISM: Artificial
<220> FEATURE:
<223> OTHER INFORMATION: Amino acid sequence for HIS-tagged truncated
      form of colanic acid degrading enzyme (CAE).

<400> SEQUENCE: 4

Met Gly His His His His His His Leu Ala Pro Leu Asp Arg Ala Val
1               5                   10                  15

Arg Val Pro Asn Ser Glu Val Ser Ile Asn Ala Leu Pro Asn Val Ala
                20                  25                  30

Gly Arg Arg Asn Lys Ala Leu Gly Phe Asp Ser Asn Gly Gln Pro Phe
            35                  40                  45

Met Ile Pro Leu Val Asp Ile Pro Asp Ser Ala Leu Ala Ile Ala Leu
        50                  55                  60

Ala Met Ala Asp Gly Gly Lys Trp Ile Gly Thr Leu Gly Gly Gly Thr
65                  70                  75                  80

Phe Leu Asp Arg Gln Asp Thr Val Cys Leu Ser Glu Phe Thr Asn Asn
                85                  90                  95
```

```
Thr Gly Tyr Ala Ser Val Ala Ala Val Gln Ala Cys Phe Asp Tyr
            100                 105                 110
Ala Lys Ala Asn Gly Lys Val Val Asp Ala Arg Gly Trp Glu Gly Thr
            115                 120                 125
Val Asp Ser Thr Val Leu Met Asp Gly Ile Glu Val Gly Gly Thr
            130                 135                 140
Trp His Gly Lys Ala Asp Ile Arg Leu Leu Asn Ser Thr Phe Arg Asn
145                 150                 155                 160
Phe Val Ala Ser Thr Val Arg Val Ala Tyr Trp Gly Gly Glu Val Arg
                165                 170                 175
Ile Ala Asp Tyr Glu Phe Thr Ser Ala Pro Ser Asn Ser Lys Val Thr
                180                 185                 190
Ser Ile Leu Phe Gln Gly Asn Ile Ala Gly Ser Tyr Val Ile Glu
            195                 200                 205
Asn Gly Ile His Arg Asn Gly Lys Phe Gly Ile Leu Gln Gln Gly Thr
            210                 215                 220
Gly Glu Ala Ile Thr Asn Gly Val Ile Arg Gly Ile Thr Met Met Asp
225                 230                 235                 240
Met Gln Gly Asp Gly Ile Glu Met Asn Val Ile Asn Lys His Tyr Asp
                245                 250                 255
Gly Gly Leu Leu Ile Glu Asn Ile Phe Leu Glu Asn Ile Asp Gly Thr
                260                 265                 270
Asn Ala Pro Ile Pro Leu Ser Asn Trp Gly Ile Gly Ile Gly Ile Ala
            275                 280                 285
Gly Gln Gly Pro Phe Gly Trp Asp Ala Ala Glu Thr Gln Tyr Ala Lys
            290                 295                 300
Asn Val Thr Val Arg Asn Val His Ala Pro Arg Gly Val Arg Gln Val
305                 310                 315                 320
Val His Phe Glu Val Thr Arg Asp Ser Thr Cys Glu Asn Val Val Ala
                325                 330                 335
Asn Pro Asp Leu Ser Val Ser Ile Gly Thr Gly Leu Thr Ala Ala Gly
                340                 345                 350
Val Ile Thr Tyr Gly Cys Lys Arg Met Thr Ile Asp Gly Val Val Gly
            355                 360                 365
Glu Pro Met Asn Thr Gly Ala Thr Ser Pro Asn Asp Ile Arg Ile Val
            370                 375                 380
Met Leu Glu Trp Gly Ala Asn Gln Ala Gly Ala Gly Gly Thr Pro Gly
385                 390                 395                 400
Ala Ala Cys Pro Ser Phe Asp Met Thr Val Arg Asn Val Gln Thr Arg
                405                 410                 415
Thr Gly Arg Phe Tyr Ala Gly Val Gly Ser Asp Asp Asn Thr Asn
            420                 425                 430
Thr Tyr His Leu Glu Asn Ile His Cys Tyr Lys Met Thr Leu Phe Gly
            435                 440                 445
Val Ala Thr Leu Leu Asn Met Thr Asn Val Thr Gly Val Val Phe Asp
            450                 455                 460
Ala Val Gly Asp Asp Ser Ser Gly Gly Thr Ser Ser Asn Gly Leu Tyr
465                 470                 475                 480
Pro Arg Lys Lys Thr Val Leu Asn Met Val Asn Val Asn Phe Tyr Gly
                485                 490                 495
Pro Gly Met Thr Glu Gly Ala Leu Tyr Ser Lys Ala Arg Tyr Ser Asp
                500                 505                 510
Ile Ser Thr Leu Asn Ser Asn Val Arg Ala Ile Pro Tyr Thr Asn Ile
```

```
                  515                 520                 525
Gln Gly Asn Val Gly Val Ile Leu Ser Pro Val Asn Arg Met Tyr Thr
        530                 535                 540

Leu Pro Asn Ala Leu Ala Thr Leu Asp Gly Asn Glu Phe Pro Thr Gly
545                 550                 555                 560

Lys Glu Phe Cys Glu Gly Thr Val Leu Phe Lys Thr Asp Gly Ser Gly
                565                 570                 575

Gly Asn Phe Ile Val Thr Arg Phe Gly Ala Tyr Ile Pro Asp Asp Gly
            580                 585                 590

Asn Asn Phe Lys Val Arg Ala Ala Ala Gly Gln Thr Tyr Leu Glu
        595                 600                 605

Gln Asn Leu Thr Pro Ala Gly Thr Gln Ala Ser Thr Ser Trp Leu Tyr
    610                 615                 620

His Lys Pro Ile Ser Ala Gly Thr Arg Leu Asn Val Pro Gly Ala Gly
625                 630                 635                 640

Pro Ser Gly Gly Thr Leu Thr Val Thr Val Arg Ala Pro Tyr Gln
                645                 650                 655

Val Asp Asn Asn Ile Gly Asn Pro Val Arg Ile Asp Ile Thr Pro Ala
            660                 665                 670

Ile Val Thr Ala Ile Pro Ala Gly Thr Gln Leu Ala Ala Thr Tyr Pro
        675                 680                 685

Val Ala Tyr Ile
        690

<210> SEQ ID NO 5
<211> LENGTH: 798
<212> TYPE: PRT
<213> ORGANISM: Artificial
<220> FEATURE:
<223> OTHER INFORMATION: Amino acid sequence for FLAG-tagged colanic
      acid degrading enzyme (CAE).

<400> SEQUENCE: 5

Met Ala Asn Ser Tyr Asn Ala Tyr Val Ala Asn Gly Ser Gln Thr Ala
1               5                   10                  15

Phe Leu Val Thr Phe Glu Gln Arg Val Phe Thr Glu Ile Gln Val Tyr
                20                  25                  30

Leu Asn Ser Glu Leu Gln Thr Glu Gly Tyr Thr Tyr Asn Ser Val Thr
            35                  40                  45

Lys Gln Ile Ile Phe Asp Thr Ala Pro Leu Ala Gly Val Ile Val Arg
        50                  55                  60

Leu Gln Arg Tyr Thr Ser Glu Val Leu Leu Asn Lys Phe Gly Gln Asp
65                  70                  75                  80

Ala Ala Phe Thr Gly Gln Asn Leu Asp Glu Asn Phe Glu Gln Ile Leu
                85                  90                  95

Phe Lys Ala Glu Glu Thr Gln Glu Ala Trp Leu Ala Pro Leu Asp Arg
                100                 105                 110

Ala Val Arg Val Pro Asn Ser Glu Val Ser Ile Asn Ala Leu Pro Asn
            115                 120                 125

Val Ala Gly Arg Arg Asn Lys Ala Leu Gly Phe Asp Ser Asn Gly Gln
        130                 135                 140

Pro Phe Met Ile Pro Leu Val Asp Ile Pro Asp Ser Ala Leu Ala Ile
145                 150                 155                 160

Ala Leu Ala Met Ala Asp Gly Gly Lys Trp Ile Gly Thr Leu Gly Gly
                165                 170                 175

Gly Thr Phe Leu Asp Arg Gln Asp Thr Val Cys Leu Ser Glu Phe Thr
```

-continued

```
            180                 185                 190
Asn Asn Thr Gly Tyr Ala Ser Val Ala Ala Val Gln Ala Cys Phe
        195                 200                 205
Asp Tyr Ala Lys Ala Asn Gly Lys Val Val Asp Ala Arg Gly Trp Glu
        210                 215                 220
Gly Thr Val Asp Ser Thr Val Leu Met Asp Gly Ile Glu Val Val Gly
225                 230                 235                 240
Gly Thr Trp His Gly Lys Ala Asp Ile Arg Leu Leu Asn Ser Thr Phe
                245                 250                 255
Arg Asn Phe Val Ala Ser Thr Val Arg Val Ala Tyr Trp Gly Gly Glu
            260                 265                 270
Val Arg Ile Ala Asp Tyr Glu Phe Thr Ser Ala Pro Ser Asn Ser Lys
        275                 280                 285
Val Thr Ser Ile Leu Phe Gln Gly Asn Ile Ala Gly Gly Ser Tyr Val
        290                 295                 300
Ile Glu Asn Gly Ile His Arg Asn Gly Lys Phe Gly Ile Leu Gln Gln
305                 310                 315                 320
Gly Thr Gly Glu Ala Ile Thr Asn Gly Val Ile Arg Gly Ile Thr Met
                325                 330                 335
Met Asp Met Gln Gly Asp Gly Ile Glu Met Asn Val Ile Asn Lys His
                340                 345                 350
Tyr Asp Gly Gly Leu Leu Ile Glu Asn Ile Phe Leu Glu Asn Ile Asp
            355                 360                 365
Gly Thr Asn Ala Pro Ile Pro Leu Ser Asn Trp Gly Ile Gly Ile Gly
        370                 375                 380
Ile Ala Gly Gln Gly Pro Phe Gly Trp Asp Ala Ala Glu Thr Gln Tyr
385                 390                 395                 400
Ala Lys Asn Val Thr Val Arg Asn Val His Ala Pro Arg Gly Val Arg
                405                 410                 415
Gln Val Val His Phe Glu Val Thr Arg Asp Ser Thr Cys Glu Asn Val
                420                 425                 430
Val Ala Asn Pro Asp Leu Ser Val Ser Ile Gly Thr Gly Leu Thr Ala
            435                 440                 445
Ala Gly Val Ile Thr Tyr Gly Cys Lys Arg Met Thr Ile Asp Gly Val
        450                 455                 460
Val Gly Glu Pro Met Asn Thr Gly Ala Thr Ser Pro Asn Asp Ile Arg
465                 470                 475                 480
Ile Val Met Leu Glu Trp Gly Ala Asn Gln Ala Gly Ala Gly Gly Thr
                485                 490                 495
Pro Gly Ala Ala Cys Pro Ser Phe Asp Met Thr Val Arg Asn Val Gln
            500                 505                 510
Thr Arg Thr Gly Arg Phe Tyr Ala Gly Val Gly Ser Asp Asp Asp Asn
        515                 520                 525
Thr Asn Thr Tyr His Leu Glu Asn Ile His Cys Tyr Lys Met Thr Leu
        530                 535                 540
Phe Gly Val Ala Thr Leu Leu Asn Met Thr Asn Val Thr Gly Val Val
545                 550                 555                 560
Phe Asp Ala Val Gly Asp Asp Ser Ser Gly Thr Ser Ser Asn Gly
                565                 570                 575
Leu Tyr Pro Arg Lys Lys Thr Val Leu Asn Met Val Asn Val Asn Phe
            580                 585                 590
Tyr Gly Pro Gly Met Thr Glu Gly Ala Leu Tyr Ser Lys Ala Arg Tyr
        595                 600                 605
```

```
Ser Asp Ile Ser Thr Leu Asn Ser Asn Val Arg Ala Ile Pro Tyr Thr
        610                 615                 620

Asn Ile Gln Gly Asn Val Gly Val Ile Leu Ser Pro Val Asn Arg Met
625                 630                 635                 640

Tyr Thr Leu Pro Asn Ala Leu Ala Thr Leu Asp Gly Asn Glu Phe Pro
                645                 650                 655

Thr Gly Lys Glu Phe Cys Glu Gly Thr Val Leu Phe Lys Thr Asp Gly
                660                 665                 670

Ser Gly Gly Asn Phe Ile Val Thr Arg Phe Gly Ala Tyr Ile Pro Asp
                675                 680                 685

Asp Gly Asn Asn Phe Lys Val Arg Ala Ala Ala Gly Gln Thr Tyr
690                 695                 700

Leu Glu Gln Asn Leu Thr Pro Ala Gly Thr Gln Ala Ser Thr Ser Trp
705                 710                 715                 720

Leu Tyr His Lys Pro Ile Ser Ala Gly Thr Arg Leu Asn Val Pro Gly
                725                 730                 735

Ala Gly Pro Ser Gly Gly Thr Leu Thr Val Thr Val Arg Ala Pro
                740                 745                 750

Tyr Gln Val Asp Asn Asn Ile Gly Asn Pro Val Arg Ile Asp Ile Thr
                755                 760                 765

Pro Ala Ile Val Thr Ala Ile Pro Ala Gly Thr Gln Leu Ala Ala Thr
770                 775                 780

Tyr Pro Val Ala Tyr Ile Asp Tyr Lys Asp Asp Asp Lys
785                 790                 795

<210> SEQ ID NO 6
<211> LENGTH: 692
<212> TYPE: PRT
<213> ORGANISM: Artificial
<220> FEATURE:
<223> OTHER INFORMATION: Amino acid sequence for FLAG-tagged truncated
      form of colanic acid degrading enzyme (CAE).

<400> SEQUENCE: 6

Leu Ala Pro Leu Asp Arg Ala Val Arg Val Pro Asn Ser Glu Val Ser
1               5                   10                  15

Ile Asn Ala Leu Pro Asn Val Ala Gly Arg Arg Asn Lys Ala Leu Gly
                20                  25                  30

Phe Asp Ser Asn Gly Gln Pro Phe Met Ile Pro Leu Val Asp Ile Pro
                35                  40                  45

Asp Ser Ala Leu Ala Ile Ala Leu Ala Met Ala Asp Gly Gly Lys Trp
50                  55                  60

Ile Gly Thr Leu Gly Gly Gly Thr Phe Leu Asp Arg Gln Asp Thr Val
65                  70                  75                  80

Cys Leu Ser Glu Phe Thr Asn Asn Thr Gly Tyr Ala Ser Val Ala Ala
                85                  90                  95

Ala Val Gln Ala Cys Phe Asp Tyr Ala Lys Ala Asn Gly Lys Val Val
                100                 105                 110

Asp Ala Arg Gly Trp Glu Gly Thr Val Asp Ser Thr Val Leu Met Asp
                115                 120                 125

Gly Ile Glu Val Val Gly Gly Thr Trp His Gly Lys Ala Asp Ile Arg
130                 135                 140

Leu Leu Asn Ser Thr Phe Arg Asn Phe Val Ala Ser Thr Val Arg Val
145                 150                 155                 160

Ala Tyr Trp Gly Gly Glu Val Arg Ile Ala Asp Tyr Glu Phe Thr Ser
                165                 170                 175
```

```
Ala Pro Ser Asn Ser Lys Val Thr Ser Ile Leu Phe Gln Gly Asn Ile
            180                 185                 190

Ala Gly Gly Ser Tyr Val Ile Glu Asn Gly Ile His Arg Asn Gly Lys
        195                 200                 205

Phe Gly Ile Leu Gln Gln Gly Thr Gly Glu Ala Ile Thr Asn Gly Val
    210                 215                 220

Ile Arg Gly Ile Thr Met Met Asp Met Gln Gly Asp Gly Ile Glu Met
225                 230                 235                 240

Asn Val Ile Asn Lys His Tyr Asp Gly Gly Leu Leu Ile Glu Asn Ile
                245                 250                 255

Phe Leu Glu Asn Ile Asp Gly Thr Asn Ala Pro Ile Pro Leu Ser Asn
                260                 265                 270

Trp Gly Ile Gly Ile Gly Ile Ala Gly Gln Gly Pro Phe Gly Trp Asp
            275                 280                 285

Ala Ala Glu Thr Gln Tyr Ala Lys Asn Val Thr Val Arg Asn Val His
        290                 295                 300

Ala Pro Arg Gly Val Arg Gln Val Val His Phe Glu Val Thr Arg Asp
305                 310                 315                 320

Ser Thr Cys Glu Asn Val Val Ala Asn Pro Asp Leu Ser Val Ser Ile
                325                 330                 335

Gly Thr Gly Leu Thr Ala Ala Gly Val Ile Thr Tyr Gly Cys Lys Arg
            340                 345                 350

Met Thr Ile Asp Gly Val Val Gly Glu Pro Met Asn Thr Gly Ala Thr
        355                 360                 365

Ser Pro Asn Asp Ile Arg Ile Val Met Leu Glu Trp Gly Ala Asn Gln
    370                 375                 380

Ala Gly Ala Gly Gly Thr Pro Gly Ala Ala Cys Pro Ser Phe Asp Met
385                 390                 395                 400

Thr Val Arg Asn Val Gln Thr Arg Thr Gly Arg Phe Tyr Ala Gly Val
                405                 410                 415

Gly Ser Asp Asp Asp Asn Thr Asn Thr Tyr His Leu Glu Asn Ile His
            420                 425                 430

Cys Tyr Lys Met Thr Leu Phe Gly Val Ala Thr Leu Leu Asn Met Thr
        435                 440                 445

Asn Val Thr Gly Val Val Phe Asp Ala Val Gly Asp Asp Ser Ser Gly
    450                 455                 460

Gly Thr Ser Ser Asn Gly Leu Tyr Pro Arg Lys Lys Thr Val Leu Asn
465                 470                 475                 480

Met Val Asn Val Asn Phe Tyr Gly Pro Gly Met Thr Glu Gly Ala Leu
                485                 490                 495

Tyr Ser Lys Ala Arg Tyr Ser Asp Ile Ser Thr Leu Asn Ser Asn Val
            500                 505                 510

Arg Ala Ile Pro Tyr Thr Asn Ile Gln Gly Asn Val Gly Val Ile Leu
        515                 520                 525

Ser Pro Val Asn Arg Met Tyr Thr Leu Pro Asn Ala Leu Ala Thr Leu
    530                 535                 540

Asp Gly Asn Glu Phe Pro Thr Gly Lys Glu Phe Cys Glu Gly Thr Val
545                 550                 555                 560

Leu Phe Lys Thr Asp Gly Ser Gly Gly Asn Phe Ile Val Thr Arg Phe
                565                 570                 575

Gly Ala Tyr Ile Pro Asp Asp Gly Asn Asn Phe Lys Val Arg Ala Ala
            580                 585                 590

Ala Ala Gly Gln Thr Tyr Leu Glu Gln Asn Leu Thr Pro Ala Gly Thr
        595                 600                 605
```

```
Gln Ala Ser Thr Ser Trp Leu Tyr His Lys Pro Ile Ser Ala Gly Thr
    610                 615                 620

Arg Leu Asn Val Pro Gly Ala Gly Pro Ser Gly Gly Thr Leu Thr Val
625                 630                 635                 640

Thr Val Val Arg Ala Pro Tyr Gln Val Asp Asn Asn Ile Gly Asn Pro
                645                 650                 655

Val Arg Ile Asp Ile Thr Pro Ala Ile Val Thr Ala Ile Pro Ala Gly
            660                 665                 670

Thr Gln Leu Ala Ala Thr Tyr Pro Val Ala Tyr Ile Asp Tyr Lys Asp
        675                 680                 685

Asp Asp Asp Lys
    690

<210> SEQ ID NO 7
<211> LENGTH: 2373
<212> TYPE: DNA
<213> ORGANISM: Artificial
<220> FEATURE:
<223> OTHER INFORMATION: Nucleic acid sequence encoding a colanic acid
      degrading enzyme (CAE).

<400> SEQUENCE: 7
```

| | | | | | |
|---|---|---|---|---|---|
| atggcgaaca | gctataatgc | ttacgtggcg | aacggttcac | agaccgcatt | cctcgtcacg | 60 |
| ttcgagcagc | gcgtgttcac | tgagattcag | gtgtacctca | actccgaact | ccagacggaa | 120 |
| gggtacacct | acaactctgt | gaccaaacag | attatcttcg | caccgcccc | gctcgccggg | 180 |
| gtgattgtcc | gactccaacg | ctacacctct | gaggttctgc | tgaacaagtt | tggccaagac | 240 |
| gctgccttca | ccgggcagaa | ccttgacgag | aactttgagc | agattctgtt | caaggctgag | 300 |
| gaaactcagg | aagcatggct | cgcgccactt | gaccgcgccg | tccgtgttcc | gaactccgaa | 360 |
| gtctccatca | cgcattacc | gaacgtcgct | ggccgccgca | acaaggcact | gggctttgac | 420 |
| agcaatggtc | agccgttcat | gattcctctg | gtcgatatcc | cggactccgc | gctggcgatt | 480 |
| gctctggcaa | tggctgacgg | cggtaagtgg | attggtactc | tcggcggggg | cacgttcctc | 540 |
| gaccgtcagg | ataccgtctg | cctgtccgag | ttcaccaaca | cactgggta | cgcctctgtc | 600 |
| gccgctgcgg | tgcaggcttg | cttcgactat | gcgaaagcca | acggcaaggt | cgttgacgct | 660 |
| cgcggctggg | aaggtacggt | ggattccact | gtgctgatgg | acggtattga | ggtcgtcggc | 720 |
| ggtacgtggc | acggcaaggc | tgacattcgc | ctgctgaact | ccaccttccg | caacttcgtg | 780 |
| gcctctactg | tccgtgtcgc | ctactgggc | ggcgaggtgc | gtattgctga | ctatgagttc | 840 |
| accagcgcac | cgagcaactc | caaggttacg | tctatcctgt | tccaaggcaa | catcgccggg | 900 |
| ggcagctacg | tcattgagaa | cggtatccac | cgcaatggta | agttcggtat | tctccaacag | 960 |
| ggtactggcg | aggctatcac | caacggcgtt | atccgtggca | tcaccatgat | ggatatgcag | 1020 |
| ggtgacggta | tcgagatgaa | cgtaatcaac | aagcactatg | atggtggcct | gctgattgag | 1080 |
| aacatcttcc | ttgagaacat | cgacggcacc | aacgcgccta | tcccactgtc | caactgggc | 1140 |
| attggtatcg | gtatcgctgg | tcaaggcccg | ttcggttggg | atgctgctga | gacgcagtat | 1200 |
| gcgaagaacg | tcactgtccg | taacgtccat | gctccgcgtg | gtgtgcgtca | ggtcgtccac | 1260 |
| ttcgaggtta | cgcgtgacag | cacctgcgag | aacgtagtgg | ccaaccctga | cctgtccgtc | 1320 |
| tccattggta | ctggcctgac | tgccgctggt | gtaatcacgt | acggctgcaa | gcgcatgacc | 1380 |
| attgacggtg | tagtcggtga | gcctatgaac | accggagcaa | cctctccgaa | cgatattcgt | 1440 |
| atcgtgatgt | tggagtgggg | tgcgaaccaa | gcaggtgctg | gcgtacgcc | gggtgcagct | 1500 |

-continued

```
tgcccatcgt tcgacatgac cgtgcgtaac gtgcagaccc gtaccgggcg cttctatgct    1560
ggtgtcggct ccgacgatga caacaccaac acatatcacc ttgaaaacat tcactgttac    1620
aagatgacgc tgtttggtgt ggcaactctg ctgaacatga ccaacgtgac tggtgtggtg    1680
ttcgacgctg taggcgatga ctccagcggc ggtacgtcct ccaacggtct gtacccgcgt    1740
aagaagactg ttctcaacat ggtgaacgtg aacttctacg ggccgggcat gaccgagggt    1800
gcgctgtaca gtaaggctcg ctactcggat atcagcacgc tgaactccaa cgtgcgtgct    1860
atcccgtaca ccaacatcca aggtaacgtg ggtgtcatcc tgtctccggt caaccgcatg    1920
tacacgctgc cgaacgccct cgctacccct gacggtaatg agttccccac cgggaaagag    1980
ttctgcgaag gtactgtgct gttcaagacc gatggctccg gtggcaactt catcgtgacc    2040
cggttcggtg cgtacatccc ggatgacggt aacaacttca aggtgcgtgc tgctgccgct    2100
ggccagacgt atctggagca gaacctgact ccggctggta ctcaggcttc cacctcgtgg    2160
ctgtaccata agccaatctc tgctggtact cgactcaatg ttccgggtgc cgggccgagc    2220
ggcggtacgc tcactgtgac ggtggtgcgt gctccgtatc aggtggacaa caacatcgga    2280
aacccggtac gcatcgacat taccccggcc attgtgacgg caatccctgc gggaacgcag    2340
ctcgccgcta cctacccggt ggcttacatc taa                                 2373
```

<210> SEQ ID NO 8
<211> LENGTH: 2055
<212> TYPE: DNA
<213> ORGANISM: Artificial
<220> FEATURE:
<223> OTHER INFORMATION: Nucleic acid sequence encoding a truncated form of a colanic acid degrading enzyme (CAE).

<400> SEQUENCE: 8

```
ctcgcgccac ttgaccgcgc cgtccgtgtt ccgaactccg aagtctccat caacgcatta     60
ccgaacgtcg ctgccgcccg caacaaggca ctgggctttg acagcaatgg tcagccgttc    120
atgattcctc tggtcgatat cccggactcc gcgctggcga ttgctctggc aatggctgac    180
ggcggtaagt ggattggtac tctcggcggg ggcacgttcc tcgaccgtca ggataccgtc    240
tgcctgtccg agttcaccaa caacactggg tacgcctctg tcgccgctgc ggtgcaggct    300
tgcttcgact atgcgaaagc caacggcaag gtcgttgacg ctcgcggctg gaaggtacg    360 gtggattcca ctgtgctgat ggacggtatt gaggtcgtcg gcggtacgtg gcacggcaag    420
gctgacattc gcctgctgaa ctccaccttc cgcaacttcg tggcctctac tgtccgtgtc    480
gcctactggg gcggcgaggt gcgtattgct gactatgagt tcaccagcgc accgagcaac    540
tccaaggtta cgtctatcct gttccaaggc aacatcgccg ggggcagcta cgtcattgag    600
aacggtatcc accgcaatgg taagttcggt attctccaac agggtactgg cgaggctatc    660
accaacggcg ttatccgtgg catcaccatg atggatatgc agggtgacgg tatcgagatg    720
aacgtaatca acaagcacta tgatggtggc ctgctgattg agaacatctt ccttgagaac    780
atcgacggca ccaacgcgcc tatcccactg tccaactggg gcattggtat cggtatcgct    840
ggtcaaggcc cgttcggttg gaatgctgct gagacgcagt atgcgaagaa cgtcactgtc    900
cgtaacgtcc atgctccgcg tggtgtgcgt caggtcgtcc acttcgaggt tacgcgtgac    960
agcacctgcg agaactagt ggccaaccct gacctgtccg tctccattgg tactggcctg   1020
actgccgctg gtgtaatcac gtacggctgc aagcgcatga ccattgacgg tgtagtcggt   1080
gagcctatga acaccggagc aacctctccg aacgatattc gtatcgtgat gttggagtgg   1140
ggtgcgaacc aagcaggtgc tggcggtacg ccgggtgcag cttgcccatc gttcgacatg   1200
```

-continued

```
accgtgcgta acgtgcagac ccgtaccggg cgcttctatg ctggtgtcgg ctccgacgat    1260
gacaacacca acacatatca ccttgaaaac attcactgtt acaagatgac gctgtttggt    1320
gtggcaactc tgctgaacat gaccaacgtg actggtgtgg tgttcgacgc tgtaggcgat    1380
gactccagcg gcggtacgtc ctccaacggt ctgtacccgc gtaagaagac tgttctcaac    1440
atggtgaacg tgaacttcta cgggccgggc atgaccgagg gtgcgctgta cagtaaggct    1500
cgctactcgg atatcagcac gctgaactcc aacgtgcgtg ctatcccgta caccaacatc    1560
caaggtaacg tgggtgtcat cctgtctccg gtcaaccgca tgtacacgct gccgaacgcc    1620
ctcgctaccc ttgacggtaa tgagttcccc accgggaaag agttctgcga aggtactgtg    1680
ctgttcaaga ccgatggctc cggtggcaac ttcatcgtga cccggttcgg tgcgtacatc    1740
ccggatgacg gtaacaactt caaggtgcgt gctgctgccg ctggccagac gtatctggag    1800
cagaacctga ctccggctgg tactcaggct tccacctcgt ggctgtacca taagccaatc    1860
tctgctggta ctcgactcaa tgttccgggt gccggccga gcggcggtac gctcactgtg    1920
acggtggtgc gtgctccgta tcaggtggac aacaacatcg gaaacccggt acgcatcgac    1980 attccccgg ccattgtgac ggcaatccct gcgggaacgc agctcgccgc tacctacccg    2040
gtggcttaca tctaa                                                     2055
```

<210> SEQ ID NO 9
<211> LENGTH: 15
<212> TYPE: PRT
<213> ORGANISM: Artificial
<220> FEATURE:
<223> OTHER INFORMATION: Amino acid sequence of a colanic acid degrading enzyme (CAE) fragment.

<400> SEQUENCE: 9

Ala Asn Ser Tyr Asn Ala Tyr Val Ala Asn Gly Ser Gln Thr Ala
1               5                   10                  15

<210> SEQ ID NO 10
<211> LENGTH: 16
<212> TYPE: PRT
<213> ORGANISM: Artificial
<220> FEATURE:
<223> OTHER INFORMATION: Amino acid sequence of a colanic acid degrading enzyme (CAE) fragment.

<400> SEQUENCE: 10

Leu Leu Glu Gln Gly Thr Gly Glu Ala Leu Thr Asp Gly Val Leu Arg
1               5                   10                  15

<210> SEQ ID NO 11
<211> LENGTH: 16
<212> TYPE: PRT
<213> ORGANISM: Artificial
<220> FEATURE:
<223> OTHER INFORMATION: Amino acid sequence of a colanic acid degrading enzyme (CAE) fragment.

<400> SEQUENCE: 11

Val Pro Asn Ser Glu Val Ser Leu Asn Ala Leu Pro Asn Val Gln Arg
1               5                   10                  15

<210> SEQ ID NO 12
<211> LENGTH: 14
<212> TYPE: PRT
<213> ORGANISM: Artificial
<220> FEATURE:
<223> OTHER INFORMATION: Amino acid sequence of a colanic acid degrading -continued enzyme (CAE) fragment.

<400> SEQUENCE: 12

Leu Ala Asp Tyr Glu Phe Thr Ser Ala Pro Ser Asn Ser Lys
1               5                   10

<210> SEQ ID NO 13
<211> LENGTH: 8
<212> TYPE: PRT
<213> ORGANISM: Artificial
<220> FEATURE:
<223> OTHER INFORMATION: Amino acid sequence of a colanic acid degrading
      enzyme (CAE) fragment.

<400> SEQUENCE: 13

Tyr Ser Asp Leu Ser Thr Leu Asn
1               5

<210> SEQ ID NO 14
<211> LENGTH: 10
<212> TYPE: PRT
<213> ORGANISM: Artificial
<220> FEATURE:
<223> OTHER INFORMATION: Amino acid sequence of a colanic acid degrading
      enzyme (CAE) fragment.

<400> SEQUENCE: 14

Gln Leu Leu Phe Asp Thr Ala Pro Leu Ala
1               5                   10

<210> SEQ ID NO 15
<211> LENGTH: 9
<212> TYPE: PRT
<213> ORGANISM: Artificial
<220> FEATURE:
<223> OTHER INFORMATION: Amino acid sequence of a colanic acid degrading
      enzyme (CAE) fragment.

<400> SEQUENCE: 15

Ala Pro Tyr Gln Val Asp Asp Asn Leu
1               5

<210> SEQ ID NO 16
<211> LENGTH: 8
<212> TYPE: PRT
<213> ORGANISM: Artificial
<220> FEATURE:
<223> OTHER INFORMATION: Amino acid sequence of a colanic acid degrading
      enzyme (CAE) fragment.

<400> SEQUENCE: 16

Phe Gly Ala Tyr Leu Pro Asp Asp
1               5

<210> SEQ ID NO 17
<211> LENGTH: 6
<212> TYPE: PRT
<213> ORGANISM: Artificial
<220> FEATURE:
<223> OTHER INFORMATION: Amino acid sequence of a colanic acid degrading
      enzyme (CAE) fragment.

<400> SEQUENCE: 17

Leu Gly Thr Leu Gly Gly
1               5